(12) United States Patent
Williams et al.

(10) Patent No.: US 8,658,774 B2
(45) Date of Patent: *Feb. 25, 2014

(54) MEDITOPES AND RELATED MEDITOPE-MONOCLONAL ANTIBODY DELIVERY SYSTEMS, SYNTHESIS AND THERAPEUTIC USES THEREOF

(75) Inventors: John C. Williams, Monrovia, CA (US); David A. Horne, Duarte, CA (US); Yuelong Ma, Duarte, CA (US); Heng Wei Chang, Foster City, CA (US)

(73) Assignee: City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/270,207

(22) Filed: Oct. 10, 2011

(65) Prior Publication Data
US 2012/0177568 A1 Jul. 12, 2012

Related U.S. Application Data

(60) Provisional application No. 61/391,558, filed on Oct. 8, 2010.

(51) Int. Cl.
*C07K 14/00* (2006.01)
*C07K 1/00* (2006.01)
*C07K 16/00* (2006.01)
*C07K 17/00* (2006.01)
*A23J 1/00* (2006.01)
*G01N 33/566* (2006.01)
*G01N 33/53* (2006.01)

(52) U.S. Cl.
USPC .............................. 530/413; 436/501; 435/7.1

(58) Field of Classification Search
None
See application file for complete search history.

(56) References Cited

U.S. PATENT DOCUMENTS

| | | | |
|---|---|---|---|
| 7,754,853 | B2 | 7/2010 | Hellendoorn et al. |
| 2004/0067503 | A1 | 4/2004 | Tan et al. |
| 2005/0042664 | A1 | 2/2005 | Wu et al. |
| 2008/0038260 | A1 | 2/2008 | Ponath et al. |
| 2009/0005257 | A1 | 1/2009 | Jespers et al. |
| 2009/0074780 | A1 | 3/2009 | Urech et al. |
| 2009/0202568 | A1 | 8/2009 | Eriksson et al. |
| 2010/0068135 | A1 | 3/2010 | Rock |
| 2010/0076178 | A1 | 3/2010 | Ghayur et al. |

FOREIGN PATENT DOCUMENTS

| | | |
|---|---|---|
| WO | WO 96/40210 | 12/1996 |
| WO | WO-2009/062051 | 5/2009 |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Skolnick et al., From genes to protein structure an function: novel applications of computational approaches in the genomic era, Trends in Biotech. 18: 34-39, 2000.*
Paul, Fundamental Immunology, 3rd Edition, 1993, pp. 292-295.*
Of Lofgren et al., J. Immunol., 2007, 178:7467-7472.*
Chung, C. H., et al., "Cetuximab-Induced Anaphylaxis and IgE Specific for Galactose-alpha-1,3-Galactose," N. Eng. J. Med. 358(11):1109-1117 (2008).
Horiuchi, T., et al., "Transmembrane TNF-alpha: Structure, Function and Interaction with Anti-TNF Agents," Rheumatology 49:1215-1228 (2010).
Lomash, S., et al., "An Antibody as Surrogate Receptor Reveals Determinants of Activity of an Innate Immune Peptide Antibiotic," J. Biol. Chem. 285(46):35750-35758 (2010).
Nilson, B. H.K., et al., "Purification of Antibodies Using Protein L-Binding Framework Structures in the Light Chain Variable Domain," J. Immunol. Methods 164:33-40 (1993).
Robert, F., et al., "Phase I Study of Anti-Epidermal Growth Factor Receptor Antibody Cetuximab in Combination with Radiation Therapy in Patients with Advanced Head and Neck Cancer," J. Clin. Oncol. 19:3234-3243 (2001).
Rosenberg, M. E., et al., "Apolipoprotein J/Clusterin Prevents a Progressive Glomerulopathy of Aging," Mol. Cell. Biol. 22(6):1893-1902 (2002).
United States Patent and Trademark Office, International Search Report and Written Opinion for PCT/US11/55656 dated May 10, 2012.
Nygaard, S., et al., Uniprot Accession No. F4WN58 (online). Jun. 28, 2011, retrieved from <URL:http://www.uniprot.org/uniprot/F4WN58.txt?version=1>, p. 1.
United States Patent and Trademark Office, International Search Report and Written Opinion for PCT/US2012/032938, dated Oct. 17, 2012.
Accardi, L., et al., "Antibodies in Single-Chain Format Against Tumour-Associated Antigens: Present and Future Applications," Curr. Med. Chem. 17:1730-1755 (2010).

(Continued)

*Primary Examiner* — Hong Sang
(74) *Attorney, Agent, or Firm* — Morrison & Foerster LLP

(57) ABSTRACT

Meditope variants and methods for their use are provided herein. A meditope variant as described herein comprises a peptide having a sequence CQFDLSTRRLKC (SEQ ID NO:1) or CQYNLSSRALKC (SEQ ID NO:2) that has one or more modifications at of least one amino acid residue of the sequence. Multivalent meditope variant tethering entities are also provided. Such entities may include two or more meditopes coupled via a long linker, multivalent scaffold, biotin-streptavidin, or IgG Fc domain. Further, methods of treating, imaging or diagnosing a disease or condition are provided. Such methods may include administering a therapeutically effective amount of a pharmaceutical composition to a subject, the pharmaceutical compound comprising an antibody-meditope complex; a multivalent tethering agent in combination with a monoclonal antibody or functional fragment thereof; or a combination thereof.

8 Claims, 44 Drawing Sheets

(56) References Cited

OTHER PUBLICATIONS

Adams, G. P., et al., "High Affinity Restricts the Localization and Tumor Penetration of Single-Chain Fv Antibody Molecules," Cancer Res. 61:4750-4755 (2001).
Adams, J., et al., "Potent and Selective Inhibitors of the Proteasome: Dipeptidyl Boronic Acids," Biorog. Med. Chem. Lett. 8:333-338 (1998).
Adams, P. D., et al., "PHENIX: Building New Software for Automated Crystallographic Structure Determination," Acta Crystallogr. D Biol. Crystallogr. 58:1948-1954 (2002).
Adessi, C., et al., "Converting a Peptide into a Drug: Strategies to Improve Stability and Bioavailability," Curr. Med. Chem. 9: 963-978 (2002).
Akamatsu, Y., et al., "Whole IgG Surface Display on Mammalian Cells: Application to Isolation of Neutralizing Chicken Monoclonal Anti-IL-12 Antibodies," J. Immunol. Methods 327:40-52 (2007).
Alley, S. C., et al., "Antibody-Drug Conjugates: Targeted Drug Delivery for Cancer," Curr. Opin. Chem. Biol. 14:529-537 (2010).
Auffinger, P., et al., "Halogen Bonds in Biological Molecules," PNAS 101(48):16789-16794 (2004).
Beck, A., et al., "Trends in Glycosylation, Glycoanalysis and Glycoengineering of Therapeutic Antibodies and Fc-Fusion Proteins," Curr. Pharm. Biotech. 9:482-501 (2008).
Beck, A., et al., "Strategies and Challenges for the Next Generation of Therapeutic Antibodies," Nat. Rev. Immunol. 10:345-352 (2010).
Bilgicer, B., et al., "A Synthetic Trivalent Hapten that Aggregates Anti-2,4-DNP IgG into Bicyclic Trimers," J. Am. Chem. Soc. 129(12):3722-3728 (2007).
Bilgicer, B., et al., "A Non-Chromatographic Method for the Purification of a Bivalently Active Monoclonal IgG Antibody from Biological Fluids," J. Am. Chem. Soc. 131(26):9361-9367 (2009).
Bokemeyer,C., et al., "Fluorouracil, Leucovorin, and Oxaliplatin With and Without Cetuximab in the First-Line Treatment of Metastatic Colorectal Cancer," J. Clin. Oncol. 27(5): (2009).
Bretscher, L. E., et al., "Structural Characterization and Kinetics of Nitric-Oxide Synthase Inhibition by Novel $N^5$-(Iminoalkyl)- and $N^5$-(Iminoalkenyl)- Ornithines," J. Biol. Chem. 278(47):46789-46797 (2003).
Butlin, N. G., et al., "Antibodies with Infinite Affinity: Origins and Applications," Acc. Chem. Res. 39:780-787 (2006).
Cardarelli, P. M., et al., "Binding to CD20 by Anti-B1 Antibody or F(ab')$_2$ is Sufficient for Induction of Apoptosis in B-Cell Lines," Cancer Immunol. Immunother. 51:15-24 (2002).
Carson, K. R., et al., "Monoclonal Antibody-Associated Progressive Multifocal Leucoencephalopathy in Patients Treated with Rituximab, Natalizumab, and Efalizumab: A Review from the Research on Adverse Drug Events and Reports (RADAR) Project," Lancet Oncol. 10:816-824 (2009).
Chen, V. B., et al., "MolProbity: All-Atom Structure Validation for Macromolecular Crystallography," Acta Crystallogr. D66:12-21 (2010).
Chih, H.W., et al., "Identification of Amino Acid Residues Responsible for the Release of Free Drug from an Antibody-Drug Conjugate Utilizing Lysine-Succinimidyl Ester Chemistry," J. Pharm. Sci. 100:2518-2525 (2011).
Chmura, A. J., et al., "Antibodies with Infinite Affinity," PNAS 98(15):8480-8484 (2001).
Cho, H.S., et al., "Structure of the Extracellular Region of HER2 Alone and in Complex with the Herceptin Fab," Nature 421:756-760 (2003).
Collis, A. V. J., et al., "Analysis of the Antigen Combining Site: Correlations Between Length and Sequence Composition of the Hypervariable Loops and the Nature of the Antigen," J. Mol. Biol. 325:337-354 (2003).
Dechant, M., et al., "Complement-Dependent Tumor Cell Lysis Triggered by Combinations of Epidermal Growth Factor Receptor Antibodies," Cancer Res. 68:4998-5003 (2008).

Demarest, S. J., et al., "Antibody Therapeutics, Antibody Engineering, and the Merits of Protein Stabiilty," Curr. Opin. Drug Discov. Devel. 11(5):675-687 (2008).
Denardo, G., et al., "Dose Intensified Molecular Targeted Radiotherapy for Cancer—Lymphoma as a Paradigm," Semin. Nucl. Med. 40:136-144 (2010).
Derksen, D. J., et al., "Antimicrobial Leucocin Analogues with a Disulfide Bridge Replaced by a Carbocycle or by Noncovalent Interactions of Allyl Glycine Residues," J. Am. Chem. Soc. 128:14252-14253 (2006).
Donaldson, J. M., et al., "Design and Development of Masked Therapeutic Antibodies to Limit Off-Target Effects," Cancer Biol. Ther. 8(22):2145-2150 (2009).
Doppalapudi, V. R., et al., "Chemical Generation of Bispecific Antibodies," PNAS 107(52):22611-22616 (2010).
Doppalapudi, V. R., et al., "Chemically Programmed Antibodies: Endothelin Receptor Targeting CovX-Bodies™," Bioorg. Med. Chem. Lett. 17:501-506 (2007).
Dornan, D., et al., "Therapeutic Potential of an Anti-CD79b Antibody-Drug Conjugate, Anti-CD79b-vc-MMAE, for the Treatment of Non-Hodgkin Lymphoma," Blood 114:2721-2729 (2009).
Du, J., et al., "Structural Basis for Recognition of CD20 by Therapeutic Antibody Rituximab," J. Biol. Chem. 282(20):15073-15080 (2007).
Emsley, P., et al., "Coot: Model-Building Tools for Molecular Graphics," Acta Crystallogr. D60:2126-2132 (2004).
Erlanson, D. A., et al., "Discovery of a Potent and Highly Selective PDK1 Inhibitor Via Fragment-based Drug Discovery," Bioorg. Med. Chem. Lett. 21:3078-3083 (2011).
Ferenczy, G. G., et al., Thermodynamics Guided Lead Discovery and Optimization, Drug Discov. Today 15:919-932 (2010).
Gencoglan, G., et al., "Two Cases of Acneiform Eruption Induced by Inhibitor of Epidermal Growth Factor Receptor," Skin Pharmacol. Physiol. 20:260-262 (2007).
Goodwin, D. A., et al., "Pretargeted Peptide Imaging and Therapy," Cancer Biother. Radiopharm. 14(3):145-152 (1999).
Graille, M., et al., "Crystal Structure of a *Staphylococcus aureus* Protein a Domain Complexed with the Fab Fragment of a Human IgM Antibody: Structural Basis for Recognition of B-Cell Receptors and Superantigen Activity," PNAS 97(10):5399-5404 (2000).
Graille, M., et al., "Complex Between *Peptostreptococcus magnus* Protein L and a Human Antibody Reveals Structural Convergence in the Interaction Modes of Fab Binding Proteins," Structure 9:679-687 (2001).
Graille, M., et al., "Evidence for Plasticity and Structural Mimicry at the Immunoglobulin Light Chain-Protein L Interface," J. Biol. Chem. 277(49):47500-47506 (2002).
Green, D. J., et al., "Pretargeted Radioimmunotherapy for B-Cell Lymphomas," Clin. Cancer Res. 13:5598S-5603S (2007).
Guay, D., et al., "Therapeutic Utility and Medicinal Chemistry of Cathepsin C Inhibitors," Curr. Topics Med. Chem. 10:708-716 (2010).
Hansel, T. T., et al., "The Safety and Side Effects of Monoclonal Antibodies," Nat. Rev. Drug. Disc. 9:325-338 (2010).
Hardegger, L. A., et al., "Systematic Investigation of Halogen Bonding in Protein-Ligand Interactions," Angew. Chem. Int. Ed. 50:314-318 (2011).
Hartmann, C., et al., "Peptide Mimotopes Recognized by Antibodies Cetuximab and Matuzumab Induce a Functionally Equivalent Anti-EGFR Immune Response," Oncogene 29:4517-4527 (2010).
Hernandes, M. Z., et al., "Halogen Atoms in the Modern Medicinal Chemistry: Hints for the Drug Design," Curr. Drug Targets 11:303-314 (2010).
Hughes, S. J., et al., "Fragment Based Discovery of a Novel and Selective PI3 Kinase Inhibitor," Bioorg. Med. Chem. Lett. 21:6586-6590 (2011).
Hutchins, B. M., et al., "Site-Specific Coupling and Sterically Controlled Formation of Multimeric Antibody Fab Fragments with Unnatural Amino Acids," J. Mol. Biol. 406:595-603 (2011).
Junutula, J. R., et al., "Site-Specific Conjugation of a Cytotoxic Drug to an Antibody Improves the Therapeutic Index," Nat. Biotech. 26(8):925-932 (2008).

(56) References Cited

OTHER PUBLICATIONS

Kamat, V., et al., "Enhanced EGFR Inhibition and Distinct Epitope Recognition by EGFR Antagonistic mAbs C225 and 425," Cancer Biol. Ther. 7(5):726-733 (2008).
Kiessling, L. L., et al., "Chemical Approaches to Glycobiology," Annu. Rev. Biochem. 79:619-653 (2010).
Ladbury, J. E., et al., "Adding Calorimetric Data to Decision Making in Lead Discovery: A Hot Tip," Nat. Rev. Drug Disc. 9:23-27 (2010).
Lazar, G. A., et al., "Engineered Antibody Fc Variants with Enhanced Effector Function," PNAS 103(11):4005-4010 (2006).
Lesch, H. P., et al., "Avidin-Biotin Technology in Targeted Therapy," Expert Opin. Drug Deliv. 7(5):551-564 (2010).
Li, M., et al., "Mimotope Vaccination for Epitope-Specific Induction of Anti-CD20 Antibodies," Cell. Immunol. 239:136-143 (2006).
Li, S., et al., "Structural Basis for Inhibition of the Epidermal Growth Factor Receptor by Cetuximab," Cancer Cell 7:301-311 (2005).
Liu, C. C., et al., "Adding New Chemistries to the Genetic Code," Annu. Rev. Biochem. 79:413-444 (2010).
Lowe, C. R., et al., "New Developments in Affinity Chromatography with Potential Application in the Production of Biopharmaceuticals," J. Biochem. Biophys. Methods 49:561-574 (2001).
Mammen, M., et al., "Polyvalent Interactions in Biological Systems: Implications for Design and Use of Multivalent Ligands and Inhibitors," Angew. Chem. Int. Ed. 37:2754-2794 (1998).
McCoy, A. J., et al., "Phaser Crystallographic Software," J. Appl. Cryst. 40:658-674 (2007).
Meares, C. F., et al., "The Chemistry of Irreversible Capture," Adv. Drug Deliv. Rev. 60(12:1383-1388 (2008).
Meira, D. D., et al., "Different Antiproliferative Effects of Matuzumab and Cetuximab in A431 Cells are Associated with Persistent Activity of the MAPK Pathway," Eur. J. Cancer 45:1265-1273 (2009).
Melosky, B., et al., "Management of Skin Rash During EGFR-Targeted Monoclonal Antibody Treatment for Gastrointestinal Malignancies: Canadian Recommendations," Curr. Oncol. 16(1): 16-26 (2009).
Meredith, R. F., et al., "Pretargeted Radioimmunotherapy," Int. J. Rad.Oncol. Biol. Phys. 66(2):S57-S59 (2006).
Milo, L. J., et al., "Chemical and Biological Evaluation of Dipeptidyl Boronic Acid Proteasome Inhibitors for Use in Prodrugs and Pro-Soft Drugs Targeting Solid Tumors," J. Med. Chem. 54:4365-4377 (2011).
Molloy, E. S., et al., "Targeted but not Trouble-Free: Efalizumab and PML," Nat. Rev. Rheumatol. 5:418-419 (2009).
Morse, L., et al., "EGFR-Targeted Therapy and Related Skin Toxicity," Semin. Oncol. Nurs. 22(3):152-162 (2006).
Moss, L., et al., "Trastuzumab-Induced Cardiotoxicity," Oncol. Nurs. Forum 36(6): 676-685 (2009).
Mossessova, E., et al., "Ulp1-SUMO Crystal Structure and Genetic Analysis Reveal Conserved Interactions and a Regulatory Element Essential for Cell Growth in Yeast," Mol. Cell 5:865-876 (2000).
Muller, D., et al., "Bispecific Antibodies for Cancer Immunotherapy," Biodrugs 24(2):89-98 (2010).
Muller, S., et al., "Rigid Conformation of an Immunoglobulin Domain Tandem Repeat in the A-Band of the Elastic Muscle Protein Titin," J. Mol. Biol. 371:469-480 (2007).
Nicola, G., et al., "Crystal Structure of *Escherichia coli* Penicillin-Binding Protein 5 Bound to a Tripeptide Boronic Acid Inhibitor: A Role for Ser-110 in Deacylation," Biochem. 44(23): 8207-8217 (2005).
Pagel, J. M., et al., "Comparison of a Tetravalent Single-Chain Antibody-Streptavidin Fusion Protein and an Antibody-Streptavidin Chemical Conjugate for Pretargeted Anti-CD20 Radioimmunotherapy of B-Cell Lymphomas," Blood 108:328-336 (2006).
Pakkala, M., et al., "Mimetics of the Disulfide Bridge Between the N- and C-Terminal Cysteines of the KLK3-Stimulating Peptide B-2," Amino Acids 39:233-242 (2010).
Pugashetti, R., et al., "Efalizumab Discontinuation: A Practical Strategy," J. Dermatolog. Treat. 20(3):132-136 (2009).
Rao, J., et al., "A Trivalent System from Vancomycin-D-Ala-D-Ala with Higher Affinity Than Avidin-Biotin," Science 280:708-711 (1998).
Riemer, A. B., et al., "Generation of Peptide Mimics of the Epitope Recognized by Trastuzumab on the Oncogenic Protein Her-2/neu," J. Immunol. 173:394-401 (2004).
Riemer, A. B., et al., Vaccination with Cetuximab Mimotopes and Biological Properties of Induced Anti-Epidermal Growth Factor Receptor Antibodies, J. Natl. Cancer Inst. 97(22):1663-1670 (2005).
Rivera, F., et al., "Cetuximab in Metastatic or Recurrent Head and Neck Cancer: The Extreme Trial," Expert Rev. Anticancer Ther. 9(10):1421-1428 (2009).
Roe, E., et al., "Description and Management of Cutaneous Side Effects During Cetuximab or Erlotinib Treatments: A Prospective Study of 30 Patients," J. Am. Acad. Dermatol. 55(3):429-437 (2006).
Rossi, E. A., et al., "Stably Tethered Multifunctional Structures of Defined Composition Made by the Docket and Lock Method for Use in Cancer Targeting," PNAS 103(18):6841-6846 (2006).
Rudnick, S. I., et al., "Affinitiy and Avidity in Antibody-Based Tumor Targeting," Cancer Biother. Radiopharm. 24(2):155-161 (2009).
Scheuer, W., et al., "Strongly Enhanced Antitumor Activity of Trastuzumab and Pertuzumab Combination Treatment on HER2-Positive Human Xenograft Tumor Models," Cancer Res. 69:9330-9336 (2009).
Schrag, D., et al., "Cetuximab Therapy and Symptomatic Hypomagnesemia," J. Natl. Cancer Inst. 97(16):1221-1224 (2005).
Seeman, N. C., "DNA in a Material World," Nature 421:427-431 (2003).
Shan, D., et al., "Apoptosis of Malignant Human B Cells by Ligation of CD20 with Monoclonal Antibodies," Blood 91(5):1644-1652 (1998).
Sharav, T., et al., "Mimotope Vaccines for Cancer Immunotherapy," Vaccine 25:3032-3037 (2007).
Sharkey, R. M., et al., "Recombinant Bispecific Monoclonal Antibodies Prepared by the Dock-and-Lock Strategy for Pretargeted Radioimmunotherapy," Semin. Nucl. Med. 40(3):190-203 (2010).
Sheedy, C., et al., "Isolation and Affinity Maturation of Hapten-Specific Antibodies," Biotech. Adv. 25:333-352 (2007).
Shirasaki, Y., et al., "Exploration of Orally Available Calpain Inhibitors 2: Peptidyl Hemiacetal Derivatives," J. Med. Chem. 49:3926-3932 (2006).
Shuker, S. B., et al., "Discovering High-Affinity Ligands for Proteins: SAR by NMR," Science 274:1531-1534 (1996).
Spangler, J. B., et al., "Combination Antibody Treatment Down-Regulates Epidermal Growth Factor Receptor by Inhibiting Endosomal Recycling," PNAS 107(30):13252-13257 (2010).
Stymiest, J. L., et al., "Synthesis of Oxytocin Analogues with Replacement of Sulfur by Carbon Gives Potent Antagonists with Increased Stability," J. Org. Chem. 70:7799-7809 (2005).
Teillaud, J.L., et al., "Engineering of Monoclonal Antibodies and Antibody-Based Fusion Proteins: Successes and Challenges," Expert Opin. Biol. Ther. 5(Suppl. 1):S15-S27 (2005).
Thakur, A., et al., "Cancer Therapy with Bispecific Antibodies: Clinical Experience," Curr. Opin. Mol. Ther. 12(3):340-349 (2010).
Van Cutsem, E. V., et al., "Cetuximab and Chemotherapy as Initial Treatment for Metastatic Colorectal Cancer," N. Eng. J. Med. 360:1408-1417 (2009).
Wakankar, A. A., et al., "Physicochemical Stability of the Antibody-Drug Conjugate Trastuzumab-DM1: Changes due to Modification and Conjugation Processes," Bioconjugate Chem. 21:1588-1595 (2010).
Young, W. W., et al., "Staphylococcal Protein a Binding to the Fab Fragments of Mouse Monoclonal Antibodies," J. Immunol. 133(6): 3163-3166 (1984).

\* cited by examiner

A)

```
Light Chain
Kabat Number    10    38--------43    83-----87    100----105    165
cetuximab       I     QRTNGS          IADYY        AGTKLE        E
ch 14.18        S     QKPGQS          LGVYF        AGTKLE        E
trastuzumab     S     QKPGKA          FATYY        QGTKVE        E Heavy Chain
Kabat Number    39--------44    87-89    105-108    149    168-169
cetuximab       QSPGKG          TAI      QGTL       E      PA
ch 14.18        QNIGKS          SAV      QGTS       E      PA
trastuzumab     QAPGKG          TAV      QGTL       E      PA
```

B)

Figure 4 A-C
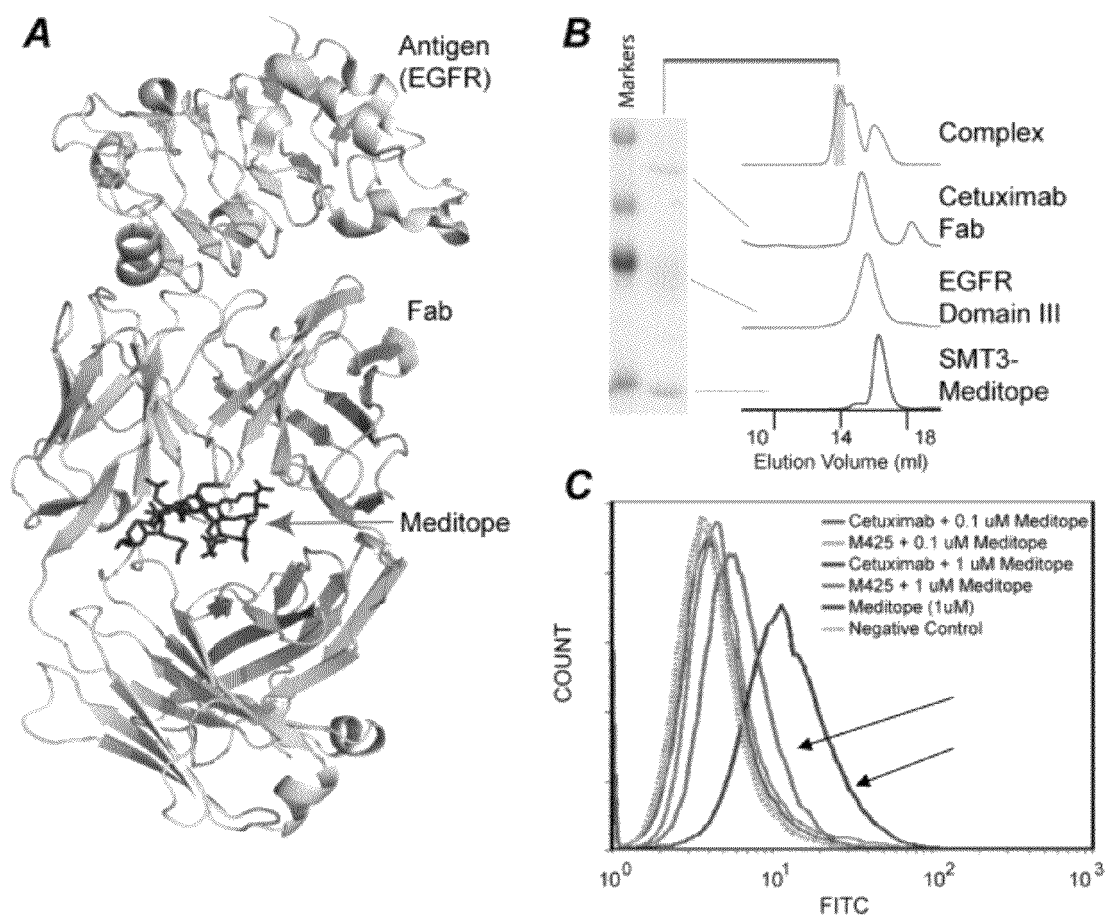

Figure 4D
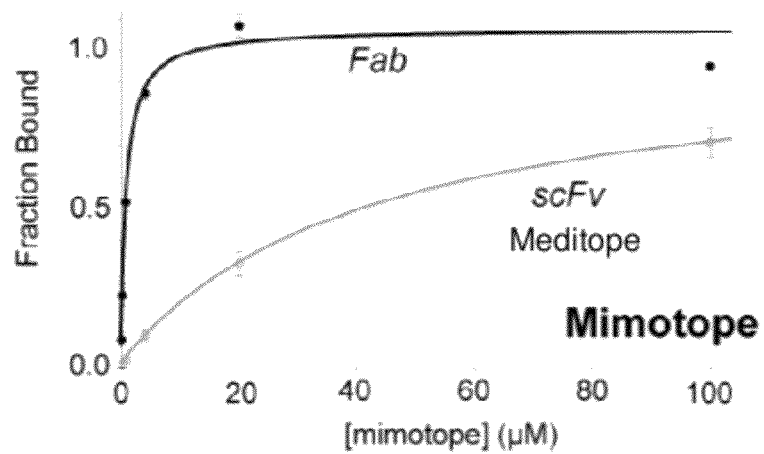
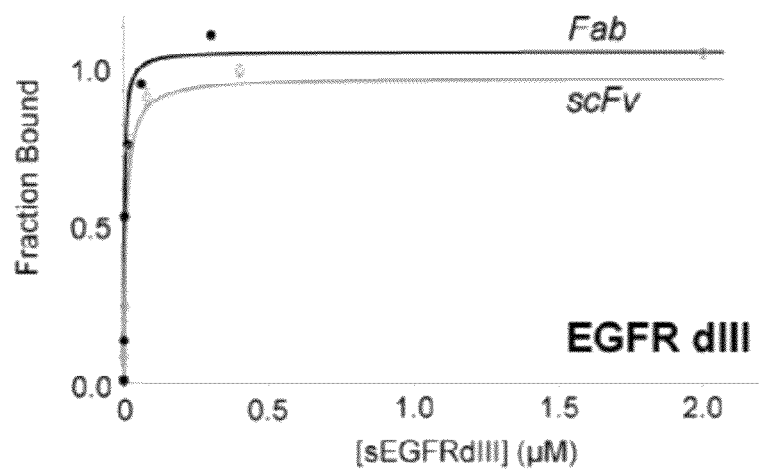

Figure 13B
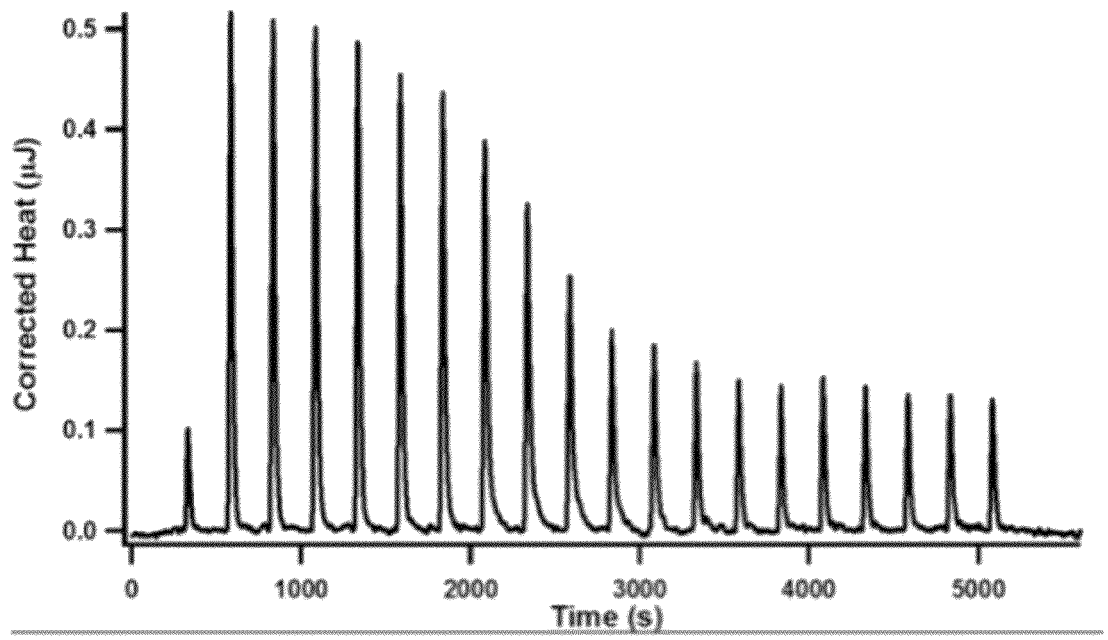
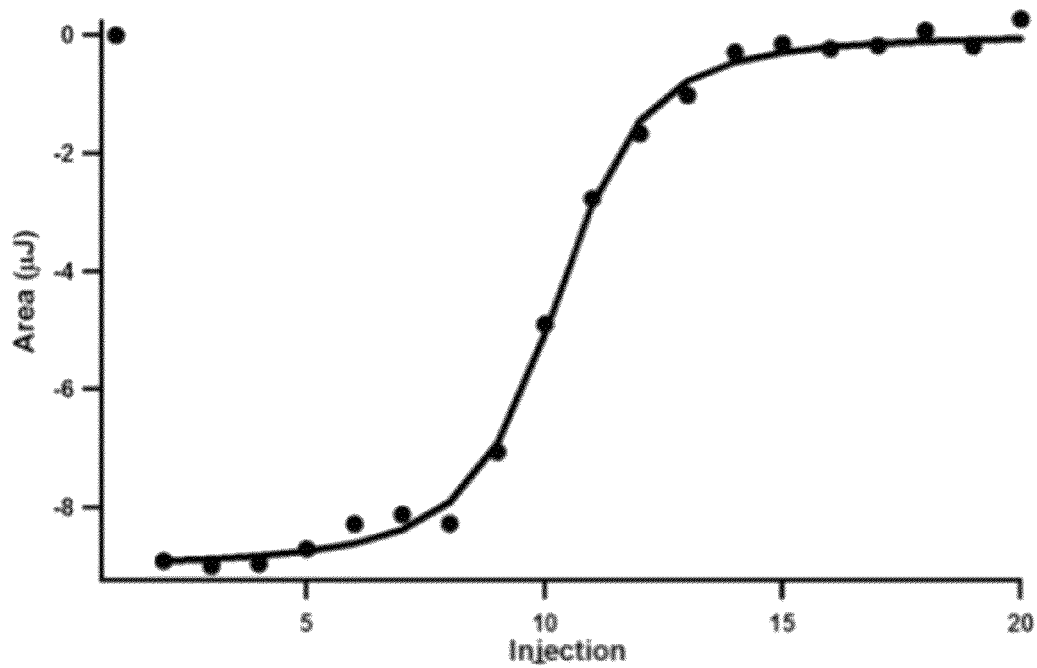

Modified Arg8    R=alkyl

Figure 22

Meditope-Fc (SEQ ID NO:3 nucleic acid and SEQ ID NO: 4 amino acid)

```
acacccaagctggctagcgacaccatgaagtgtagctgggtcatcttctttctgatggca
 T  P  K  L  A  S  D  T  M  K  C  S  W  V  I  F  F  L  M  A
gtcgtgacaggagtgaattcgtgccagtttgacctgtcaactcggcgactgaaatgcggt
 V  V  T  G  V  N  S  C  Q  F  D  L  S  T  R  R  L  K  C  G
gggggctccggttcaggctcgggcggttcatcgggaggagggggagggaacctaagtca
 G  G  S  G  S  G  S  G  G  S  S  G  G  G  G  E  P  K  S
tgcgataagacgcacacctgtcctccatgcccagcccccgagttgcttggtgggcctca
 C  D  K  T  H  T  C  P  P  C  P  A  P  E  L  L  G  P  S
gtattcctcttccctccaaaacccaaagacaccttgatgatttcccgcacgccggaagtc
 V  F  L  F  P  P  K  P  K  D  T  L  M  I  S  R  T  P  E  V
acgtgtgtggtcgtggatgtgagccatgaggatcccgaggtgaagttcaattggtacgtg
 T  C  V  V  V  D  V  S  H  E  D  P  E  V  K  F  N  W  Y  V
gatggagtagaggtacacaacgcgaaaacgaagcccagggaggaacagtacaattccaca
 D  G  V  E  V  H  N  A  K  T  K  P  R  E  E  Q  Y  N  S  T
tatcgcgtggtgtccgtgcttactgtgttgcatcaagactggctgaatgggaaggagtat
 Y  R  V  V  S  V  L  T  V  L  H  Q  D  W  L  N  G  K  E  Y
aagtgcaaagtatcaaacaaggcgctgcctgctccaatcgaaaagaccatctcgaaggcg
 K  C  K  V  S  N  K  A  L  P  A  P  I  E  K  T  I  S  K  A
aaaggacaacccagagaaccccaagtctacacgcttccgccctcgcgggatgagctcacc
 K  G  Q  P  R  E  P  Q  V  Y  T  L  P  P  S  R  D  E  L  T
aaaaaccaggtatccctcacttgtttggtaaaaggattctacccgtcggacattgcagtc
 K  N  Q  V  S  L  T  C  L  V  K  G  F  Y  P  S  D  I  A  V
gagtgggagtcgaatgggcagccggaaaacaactacaaaacaacaccgcccgtcttggac
 E  W  E  S  N  G  Q  P  E  N  N  Y  K  T  T  P  P  V  L  D
tccgatggttcgttctttctctattcgaagctcaccgtagacaagtcgaggtggcagcag
 S  D  G  S  F  F  L  Y  S  K  L  T  V  D  K  S  R  W  Q  Q
ggcaacgtcttttcgtgctcagtgatgcatgaggcccttcacaatcactatacgcagaaa
 G  N  V  F  S  C  S  V  M  H  E  A  L  H  N  H  Y  T  Q  K
agcctgagcctgtcaccggggaagtaa
 S  L  S  L  S  P  G  K  -
```

Figure 27
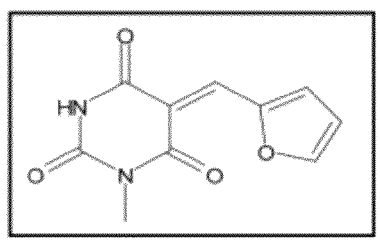
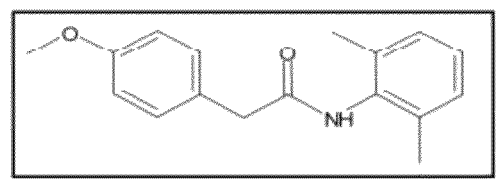
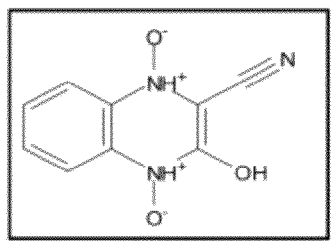
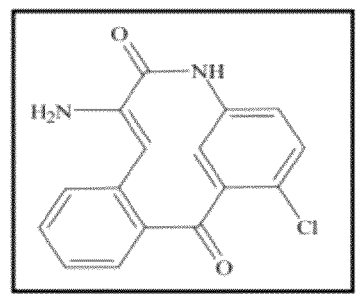
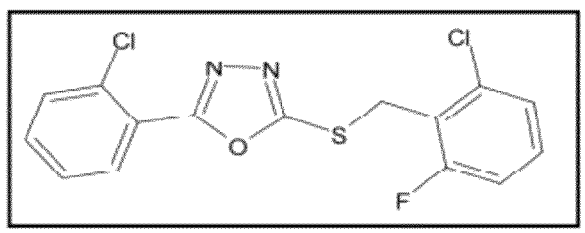

Figure 30
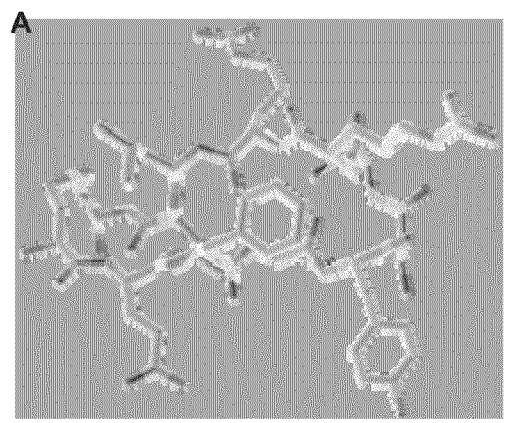
5
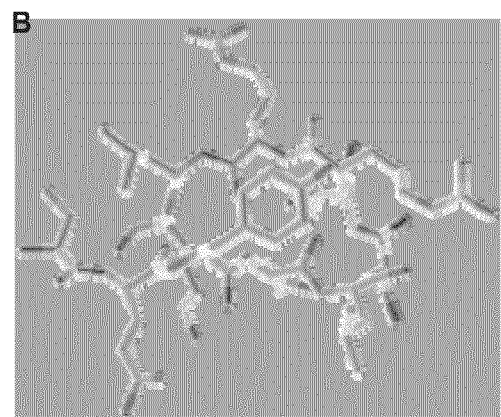
6
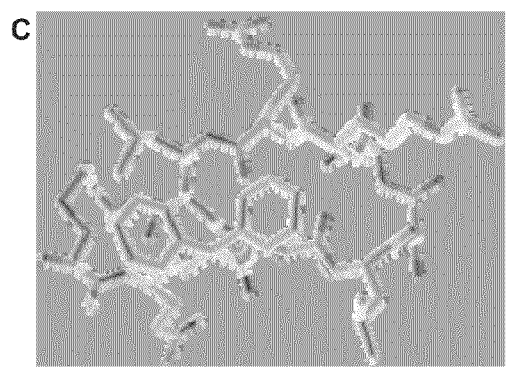
7
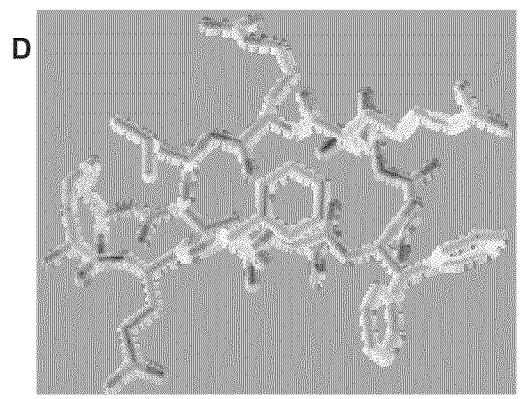
8
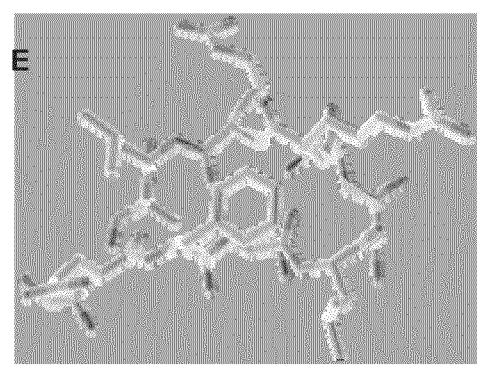
12
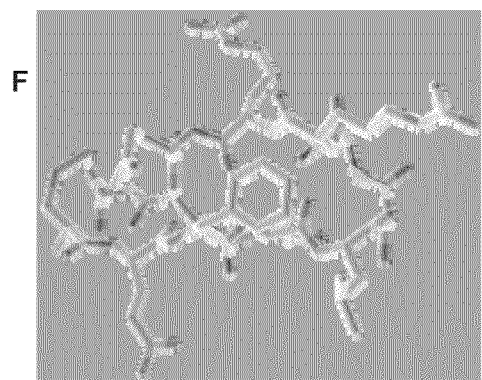
13

Figure 30 (cont'd)
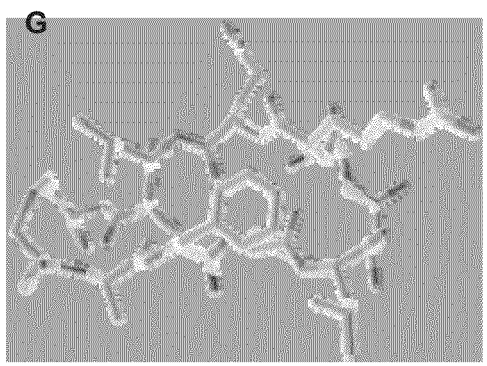
14
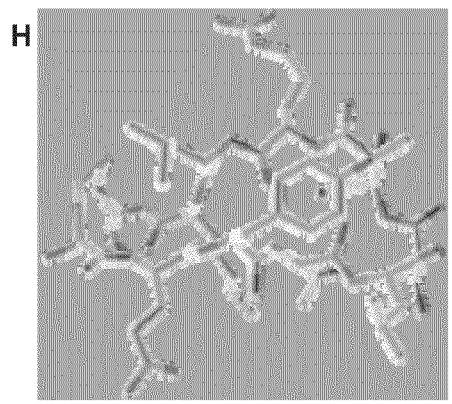
15
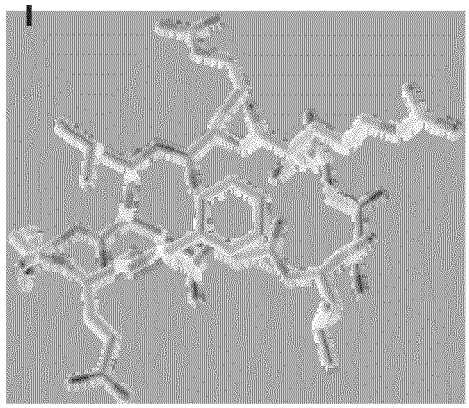
21
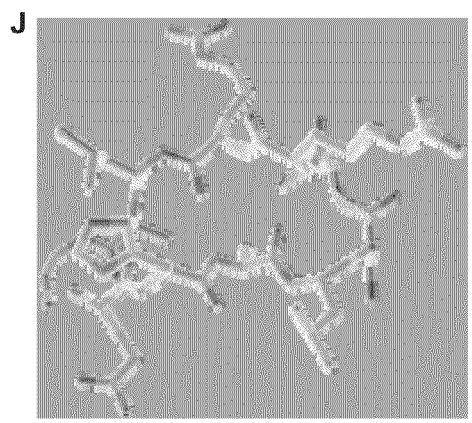
22
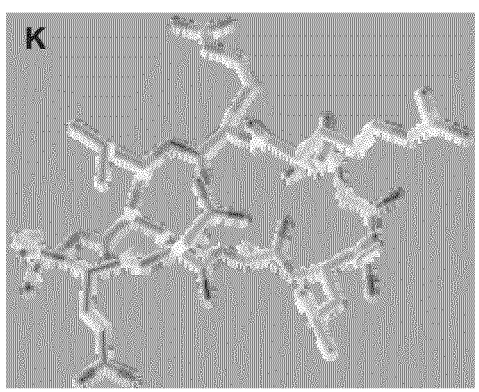
23
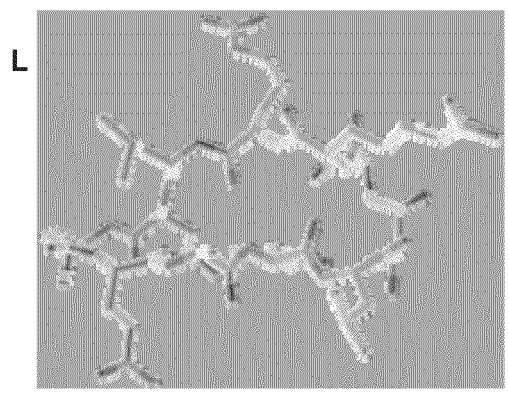
24

Figure 30 (cont'd)
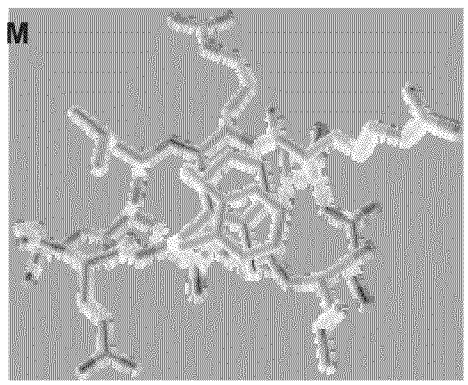
25
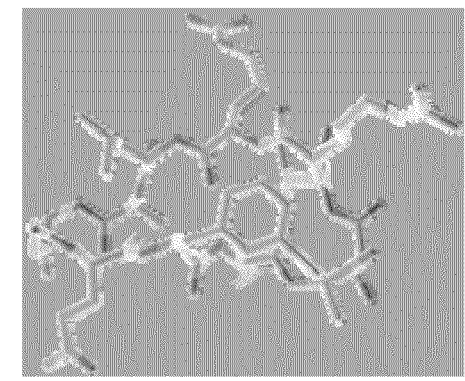
26
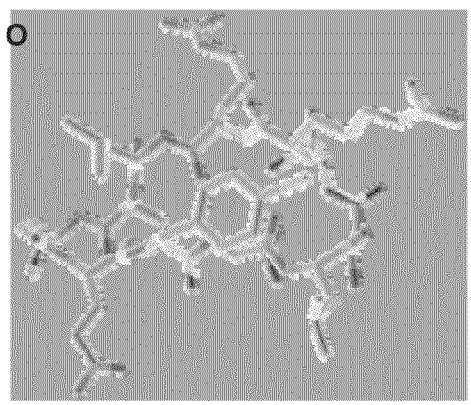
27
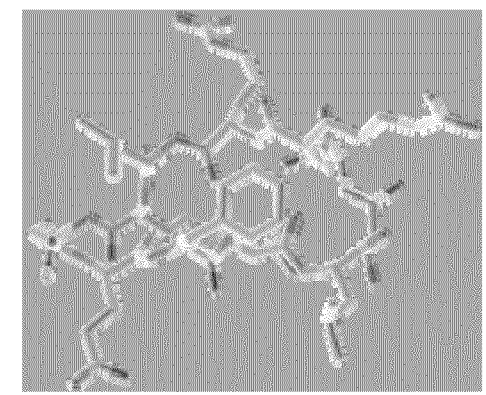
28
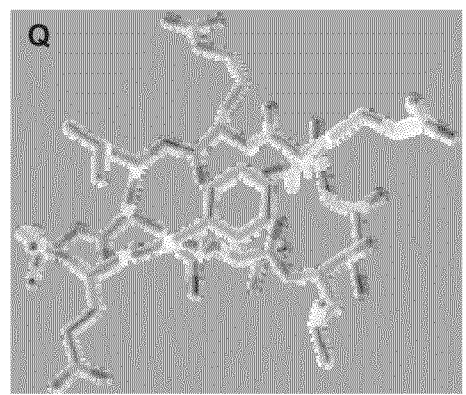
29
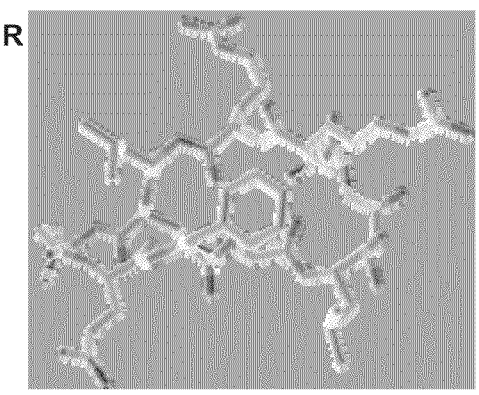
30

Figure 31

| SEQ ID NO: | 5 | 6 | 7 | 8 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| a, b, c (Å) | 64.33, 82.84, 212.32 | 64.20, 82.50, 212.49 | 64.02, 82.83, 212.10 | 64.28, 83.25, 212.30 |
| $\alpha, \beta, \gamma$ (°) | 90.0, 90.0, 90.0 | 90.0, 90.0, 90.0 | 90.0, 90.0, 90.0 | 90.0, 90.0, 90.0 |
| Resolution (Å) | 30.00-2.24 (2.45-2.24) | 32.99-2.53 (2.60-2.53) | 34.36-2.48 (2.54-2.48) | 33.19–2.48 (2.54-2.48) |
| $R_{mrgd-F}$ | 0.070 (0.281) | 0.066 (0.334) | 0.065 (0.312) | 0.072 (0.331) |
| $I/\sigma(I)$ | 19.05 (5.92) | 24.74 (5.21) | 24.88 (4.97) | 23.52 (4.68) |
| Completeness (%) | 99.1 (99.1) | 97.6 (91.3) | 99.4 (92.6) | 99.1 (90.3) |
| Redundancy | 5.2 (5.4) | 4.9 (4.5) | 6.19 (4.27) | 4.61 (3.16) |
| Refinement | | | | |
| Resolution (Å) | 2.24 | 2.53 | 2.48 | 2.48 |
| No. reflections | 55,026 | 37,650 | 40,641 | 41,098 |
| $R_{work}/R_{free}$ | 18.0/22.6 | 17.2/23.6 | 17.6/22.0 | 17.4/22.9 |
| No. atoms | | | | |
|   Protein | 6526 | 6514 | 6551 | 6541 |
|   Meditope | 174 | 291 (198)* | 212 | 218 |
|   Water | 507 | 392 | 511 | 469 |
| B-factors | | | | |
|   Protein | | | | |
|     Fab | 38.16 | 27.79 | 25.74 | 25.23 |
|     Meditope | 49.08 | 43.40 (27.51)* | 31.78 | 31.52 |
|     Water | 41.78 | 28.05 | 28.32 | 29.65 |
| r.m.s.d | | | | |
|   Bond lengths (Å) | 0.007 | 0.005 | 0.007 | 0.008 |
|   Bond angles (°) | 1.093 | 0.903 | 1.091 | 1.106 |
| Ramachandran favored/allowed/disallowed | 96.9/3.1/0.0 | 96.8/3.2/0.0 | 97.6/2.4/0.0 | 97.2/2.7/0.1 |

* 3 meditopes in asymmetric unit. Data in parenthesis refer to the meditopes in the meditope binding pocket characteristic for the WT meditope

Figure 31 (cont.)

| SEQ ID NO: | 12 | 13 | 14 | 15 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| $a, b, c$ (Å) | 64.24, 83.14, 211.94 | 64.30, 83.39, 212.73 | 64.46, 83.21, 212.44 | 64.10, 83.16, 212.32 |
| $\alpha, \beta, \gamma$ (°) | 90.0, 90.0, 90.0 | 90.0, 90.0, 90.0 | 90.0, 90.0, 90.0 | 90.0, 90.0, 90.0 |
| Resolution (Å) | 33.15-2.48 (2.55-2.48) | 33.23-2.49 (2.55-2.49) | 34.96-2.62 (2.69-2.62) | 33.14-2.55 (2.62-2.55) |
| $R_{mrgd-F}$ | 0.044 (0.153) | 0.056 (0.219) | 0.125 (0.470) | 0.094 (0.374) |
| $I/\sigma(I)$ | 25.24 (9.23) | 19.83 (6.03) | 15.21 (3.87) | 19.13 (4.60) |
| Completeness (%) | 95.1 (72.3) | 99.6 (95.4) | 98.6 (97.7) | 99.4 (94.1) |
| Redundancy | 5.2 (4.6) | 5.0 (3.66) | 4.95 (5.05) | 4.33 (3.96) |
| Refinement | | | | |
| Resolution (Å) | 2.48 | 2.49 | 2.62 | 2.55 |
| No. reflections | 39,080 | 40,816 | 34,738 | 37701 |
| $R_{work}/R_{free}$ | 17.9/22.6 | 17.1/22.3 | 18.4/23.5 | 17.8/22.5 |
| No. atoms | | | | |
| Protein | 6554 | 6525 | 6529 | 6517 |
| Meditope | 208 | 198 | 174 | 190 |
| Water | 493 | 511 | 380 | 404 |
| B-factors | | | | |
| Protein | | | | |
| Fab | 24.08 | 24.69 | 25.47 | 25.98 |
| Meditope | 27.64 | 30.40 | 26.45 | 26.64 |
| Water | 29.37 | 29.15 | 28.75 | 28.08 |
| r.m.s.d | | | | |
| Bond lengths (Å) | 0.003 | 0.007 | 0.002 | 0.008 |
| Bond angles (°) | 0.742 | 1.103 | 0.618 | 1.122 |
| Ramachandran favored/allowed/disallowed | 96.9/3.1/0.0 | 97.1/2.9/0.0 | 96.3/3.7/0.0 | 96.5/3.4/0.1 |

Figure 31 (cont.)

| SEQ ID NO: | 21 | 22 | 23 | 24 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| a, b, c (Å) | 64.28, 82.64, 212.50 | 64.16, 82.46, 212.05 | 64.18, 82.66, 211.91 | 63.97, 82.50, 211.88 |
| $\alpha, \beta, \gamma$ (°) | 90.0, 90.0, 90.0 | 90.0, 90.0, 90.0 | 90.0, 90.0, 90.0 | 90.0, 90.0, 90.0 |
| Resolution (Å) | 30.00-2.55 (2.62-2.55) | 32.51–2.49 (2.55-2.49) | 33.02-2.50 (2.56-2.50) | 32.95-2.50 (2.62-2.55) |
| $R_{mrgd-F}$ | 0.085 (0.365) | 0.039 (0.163) | 0.047 (0.177) | 0.094 (0.405) |
| $I/\sigma(I)$ | 20.27 (4.54) | 31.38 (9.58) | 30.78 (9.25) | 17.76 (3.68) |
| Completeness (%) | 96.7 (91.5) | 99.6 (96.1) | 99.8 (99.0) | 99.0 (90.1) |
| Redundancy | 5.1 (5.1) | 5.01 (3.61) | 6.02 (4.70) | 4.00 (3.70) |
| Refinement | | | | |
| Resolution (Å) | 2.55 | 2.49 | 2.50 | 2.55 |
| No. reflections | 36,560 | 40,266 | 39,848 | 37,028 |
| $R_{work}/R_{free}$ | 18.7/22.7 | 16.9/22.0 | 16.9/22.5 | 16.9/21.4 |
| No. atoms | | | | |
| Protein | 6545 | 6509 | 6507 | 6555 |
| Meditope | 188 | 174 | 182 | 190 |
| Water | 332 | 471 | 503 | 285 |
| B-factors | | | | |
| Protein | | | | |
| Fab | 27.94 | 25.70 | 21.62 | 32.02 |
| Meditope | 29.73 | 53.33 | 40.13 | 38.42 |
| Water | 29.40 | 31.55 | 27.78 | 33.79 |
| r.m.s.d | | | | |
| Bond lengths (Å) | 0.002 | 0.003 | 0.004 | 0.005 |
| Bond angles (°) | 0.631 | 0.771 | 0.876 | 0.904 |
| Ramachandran favored/allowed/disallowed | 96.2/3.8/0.0 | 97.2/2.8/0.0 | 97.3/2.7/0.0 | 96.4/3.6/0.0 |

Figure 31 (cont.)

| SEQ ID NO: | 25 | 26 | 27 | 28 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| a, b, c (Å) | 64.01, 82.21, 211.90 | 64.04, 82.51, 211.54 | 64.05, 83.16, 212.26 | 64.14, 83.19, 212.46 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 34.14-2.51 (2.58-2.51) | 34.22–2.48 (2.55-2.48) | 33.13–2.50 (2.56-2.50) | 33.16-2.48 (2.55-2.48) |
| $R_{mrgd-F}$ | 0.046 (0.238) | 0.039 (0.144) | 0.084 (0.375) | 0.054 (0.186) |
| $I/\sigma(I)$ | 25.22 (6.50) | 30.13 (8.86) | 20.51 (4.31) | 29.15 (8.34) |
| Completeness (%) | 98.5 (92.3) | 99.4 (92.5) | 99.2 (92.2) | 99.3 (93.2) |
| Redundancy | 4.12 (3.52) | 5.77 (4.14) | 6.26 (4.94) | 5.79 (4.10) |
| Refinement | | | | |
| Resolution (Å) | 2.51 | 2.48 | 2.50 | 2.48 |
| No. reflections | 38,565 | 40,290 | 39,826 | 40,872 |
| $R_{work}/R_{free}$ | 19.0/23.9 | 17.9/23.5 | 19.1/24.0 | 18.1/23.3 |
| No. atoms | | | | |
| Protein | 6528 | 6535 | 6524 | 6539 |
| Meditope | 218 | 187 | 190 | 192 |
| Water | 338 | 454 | 361 | 485 |
| B-factors | | | | |
| Protein | | | | |
| Fab | 34.24 | 26.67 | 26.19 | 19.15 |
| Meditope | 47.05 | 48.78 | 33.05 | 26.02 |
| Water | 32.96 | 31.14 | 28.90 | 24.13 |
| r.m.s.d | | | | |
| Bond lengths (Å) | 0.003 | 0.008 | 0.004 | 0.003 |
| Bond angles (°) | 0.749 | 1.120 | 0.822 | 0.760 |
| Ramachandran favored/allowed/disallowed | 96.4/3.5/0.1 | 96.0/4.0/0.0 | 96.6/3.4/0.0 | 96.8/3.1/0.1 |

Figure 31 (cont.)

| SEQ ID NO: | 29 | 30 |
|---|---|---|
| Data Collection | | |
| Space group | $P2_12_12_1$ | $P2_12_12_1$ |
| Cell dimensions | | |
|    a, b, c (Å) | 64.21, 83.04, 212.26 | 64.34, 82.57, 212.05 |
|    α, β, γ (°) | 90.0, 90.0, 90.0 | 90.0, 90.0, 90.0 |
| Resolution (Å) | 34.40-2.48 (2.54-2.48) | 34.29-2.48 (2.54-2.48) |
| $R_{mrgd-F}$ | 0.051 (0.184) | 0.035 (0.147) |
| I/σ(I) | 30.80 (7.93) | 38.15 (11.37) |
| Completeness (%) | 99.4 (93.6) | 98.2 (91.1) |
| Redundancy | 5.40 (3.86) | 6.17 (4.25) |
| Refinement | | |
| Resolution (Å) | 2.48 | 2.48 |
| No. reflections | 40,869 | 40,195 |
| $R_{work}/R_{free}$ | 17.8/22.4 | 18.6/23.8 |
| No. atoms | | |
|   Protein | 6499 | 6539 |
|   Meditope | 192 | 192 |
|   Water | 466 | 475 |
| *B*-factors | | |
|   Protein | | |
|     Fab | 20.04 | 20.24 |
|     Meditope | 26.61 | 27.05 |
|   Water | 24.30 | 24.57 |
| r.m.s.d | | |
|   Bond lengths (Å) | 0.007 | 0.007 |
|   Bond angles (°) | 1.071 | 1.125 |
| Ramachandran | | |
| favored/allowed/disallowed | 97.0/2.9/0.1 | 96.9/3.0/0.1 |

Figure 34
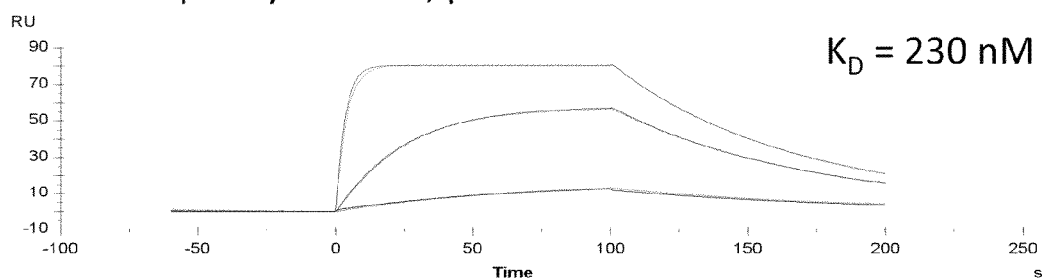
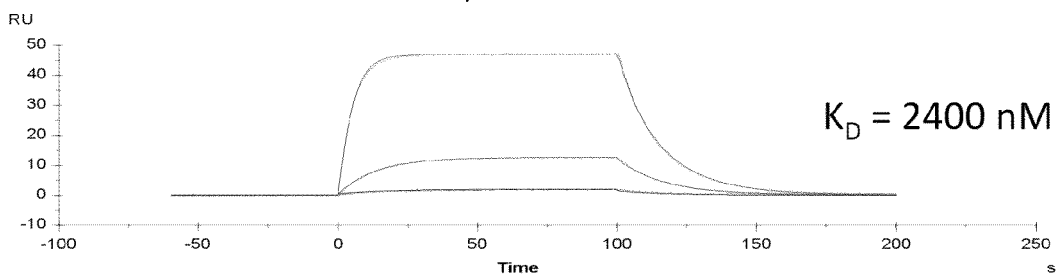

MEDITOPES AND RELATED MEDITOPE-MONOCLONAL ANTIBODY DELIVERY SYSTEMS, SYNTHESIS AND THERAPEUTIC USES THEREOF

PRIORITY CLAIM

This application claims the benefit of U.S. Provisional Application Ser. No. 61/391,558 filed Oct. 8, 2010, which is incorporated herein by reference in its entirety.

This invention was made with Government support of NCI Comprehensive Cancer Center Grant No. CA0335752-28. The government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 706122000100SeqList.txt, date recorded: Aug. 19, 2013, size: 19,183 bytes).

BACKGROUND

Cancers avoid immune surveillance by actively suppressing the immune system. One method envisioned for counteracting this immunosuppression is through vaccination using epitopes of antigens that are either uniquely expressed or over-expressed by the tumor cells. For example, monoclonal antibodies (mAbs) that block signaling pathways, sequester growth factor and/or induce an immune response have been successfully implemented in the clinic to treat cancer and other diseases. Due to their favorable properties and clinical success, mAbs have been and continue to be the subject of intense protein engineering efforts. These efforts have yielded bispecific mAbs for improved targeting; single chain Fab variable fragments (scFvs), diabodies, and minibodies for better tumor penetration and blood clearance; and modified Fcs (through mutation or glycosylation) to alter immunostimulation or improve pharmacokinetic/pharmacodynamic properties. Likewise, mAbs have been reengineered to permit the site-specific conjugation of small molecules for improved delivery (e.g., ThioMABs) or to irreversibly bind to their antigen (e.g., infinite affinity mAbs). MAbs have also been developed to improve the circulation and presentation of bioactive peptides and other biologics (e.g., CovXbodies). Hetero-multimeric scFvs or scFvs or mAbs fused to avidin have also been developed for pre-targeted therapy and to improve the detection limits for tumor imaging.

Although mAbs can be effective and have some advantages over small molecule approaches, limitations such as adverse side effects due to off-target interactions or collateral damage due to long circulation times of radionuclide-conjugated mAbs indicates that there remains considerable room to improve their efficacy, including improved targeting and synergy. Therefore, enhancement of antibody and small molecule therapeutic efficacy would be useful and desired in the treatment of cancer and other diseases.

SUMMARY

Antibody binding peptides C-QFDLSTRRLK-C (cQFD; SEQ ID NO:1) and C-QYNLSSRALK-C (cQYN; SEQ ID NO:2) were shown to have novel mAb binding properties. Specifically, cQFD and cQYN, which are also called "meditopes," were shown to bind to a region of the Fab framework of the anti-EGFR mAb cetuximab and not to bind the complementarity determining regions (CDRs) that bind antigen. The binding region on the Fab framework is distinct from other framework-binding antigens, such as the superantigens Staphylococcal protein A (SpA) (Graille et al., 2000) and *Peptostreptococcus magnus* protein L (PpL) (Graille et al., 2001), and was previously unknown. Accordingly, a first embodiment is a framework binding interface comprising a framework region of a unique murine-human antibody or functional fragment thereof that binds a cyclic meditope having the sequence CQFDLSTRRLKC (SEQ ID NO:1) or CQYNLSSRALKC (SEQ ID NO:2).

Characterization of the meditopes by surface plasmon resonance indicated that cQFD and cQYN bind to Fab with dissociation constants of between approximately 0.70-0.95 and 2-5 μM, respectively. Point mutations designed to disrupt specific interactions further support the structural model. FACS analysis revealed that high concentrations of the cQFD meditope (60 μM) produced negligible differences in the ability of cetuximab to bind to MDA-MB-468 cells, which over-express the EGFR receptor. Thus, meditope binding does not affect antigen binding. In addition, the meditopes were conjugated with a fluorescent group and shown to bind to MDA-MB-468 cells pretreated with cetuximab, but not to MDA-MB-468 cells pretreated with the murine anti-EGFR antibody, M425 (FIG. 4C). Collectively, these data define a meditope binding interface within the Fab framework and demonstrate that the meditope binding does not inhibit antigen binding (e.g., does not act as an allosteric regulator).

In another embodiment, meditopes (e.g., cQYN or cQFD) or variants thereof having the novel binding properties described above may be used to add functionality to therapeutic monoclonal antibodies ("mAbs"). In a further embodiment, the meditopes described herein may be exploited to affect the efficacy of therapeutic substances such as monoclonal antibodies and functional fragments thereof or other substances such as small molecules. In yet another embodiment, tags or detectable labels may be attached to the meditopes for identification of certain types of cells or tissues for diagnostic or therapeutic use.

In a separate embodiment, a meditope contains a cysteine that covalently binds to a cysteine in the Fab at the meditope binding site. The meditope is conjugated to any substance, molecule or compound, which may be therapeutic molecule, such as a small molecule diagnostic molecule, such as a marker. The "Cys meditope" directs the conjugate to the IgG and binds via a covalent linkage.

BRIEF DESCRIPTION OF THE DRAWINGS

FIG. 1A: The complex of cetuximab Fab (light chain denoted by $V_L$ and $C_L$, heavy chain denoted by $V_H$ and $C_H$) and cyclic CQFDLSTRRLKC (depicted within the shaded area and labeled with the word "meditope") (SEQ ID NO:1) indicates that the meditope binds to an interface of the Fab framework, which is distinct from the CDR loops of cetuximab. FIG. 1B shows the stick representation of the cQFD meditope and FIG. 1C shows the stick representation of the cQYN meditope. The N- and C-terminal cysteines are solvent exposed and display high thermal factors.

FIG. 2A shows the corresponding residues for the phage 'negative' selection, ch14.18, and the humanized trastuzumab that make contact with the meditope.

Sequences shown include QRTNGS (SEQ ID NO: 41); IADYY (SEQ ID NO: 42); AGTKLE (SEQ ID NO: 43); QKPGQS (SEQ ID NO: 44); LGVYF (SEQ ID NO: 45); AGTKLE (SEQ ID NO: 46);QKPGKA (SEQ ID NO: 47); FATYY (SEQ ID NO: 48); QGTKVE (SEQ ID NO: 49); QSPGKG (SEQ ID NO: 50); QGTL (SEQ ID NO: 51); QNIGKS (SEQ ID NO: 52); QGTS (SEQ ID NO: 53); QAPGKG (SEQ ID NO: 54); QGTL (SEQ ID NO: 51). FIG. 2B, top panel, shows a stereoview of Arg9 of the cQFD meditope that occupies a distinct pocket encoded by the murine sequence of Cetuximab (foreground). Trastuzumab Fab (1 N8Z.pdb; background) (Cho et al., 2003) is superimposed. There is a salt bridge from Asp85 to the guanidinium group of the meditope Arg9 and the backbone amide of Leu10. FIG. 2B, bottom panel, graphically represents the superposition of the Fab fragments indicating subtle effects due the F to Y in the meditope. Specifically, the hydrophobic groups, F/Y3 L5, and L10 are nearly identically positioned, but the hydroxyl group of Y5 in the cQYN meditope prevents R8 from interacting with the Q111 backbone, as observed in the cQFD meditope ("steric clash"). This rearrangement also results in a concomitant change in the backbone residues of the β-turn ("backbone rotation").

FIG. 4 illustrates that the present meditopes do not bind to the CDRs as was previously hypothesized. FIG. 4A demonstrates a 2.0 Å crystal structure, wherein the meditope binds to middle 'hole' of the cetuximab Fab. The antigen, EGFR domain III, binds at the complementarity determining regions at a significant distance from the meditope binding site. FIG. 4B shows gel results on the left-hand side and related size exclusion chromatography results on the right-hand side. Size exclusion experiments of the individual components, Fab, EGFR domain III, and SMT-cQFD meditope, as well as an admixture of all three, indicate the formation of a heterotrimeric complex and coelute. The non-reducing SDS-PAGE gel shows the fraction that eluted first, indicating the presence of all three components within the new peak (the left-most peak for "complex," shaded light gray) observed from the admixture. FIG. 4C shows the results of a FACS analysis, indicating that the meditope binds to EGFR positive MD-MBA-468 cells only in the presence of cetuximab (arrows). The meditope alone or the meditope in the presence of M425, a murine EGFR antibody, does not bind. FIGS. 4D and 4E show results of surface plasmon resonance experiments using a sensor chip coupled with a cetuximab scFv. The experiments indicate that saturation of the scFv could not be achieved at concentrations as high as 100 µM of the cQFD meditope. The same experiments using the cetuximab Fab coupled sensor chip indicate full saturation. The dissociation constant from this experiment is 660 nM. Control SPR experiments show that the cetuximab scFv readily binds soluble EGFR domain III fragment, indicating that the CDR loops are functional.

FIG. 13 shows biophysical data obtained for the meditopes. FIG. 13B shows a representative binding isotherm of the meditope (SEQ ID NO:1) and Fab (top) and integration (bottom).

FIG. 22 shows the nucleic acid sequence (SEQ ID NO:3) and the corresponding amino acid sequence (SEQ ID NO:4) for a meditope-Fc tethering agent according to some embodiments.

FIG. 27 shows five lead compounds identified from the fluorescent polarization screen.

FIG. 30 shows stick structures for eighteen modified meditopes, corresponding to SEQ ID NO:5 (A), SEQ ID NO:6 (B), SEQ ID NO:7 (C), SEQ ID NO:8 (D), SEQ ID NO:12 (E), SEQ ID NO:13 (F), SEQ ID NO:14 (G), SEQ ID NO:15 (H), SEQ ID NO:21 (I), SEQ ID NO:22 (J), SEQ ID NO:23 (K), SEQ ID NO:24 (L), SEQ ID NO:25 (M), SEQ ID NO:26 (N), SEQ ID NO:27 (O), SEQ ID NO:28 (P), SEQ ID NO:29 (Q) and SEQ ID NO:30 (R). The sequence of these structures is shown in Tables 1 and 2.

FIG. 31 is a table showing the X-ray diffraction data for the structures shown in FIG. 30.

FIG. 32A shows that only the meditope-Fc, and not the monomeric meditope, can inhibit cell growth when combined with cetuximab. FIG. 32B shows that the meditope-Fc enhances the cell-killing capacity of cetuximab.

FIG. 34 shows representative surface plasmon resonance studies of meditope variants. Top trace—Based on the structural information of the Phe3His mutation in the meditope, a new meditope was synthesized with 3,3'-biphenylalanine at position 3. A significant improvement in the binding affinity for cetuximab was observed, ~4 fold, as observed by surface plasmon resonance. Bottom trace—aminohexanoic acid was used to replace the disulfide bridge of the original meditope. While the binding affinity was decreased, these data indicate that modifications can be made to the meditope to address potential issues with pharmacokinetics, pharmacodynamics and toxicity in animal and human studies. It is noted that this combination can be combined with unnatural amino acids at other positions within the meditope.

DETAILED DESCRIPTION

Figure 1:
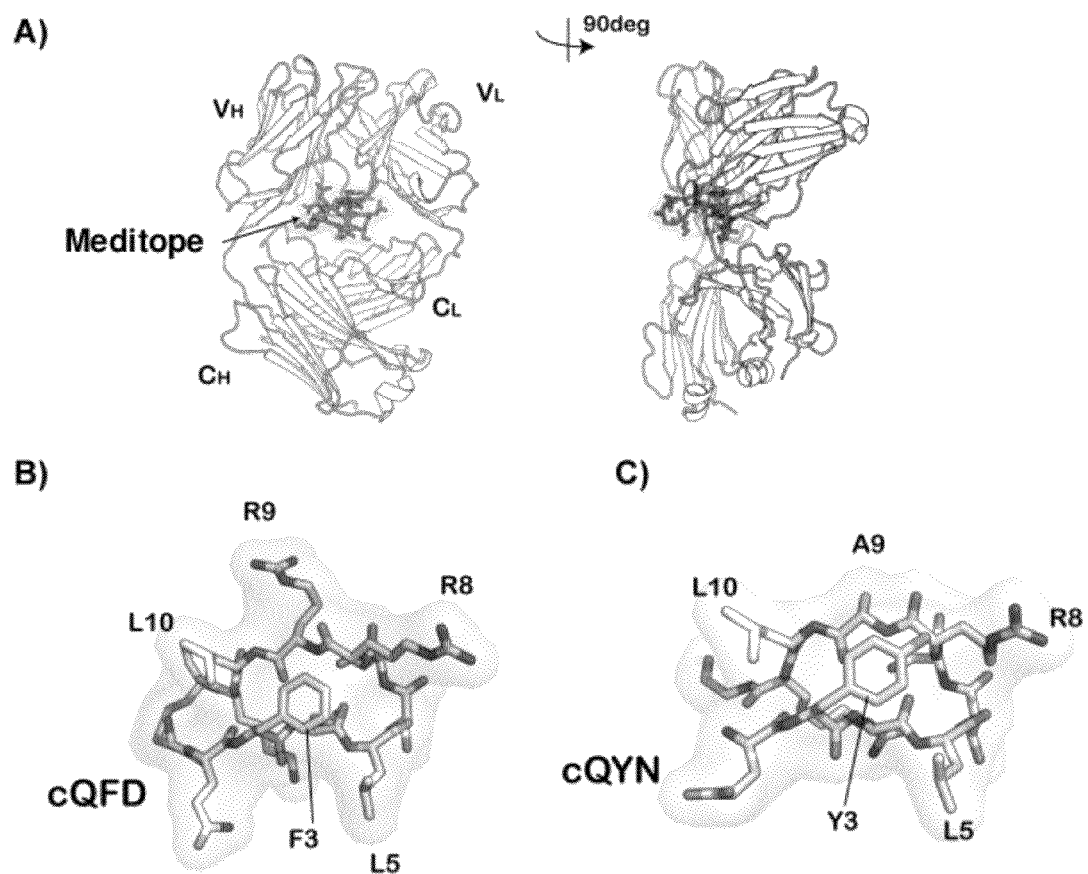
FIG. 1 shows meditope peptides binding framework loops of cetuximab.

An antibody delivery system that selectively delivers therapeutic or imaging agents to a target tissue, and methods for their use are provided herein. The antibody delivery system may include an antibody framework binding interface ("framework binding interface" or "binding interface") bound to an antibody binding molecule (or "meditope") to form an antibody-meditope complex. The antibody-meditope complex may be further conjugated to one or more additional antibody-meditope complexes, therapeutic agents, imaging agents or a combination thereof for use in methods described further below.

According to some embodiments, an antibody framework binding interface that can bind a meditope is formed by a framework region, not by a complementarity determining region (CDR), of an antibody or functional fragment thereof. An "antibody or functional fragment thereof" as used herein refers to an immunoglobulin molecule that specifically binds to, or is immunologically reactive with a particular antigen or epitope, and includes both polyclonal and monoclonal antibodies. The term "antibody" includes genetically engineered or otherwise modified forms of immunoglobulins, such as intrabodies, peptibodies, chimeric antibodies, fully human antibodies, humanized antibodies, meditope-enabled antibodies and heteroconjugate antibodies (e.g., bispecific antibodies, diabodies, triabodies, tetrabodies, tandem di-scFv, tandem tri-scFv). The term "functional antibody fragment" includes antigen binding fragments of antibodies including, but not limited to, fragment antigen binding (Fab) fragment, F(ab')$_2$ fragments, Fab' fragments, Fv fragments, recombinant IgG (rIgG) fragments, single chain variable fragments (scFv) and single domain antibodies (e.g., sdAb, sdFv, nanobody) fragments.

According to some embodiments, the binding interface may be exploited or optimized to enhance binding and imaging of antibodies or functional fragments thereof. In a separate embodiment, a meditope may contain a cysteine residue that binds to an engineered cysteine in the Fab at the meditope binding site (e.g., ThioMAbs). The meditope is thereby conjugated to any diagnostic and/or therapeutic substance, molecule or compound. For example, the substance may be a small molecule diagnostic molecule, such as a marker. The "Cys meditope" directs the conjugate to the IgG and binds via a covalent linkage. Alternatively, the meditope may be conjugated to the Fab to one or more unnatural amino acids that are incorporated into the meditope binding site. Examples of linkages that may be made with unnatural amino acids include (i) stable hydrazone and oxime linkages by incorporation of p-acetylphenylalanine, m-acetylphenylalanine, p-(3-oxobutaboyl)-1-phenylalanin, and p-(2-amino-3-hydroxyethyl)phenylalanine, (ii) thiol reactive by incorporating phenylselenidylalanine, (iii) a UV crosslinker containing benzophenone by incorporating p-benzoyl-1-phenylalanine, (iv) amine reactive by incorporating p-isopropylthiocarbonryl-phenylalanine or p-ethylthiocarbonyl-phenylalanine, (v) azide alkyne Huisgen cycloaddition by incorporating p-propargyloxyphenylalanine or p-azidophenylalanine or any other suitable unnatural amino acid known in the art. In one embodiment, the meditope may direct a reactive group to an unnatural amino acid incorporated into the Fab, suchs as p-acetylphenylalanine.

In addition, the meditope framework binding interface can be grafted onto other mAbs to generate a meditope-enabled mAb. Because the meditope binding site can be grafted onto other mAbs, the binding interface represents a broadly useful platform technology that may be used not just with cetuximab for EGFR targeted conditions, but with any monoclonal antibody. The term "meditope-enabled" antibody, monoclonal antibody or therapeutic antibody refers to any antibody that is able to bind a meditope at its framework binding interface, including cetuximab. Thus, the platform may be expanded for use in treatment, diagnosis or imaging of any cancer, disease or other condition that may be treated or targeted using a therapeutic antibody, including, but not limited to, leukemia and lymphomas (which can be treated or imaged using, e.g., alemtuzumab, bectumumab, gemtuzumab, FBTA05, ibritumomab tiuzetan, ofatumumab, rituximab, tositumomab), breast cancer (which can be treated or imaged using, e.g., trastuzumab, adecatumumab, etrumaxomab) prostate cancer (which can be treated or imaged using, e.g., adecatumumab, capromab pendetide, etaracizumab), colorectal cancer (which can be treated or imaged using, e.g., labetuzumab, panitumumab, altumumab pentetate, votumumab), gastrointestinal cancers (which can be treated or imaged using, e.g., arcitumumab, catumaxomab), ovarian cancer (which can be treated or imaged using, e.g., abagovomab, catumaxomab, etaracizumab, igovomab, oregovomab), lung cancer (which can be treated or imaged using, e.g., anatumumab mafenatox), pancreatic cancer (which can be treated or imaged using, e.g., clivatuzumab tetraxetan), renal cancer (which can be treated or imaged using, e.g., girentuximab), melanoma cancer (which can be treated or imaged using, etaracizumab, ipilimumab, TRBS07), glioma (which can be treated or imaged using, e.g., nimotuzumab), bone metastases (which can be treated or imaged using, e.g., denosumab), head and neck cancer (which can be treated or imaged using, e.g., zalutumumab), cardiovascular disease (which can be treated or imaged using, e.g., abciximab), autoimmune disorders (which can be treated or imaged using, e.g., adalimumab, infliximab), rheumatoid arthritis (which can be treated or imaged using, e.g., atlizumab, golimumab, infliximab), transplant rejection (which can be treated or imaged using, e.g., basiliximab, daclizumab, muromonab-CD3), Crohn's disease (which can be treated or imaged using, e.g., certolizumab, fontolizumab, natalizumab, infliximab, visilizumab), hemoglobinuria (which can be treated or imaged using, eculizumab), psoriasis (which can be treated or imaged using, e.g., efalizumab, infliximab, ustekinumab), multiple sclerosis (which can be treated or imaged using, e.g., natalizumab, ustekinumab), asthma (which can be treated or imaged using, e.g., benralizumab, mepolizumab, omalizumab), respiratory syncytial virus (RSV) (which can be treated or imaged using, e.g., palivizumab), macular degeneration (which can be treated or imaged using, e.g., ranibizumab), appendicitis (which can be treated or imaged using, e.g., fanolesomab) and any other condition that may be targeted or treated with an antibody. The above-listed antibodies and related diseases or disorders are examples only and do not limit the platform.

Figure 7:
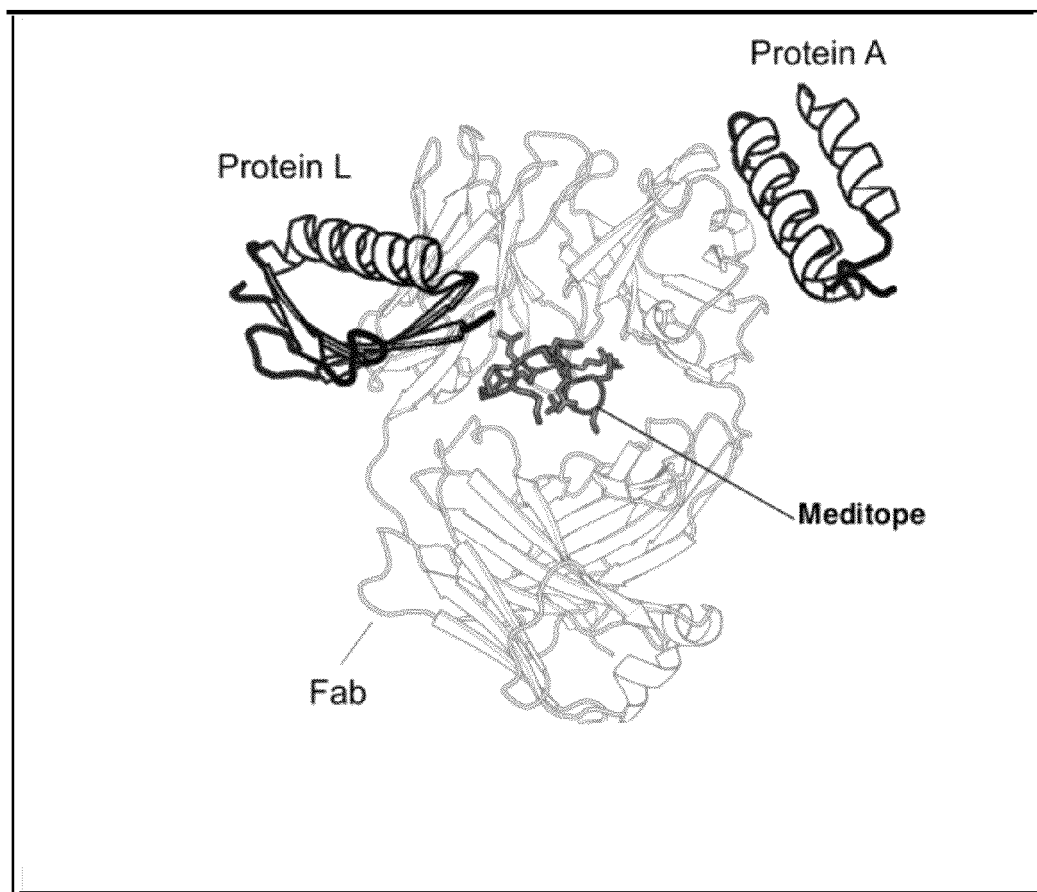
FIG. 7 shows Fab framework binders. Superposition of Fabs bound to meditope, Protein A, and Protein L indicate that each binds to a unique site on the Fab.

In one embodiment, cyclic antibody binding peptides C-QFDLSTRRLK-C (cQFD; SEQ ID NO:1) and C-QYNLSSRALK-C (cQYN; SEQ ID NO:2) can bind the antibody framework binding interface via a non-covalent binding interaction. This non-covalent nature of the binding interaction opens new alternative methods for modifying the framework binding interface, the peptide, or both, expanding the possibilities for generating highly specific meditope variants. In one embodiment, the cQFD and cQYN peptides bind to a framework region of the Fab region of cetuximab, and not to the CDR regions, as shown by diffraction and biophysical data as described below. This binding site is distinct from the binding sites of other framework-binding antigens such as the superantigens Staphylococcal protein A (SpA) and *Peptostreptococcus magnus* protein L (PpL) (FIG. 7). In addition, protein A and Protein L will bind to IgGs present in the patient. Thus the interaction is specific.

Figure 13A:
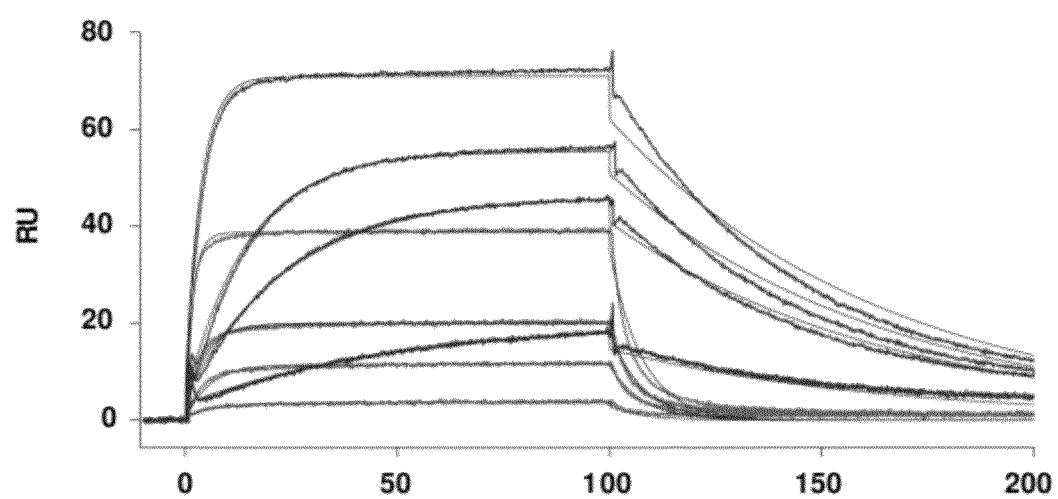
FIG. 13A shows a SPR sensogram of the unmodified meditope cQFD (SEQ ID NO:1) and the QYN meditope (SEQ ID NO:2) using a cetuximab Fab chip.

X-ray crystallographic analysis has revealed that the peptide binds within the Fab cavity, as defined by the heavy and light chains (see FIGS. 1 and 4A), with a binding constant of ~700 nM (see FIGS. 13A-13B). This interaction can be exploited to, among other things, improve the therapeutic efficacy of naked mAbs, enhance targeted delivery of imaging or therapeutic agents, and improve mAb-based imaging methods.

The cQFD and cQYN meditopes bind to a chimeric framework binding region, such as that found in cetuximab. The term "meditope" (a term combining medius+topos, Latin for middle and Greek for place), as used herein refers to an antibody binding peptide, such as the cQFD and cQYN peptides or variants thereof, that bind between the Fab light and heavy chains of an antibody. Other molecules may also bind between the Fab light and heavy chains of an antibody with a framework binding functionality similar to that of a meditope. Such molecules may include, but are not limited to, small molecules, aptamers, nucleic acid molecules, peptibodies and any other substance able to bind the same binding interface as a meditope, The framework binding interface described herein is distinct and distant from the CDR, which binds to the antigen epitope (FIG. 4). Additionally, biochemical and cell-based assays have demonstrated that the cQFD and cQYN cyclic peptides can bind to murine chimeric cetuximab that is pre-bound to EGFR (FIG. 4).

Figure 33:
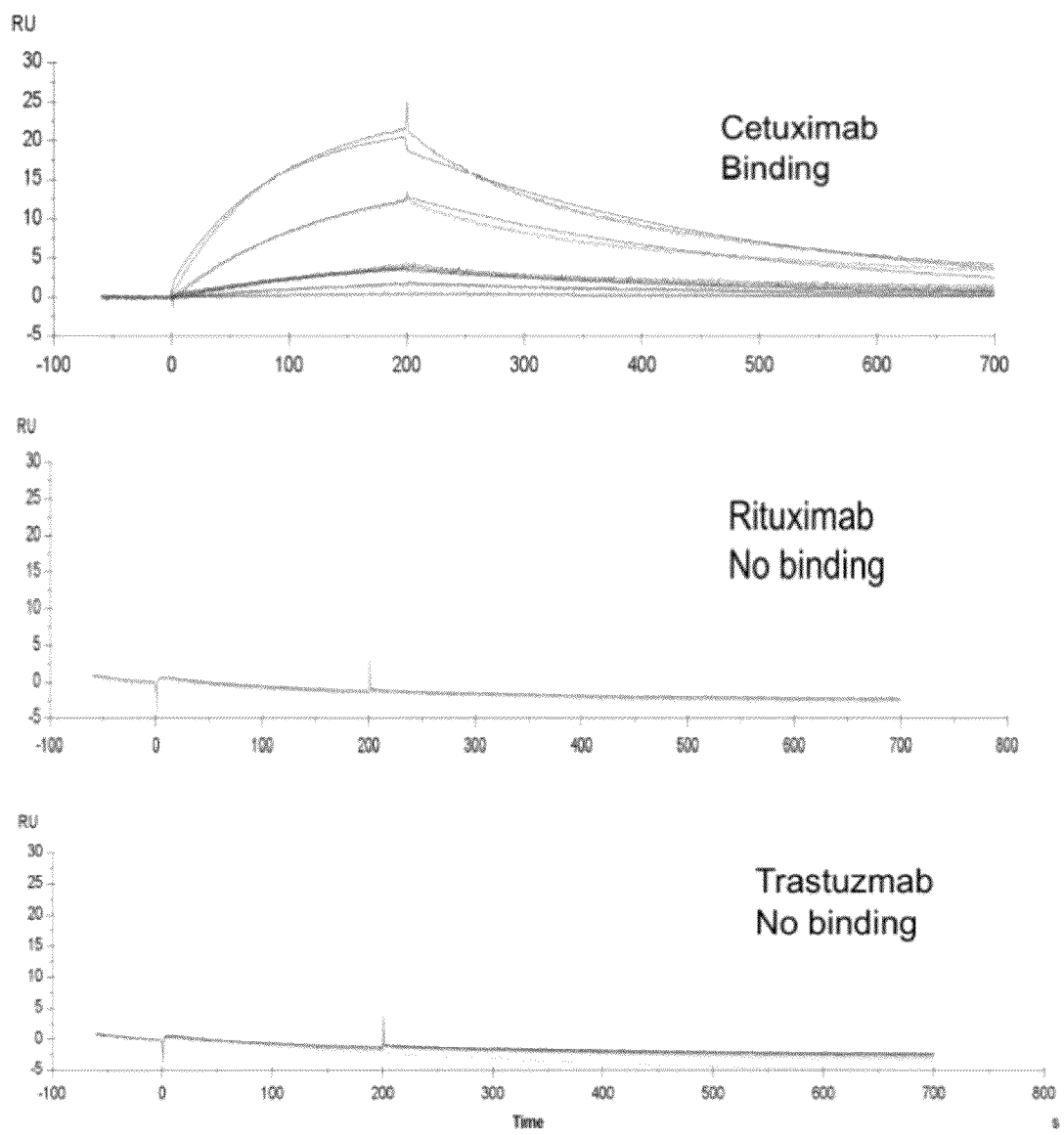
FIG. 33 illustrates that the meditope binds to unique cetuximab framework, but not to human framework or other murine-chimera frameworks. The wildtype meditope was conjugated to a CM5 chip for surface plasmon resonance studies and cetuximab (meditope binding Fab), trastuzumab (fully human framework), and rituximab (murine-human chimeric framework) were tested concentrations 0.01, 0.05, 0.1, 0.5 and 1 uM. Only cetuximab bound to the meditope-conjugated chip. Superposition of the molecular structure of trastuzumab (1 N8Z; Cho et al. 2003) and rituximab (2OSL; Du et al. 2007) Fabs on to the meditope bound cetuximab Fab structure further highlights the uniqueness of the framework. Moreover, this structureal comparison gives a clear indication of which residues originating from the cetuximab Fab contribute to meditope binding and how they can be grafted onto other Fab framework regions.

Cetuximab is a unique murine-human chimera and several interactions between the cQFD and cQYN meditopes and the cetuximab Fab are specific to this murine-human chimeric IgG framework residues as determined by an atomic model described herein. Further, the meditopes fail to bind to human IgG framework (e.g., trastuzumab), indicating this interaction is specific for this murine-chimeric antibody, but not specific for other murine chimeras such as rituximab (FIG. 33). This supports that the Cetuximab framework is highly specific. Superposition of multiple human and murine Fabs onto the cetuximab-cyclic peptide structure indicated that the key interactions between this peptide and murine-human chimeric Fab are absent in both human-only and murine-only IgG structures. Point mutations of key residues within the cyclic peptide reduced its binding affinity for the Fab, further confirming the high specificity and structural model (data not shown). Thus, the interaction appears to be specific to the central cavity of this specific murine-human chimera Fab and the selected meditope. In contrast, PpL and SpA are not murine-specific. PpL binds to ~66% of murine and ~50% of human IgG Kappa light chains and SpA binds 12% of murine and 50% of human variable heavy chains (Graille et al., 2002).

Cetuximab is currently used for the treatment of EGFR-expressing metastatic colorectal cancer and head and neck cancers. Cetuximab recognizes a conformational epitope (e.g., folded EGFR domain III). A comparison of antibodies that recognize small molecule antigens, peptides and protein epitopes show that the interfaces tend to possess different features (Collis et al., 2003). Small molecules tend to be cradled in a small pocket; peptides fit into a linear grove; and proteins contact a large surface. Thus, the peptides that successfully recreate the protein-antibody interaction, as with cetuximab-EGFR, are generally those with the protein antigen having an unfolded domain with a large contacting surface area. For example, trastuzumab recognizes a protein antigen (conformational epitope), but makes contact primarily with a number of geometrically constrained loops (Du et al., 2007; Cho et al., 2003). This type of biological recognition is more compatible with peptide mimics.

The cQFD and cQYN meditopes were originally identified as candidate peptides for binding the CDR region of cetuximab. Phage display libraries have been used to identify peptides that bind the complementarity determining regions (CDRs) of established therapeutic antibodies with the presumption that the peptides would mimic the antigenic epitope to artificially stimulate an immune response to that antigen (Riemer et al., 2004; Riemer et al., 2005; Li et al., 2006). These peptide mimics, also referred to as mimotopes or anti-idiotypes, can be chemically synthesized, eliminating potential biological contamination and reducing cost. Vaccines based on this design, however, have resulted in partial responses, and are often followed by later recurrence of disease without loss of the immune response to tumor antigen (Sharav et al., 2007).

Because the cQFD and cQYN meditopes bind the framework and not the CDR region, said meditopes are not likely candidates for specific cetuximab-like antibody immunogens for use as a vaccine. Although Reimer et al. observed that sera collected from mice immunized with KLH-coupled meditope produced antibodies that bound to A431 cells and block their proliferation (Riemer et al., 2005), the studies described herein show that multiple copies of the meditopes coupled to adjuvant render the vaccine into a promiscuous crosslinker of murine IgGs (akin to a superantigen). In support of this embodiment, similar germ line or B-cell derived framework sequences were observed in the mouse light chain and both mouse and human heavy chains using BLAST. Thus, when tethered to an adjuvant, the meditope peptides may function to activate the B-cell population with conserved framework regions and produce a generalized immune response as opposed to a specific immune response required for a vaccine. The reported ELISA competition assays do not indicate the specific binding site of EGFR nor the degree to which the polyclonal serum was specific for the cetuximab epitope on EGFR (e.g., the report did not indicate whether or not the serum-derived IgG could be blocked by unlabeled cetuximab). The diffraction and biochemical studies do not support using the cQYN or cQFD meditopes as a vaccine in humans.

Additional meditopes that may be used according to the embodiments described herein include any small peptide that binds to an antibody framework binding interface (i.e., between the Fab light and heavy chains) of cetuximab or any other therapeutic antibody. For example, in addition to the cyclic peptides cQFD and cQYN, some embodiments include one or more variants of cQFD and cQYN.

Structural and biophysical methods or modifications may be used in tandem with chemical synthesis to develop meditope variants that have increased or altered affinity (e.g., due to changes in pH, as discussed in the examples below) to cetuximab as compared to the unmodified meditopes, cQFD and cQYN. Furthermore, conjugation of an unmodified meditope or a variant meditope onto a multivalent tethering entity or scaffold may significantly improve the overall affinity and targeting of the multivalent meditope to a meditope-enabled mAb bound to tumor-associated antigen. Modifications to cQFD and cQYN meditopes that may be used to generate meditope variants with high affinity may include, but are not limited to, use of one or more of the following: a head-to tail cyclic lactam peptide, a modification of Arg8, a modification of Phe3, a modification of Leu5 and/or Leu10, and an incorporation of hydratable carbonyl functionality. Each amino acid position may be altered with an unnatural amino acid or chemically conjugated with a fragment. It is shown herein that that Arg9 mutated to cituralline binds to cetuximab. In addition, the amino and carboxy termini can be extended to make additional contact to the Fab. Further, protein L has been added to the N-terminus of the meditope and preliminary data shows that this binds with much higher affinity. Such modifications are discussed further in Examples 4 and 5.

According to the embodiments described herein, the meditope variant peptides may be one or more of the cyclic peptides shown in Tables 1 and 2, which were synthesized with demonstrated binding affinities to cetuxamab. With the exception of SEQ ID NO:1 and SEQ ID NO:2, the sequences represent novel structures. The peptides in Table 1 use a disulfide linkage to connect the C and N terminal of each peptide while the peptides in Table 2 utilize a lactam bridge or method other than disulfide like [3+2] cycloaddition as the connector.

TABLE 1

| SEQ ID NO | Sequence | Modification (underlined) | Linkage method |
|---|---|---|---|
| 1 | C-QFDLSTRRLK-C | original | Disulfide 1-Cys:12-Cys |
| 2 | C-QYNLSSRALK-C | original | Disulfide 1-Cys:12-Cys |
| 5 | C-qFDLSTRRLK-C | q = D-glutamine | Disulfide 1-Cys:12-Cys |
| 6 | C-QYDLSTRRLK-C | Y = Tyrosine | Disulfide 1-Cys:12-Cys |
| 7 | C-QXDLSTRRLK-C | X = β-β-di-phenyl-Ala | Disulfide 1-Cys:12-Cys |
| 8 | C-QFDXSTRRLK-C | X = β-β-di-phenyl-Ala | Disulfide 1-Cys:12-Cys |
| 9 | C-QFDFSTRXLK-C | F = phenylalanine, X = citrulline | Disulfide 1-Cys:12-Cys |
| 10 | C-QFDFSTRRLK-C | F = phenylalanine | Disulfide 1-Cys:12-Cys |
| 11 | C-QFDESTRRLK-C | E = glutamic acid | Disulfide 1-Cys:12-Cys |
| 12 | C-QFDYSTRRLK-C | Y = Tyrosine | Disulfide 1-Cys:12-Cys |
| 13 | C-QFDLSTRRQK-C | Q = glutamine | Disulfide 1-Cys:12-Cys |
| 14 | C-QFDLSTRQLK-C | Q = glutamine | Disulfide 1-Cys:12-Cys |
| 15 | C-QYNLSTARLK-C | Y = Tyrosine; N = asparagine; A = alanine | Disulfide 1-Cys:12-Cys |
| 16 | C-QADLSTRRLK-C | A = alanine | Disulfide 1-Cys:12-Cys |
| 17 | C-QFDASTRRLK-C | A = alanine | Disulfide 1-Cys:12-Cys |
| 18 | C-QFDLSTARLK-C | A = alanine | Disulfide 1-Cys:12-Cys |
| 19 | C-QFDLSTRRAK-C | A = alanine | Disulfide 1-Cys:12-Cys |
| 20 | C-QFDLSTRREK-C | E = glutamic acid | Disulfide 1-Cys:12-Cys |
| 21 | C-QFDLSTRRLK-CGGSK | | Disulfide 1-Cys:12-Cys |

TABLE 2

| SEQ ID NO | Sequence | Modification (underlined) | Linkage method |
|---|---|---|---|
| 22 | G-QFDLSTRRLK-G | G = Glycine | Lactam 1-Gly:12-Gly |
| 23 | G-QHDLSTRRLK-G | H = histidine | Lactam 1-Gly:12-Gly |
| 24 | G-QNDLSTRRLK-G | N = asparagine | Lactam 1-Gly:12-Gly |
| 25 | G-QQDLSTRRLK-G | Q = glutamine | Lactam 1-Gly:12-Gly |
| 26 | G-QXDLSTRRLK-G | X = 2-bromo-L-phenylalanine | Lactam 1-Gly:12-Gly |
| 27 | G-QXDLSTRRLK-G | X = 3-bromo-L-phenylalanine | Lactam 1-Gly:12-Gly |
| 28 | G-QXDLSTRRLK-G | X = 4-bromo-L-phenylalanine | Lactam 1-Gly:12-Gly |
| 29 | G-QFDLSTRXLK-G | X = citrulline | Lactam 1-Gly:12-Gly |
| 30 | G-QFDLSTXXLK-G | X = citrulline | Lactam 1-Gly:12-Gly |
| 31 | G-QFDLSTXRLK-G | X = citrulline | Lactam 1-Gly:12-Gly |
| 32 | Q-FDLSTRRLK-X | X = 7-aminoheptanoic acid | Lactam 1-Gln:11-X |
| 33 | X-QFDLSTRRLK-X | X = β-alanine | Lactam 1-X:12-X |
| 34 | X-QFDLSTRRLK-X' | X = diaminopropionic acid; X' = iso-aspartic acid | Lactam 1-X:12-X' |
| 35 | X-QFDLSTRRLK-X' | X = β-alanine; X' = iso-aspartic acid | Lactam 1-X:12-X' |
| 36 | X-QFDLSTRRLK-X' | X = diaminopropionic acid; X' = β-alanine | Lactam 1-X:12-X' |
| 37 | F-DLSTRRL-K | | Lactam 1-Phe:9-Lys |
| 38 | C-QFDLSTRRLK-C | | Disulfide 1-Cys:12-Cys; Lactam 4-Asp to 11-Lys |
| 39 | Q-YDLSTRRLK-X | Y = Tyrosine, X = 7-aminoheptanoic acid | Lactam 1-Gln:11-X |
| 40 | X-QFDLSTRRLK-X' | X = β-Azidoalanine, X' = propargylglycine | [3 + 2] cycloaddition Azide-1-X:alkyne-12-X' |

In certain embodiments, one or more meditopes, meditope variants, multivalent meditope tethering agents or multivalent meditope variant tethering agents may be conjugated to one or more imaging agents, therapeutically effective agents or compounds in therapeutically effective amounts or both, such that the binding of the meditopes or variants thereof to one or more meditope-enabled antibody with the therapeutically effective compound may treat, prevent, diagnose or monitor a disease or condition. Such conjugation of a high affinity and/or multivalent meditope coupled to meditope-enabled mAbs provides a highly versatile platform technology that will significantly improve mAb based therapeutics and imaging methods to treat and detect disease (see FIG. 8).

In some embodiments, the murine specific cQFD and cQYN meditopes or derivatives thereof may be used to tether two or more antibodies or functional fragments thereof. When used in a tethering method described below, the meditopes may be part of a multivalent tethering agent (also referred to as a "meditope scaffold" or "scaffold") to enhance cancer or tumor therapy and imaging.

A multivalent tethering agent may include two or more cQFD and cQYN meditopes or any of the other novel meditope variants that are coupled through a long linker and biotin to streptavidin to create a multivalent meditope tethering entity. In one embodiment, the multivalent meditope tethering entity is a tetravalent meditope tethering agent. The tetrameric tethering entity is shown by surface plasmon resonance to have enhanced binding to an IgG as compared to the monovalent peptide, which is consistent with a multivalent interaction. The tetravalent meditope also enhances the binding affinity of cetuximab in EGFR positive cells by FACS analysis.

Figure 8:
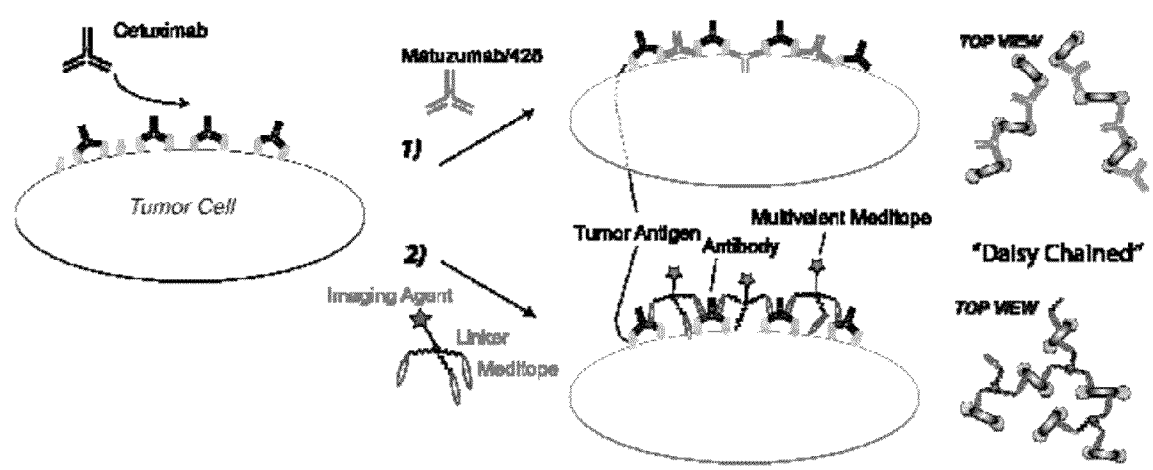
FIG. 8 illustrates one mechanism of action for enhancing tumor therapy. Overexpression of antigen (e.g., ErbB receptor family) on tumor cells binds to bivalent antibodies (left panel) and blocks receptor signaling, alters endocytosis and receptor recycling and/or elicits an immune response. The addition of a multivalent meditope tethers/cross-links the therapeutic mAb and can enhance its therapeutic potential (right). The right panel depicts the daisy-chain linkage expected from a trivalent meditope.

Multivalent meditope scaffolds can be used to scaffold or "daisy-chain" meditope-enabled mAbs bound to tumor associated antigen to enhance ligand antagonism, alter receptor endocytosis, and/or improve an immune response through ADCC/CDC (FIG. 8). Monoclonal antibodies (mAbs) encode two Fab domains coupled to a dimeric Fc. As such, these bivalent IgGs preferentially bind to cells that express antigen at high densities. It has been demonstrated that a second mAb that binds to a unique epitope on the same antigen can cluster the receptors and more effectively kill tumor cells. This clustering can be recapitulated through the use of multivalent meditopes. The use of a multivalent meditope avoids necessity of identifying a second mAb and the associated and significant cost of its development thereof.

The specificity and binding of the meditopes, meditope variants, multivalent meditope tethering agents and multivalent meditope variant tethering agents may be used to deliver therapeutic agents, diagnostic agents (e.g., imaging agents), or a combination of thereof for treatment, diagnosis or imaging a disease or condition when administered in combination with one or more meditope-enabled monoclonal antibodies. Thus, multivalent meditopes can be used for pre-targeted therapy and imaging as described further below by administering a meditope-enabled monoclonal antibody before administering the meditopes, meditope variants, multivalent meditope tethering agents or multivalent meditope variant tethering agents. Further, the use of multivalent meditopes can enhance selectivity and improve tumor detection as has been demonstrated for engineered scFvs or chemically conjugated mAbs, but avoids potential immunogenicity inherent in these non-human constructs.

In some embodiments, a meditope administered in combination with a meditope enabled antibody, an antibody-meditope complex, a multivalent tethering agent administered in combination with a meditope enabled antibody, or a combination thereof may be conjugated to one or more imaging agent. In one aspect, an imaging agent may include, but is not limited to a fluorescent, luminescent, or magnetic protein, peptide or derivatives thereof (e.g., genetically engineered variants). Fluorescent proteins that may be expressed by the mRNA component include green fluorescent protein (GFP), enhanced GFP (EGFP), red, blue, yellow, cyan, and sapphire fluorescent proteins, and reef coral fluorescent protein. Luminescent proteins that may be expressed by the mRNA component include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9.sup.th edition, 2002; and The Handbook—A Guide to Fluorescent Probes and Labeling Technologies, Invitrogen, 10th edition, available at the Invitrogen web site; both of which are hereby incorporated by reference as if fully set forth herein.)

In other aspects, the meditope administered in combination with a meditope enabled antibody, the antibody-meditope complex, the multivalent tethering agent administered in combination with a meditope enabled antibody, or a combination thereof may be further conjugated to or otherwise associated with a non-protein imaging agent or a delivery vehicle such as a nanoparticle, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, it should be noted that some nanoparticles, for example quantum dots and metal nanoparticles (described below) may also be suitable for use as an imaging agent or a therapeutic agent (e.g., using hyperthermal and photodynamic therapies as well as imaging agents through fluorescence and or MRI contrast).

Fluorescent and luminescent substances that may be used as an additional imaging agent in accordance with the embodiments of the disclosure include, but are not limited to, a variety of organic or inorganic small molecules commonly referred to as "dyes," "labels," or "indicators." Examples include fluorescein, rhodamine, acridine dyes, Alexa dyes, and cyanine dyes.

Enzymes that may be used as an additional imaging agent in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

Radioactive substances that may be used as an additional imaging agent in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$S, $^{89}$Zr, $^{94}$TC, $^{94}$TC, $^{99m}$TC, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{226}$AC. Paramagnetic ions that may be used as an additional imaging agent in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the imaging agent is a radioactive metal or paramagnetic ion, the agent may be reacted with another long-tailed reagent having a long tail with one or more chelating groups attached to the long tail for binding these ions. The long tail may be a polymer such as a polylysine, polysaccharide, or other derivatized or derivatizable chain having pendant groups to which may be added for binding to the metals or ions. Examples of chelating groups that may be used according to the disclosure include, but are not limited to, ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups. The chelate is normally linked to the PSMA antibody or functional antibody fragment by a group which enables the formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis.

In some embodiments, a meditope, an antibody-meditope complex, a multivalent tethering agent, or a combination thereof may be conjugated to one or more therapeutic agents.

A "therapeutic agent" as used herein is an atom, molecule, or compound that is useful in the treatment of cancer or other conditions described herein. Examples of therapeutic agents that may be conjugated to an antibody-meditope complex, a multivalent tethering agent, a multivalent tethering agent or a combination thereof include, but are not limited to, drugs, chemotherapeutic agents, therapeutic antibodies and antibody fragments, toxins, radioisotopes, enzymes (e.g., enzymes to cleave prodrugs to a cytotoxic agent at the site of the tumor), nucleases, hormones, immunomodulators, antisense oligonucleotides, RNAi molecules (e.g., siRNA or shRNA), chelators, boron compounds, photoactive agents and dyes. The therapeutic agent may also include a metal, metal alloy, intermetallic or core-shell nanoparticle bound to a chelator that acts as a radiosensitizer to render the targeted cells more sensitive to radiation therapy as compared to healthy cells. Further, the therapeutic agent may include paramagnetic nanoparticles for MRI contrast agents (e.g., magnetite or $Fe_3O_4$) and may be used with other types of therapies (e.g., photodynamic and hyperthermal therapies. And imaging (e.g., fluorescent imaging (Au and CdSe)).

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as therapeutic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Therapeutic antibodies and functional fragments thereof, that may be used as therapeutic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, and trastuzumab and other antibodies associated with specific diseases listed herein.

Toxins that may be used as therapeutic agents in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

Radioisotopes that may be used as therapeutic agents in accordance with the embodiments of the disclosure include, but are not limited to, $^{32}P$, $^{89}Sr$, $^{90}Y$. $^{99m}Tc$, $^{99}Mo$, $^{131}I$, $^{153}Sm$, $^{177}Lu$, $^{186}Re$, $^{213}Bi$, $^{223}Ra$ and $^{225}Ac$.

The meditope-mAb technology allows for a system that may be used to generate an antibody-meditope complex that may be further conjugated to one or more meditope-enabled antibody, a therapeutic agent, an imaging agent or a combination thereof. Thus, a set of meditopes or high affinity meditope variants, each conjugated to a unique cytotoxic or imaging agent, would allow for the co-administration of a desired meditope conjugate and meditope-enabled mAb for treatment. The meditope conjugates are an improvement over the current antibody-drug conjugates, which have drawbacks such as a reduced specificity due to chemical modification or release of payload.

This platform technology has a broad impact on the mAb delivery field and provides useful methods for the treatment and diagnosis of EGFR-positive cancers including colorectal and squamous cell carcinoma head and neck cancers where cetuximab is indicated. Additionally, grafting the framework binding interface onto other therapeutic antibody, allows for the platform technology to be utilized in methods for the treatment and diagnosis of several other cancers, diseases and other conditions as described above.

A method for enhancing the binding affinity of a therapeutic antibody or functional fragment thereof is provided herein. Such a method may include administering to a subject a therapeutically effective amount of a pharmaceutical composition via any suitable route of administration. The pharmaceutical composition may include a meditope or meditope variant in combination with a meditope enabled antibody, a multivalent meditope or meditope variant tethering entity in combination with a meditope enabled antibody, a meditope-enabled therapeutic antibody or functional fragment thereof, a pharmaceutically acceptable carrier, and any combination thereof. The enhanced binding affinity of the multivalent meditope may be attributed to the multivalent cross-linking of IgGs bound to the cell surface. Crosslinking IgGs (through parental murine 425 antibody or using anti-IgG IgM) significantly affects signaling, receptor endocytosis and recycling, and cell death. Thus, multivalent peptides may act synergistically with a therapeutic monoclonal antibody to enhance its therapeutic efficacy.

In some embodiments, the meditope, alone or as part of the tethering entity, may contain a cysteine or other suitable alkylating agent that binds to a Fab cysteine at the binding site, thus creating a cysteine-cysteine interaction. Alternatively, the meditope may bind to the Fab at an unnatural amino acid (e.g., p-acetylphenylalanine). The Cys meditope is conjugated to any substance and directs the conjugate to the IgG.

An antibody-meditope complex may also be used in a method for directing treatment to a particular type of cell or population of cells in a disease or condition that can be targeted by a therapeutic antibody. Such a method of treatment may include administering a therapeutically effective amount of a pharmaceutical composition to a subject having the disease or condition via any suitable route of administration. The pharmaceutical composition may include a meditope or meditope variant in combination with a meditope enabled antibody, a multivalent meditope or meditope variant tethering entity in combination with a meditope enabled antibody, a meditope-enabled therapeutic antibody or functional fragment thereof.

In other embodiments, a method for imaging tumors or other tissues is provided. In such methods, an unmodified therapeutic antibody may be administered to target a tumor or other tissue that overexpress the corresponding antigen. Subsequently, a multivalent meditope tethering entity that is labeled with an imaging agent is administered via any suitable route of administration and will bind the therapeutic antibodies that are bound to the target tumor or tissue. See FIG. 8. Examples of imaging agents include but are not limited to radiolabels (e.g., $^{3}$H, $^{14}$C, $^{35}$S, $^{90}$Y, $^{99m}$Tc, $^{125}$I, $^{131}$I, $^{177}$Lu, $^{166}$Ho, and $^{153}$Sm), metal or magnetic labels (e.g., gold, iron, gadolinium), biotin, chelating agents (e.g., 1,4,7,10-tetraaza-cyclododecane-N,N', N'',N'''-tetraacetic acid ("DOTA")) or any agent described above. In one embodiment, the imaging agent used with the method described herein is DOTA.

There are several advantages over known methods to the imaging or treatment methods described above. First, the bivalent character of a therapeutic monoclonal antibody IgG enhances the selectivity to the tumor. As discussed further below, this enhanced selectivity is lost with the use of scFvs and other minibodies and cannot be made up through enhanced affinity. Second, the mass of the labeled multivalent meditope tethering entity will be below the renal threshold for filtering (less than 60 kD, may be as low as ~10 kD), allowing it to be easily filtered out of the body. In contrast, direct labeling of a therapeutic antibody IgG with an imaging agent or other therapeutic agent is typically avoided because it will circulate for extended periods in the body. Thus, imaging of tumors or other diseased organs is often accomplished using less selective scFvs.

In further embodiments, the cQFD and cQYN meditopes or variants thereof may be used to join two or more therapeutic molecules to form a pharmaceutical compound that may be administered, as part of a pharmaceutical composition, in a therapeutically effective amount to a subject for treatment of cancer, autoimmune disease or other conditions. The two or more therapeutic molecules may include, but are not limited to, functional antibody fragments (e.g., F(ab')$_2$ or Fab fragments), peptides or other small molecules that can target tumor or disease-specific receptors such as those described above. The therapeutic molecules may be two or more of the same therapeutic molecule or alternatively, may be two or more different molecules that target the same tumor or diseased tissue.

In some embodiments, the pharmaceutical compound may include the use of proprietary antibody, or portion thereof, such as a CovX-Body™. For example, the meditopes may be used as a linker to join two or more therapeutic molecules to a binding interface or binding site of a specially designed CovX antibody. A small molecule, peptide or scFv that is associated with a meditope that acts as a CovX-specific linker is recognized by its framework binding interface, which is the active binding site of the CovX antibody. When these components are combined, the resulting bivalent CovX-Body™ possesses the biologic actions of the small molecule, peptide or scFv while also retaining an extended half-life of the antibody.

In addition to the benefits described above with respect to therapeutic monoclonal antibodies, meditopes used as linkers to tether or bind to therapeutic molecules can be synthesized and are more cost effective to produce than monoclonal antibodies. For example, although a number of preclinical/clinical trials are investigating the co-administration of two monoclonal antibodies, the costs of producing and marketing such a therapeutic is likely to be prohibitive.

The scFv (single chain Fab variable fragment) format of the cetuximab Fab binds to the EGFR domain III with a substantially lower affinity than the Fab itself, which is similar to other scFvs of clinical interest. This is attributed, at least in part, to absence of the Fab constant domain that directly affects the orientation, conformational fluctuations of the Fv domains, and possibly, to poor linker design.

Figure 9:
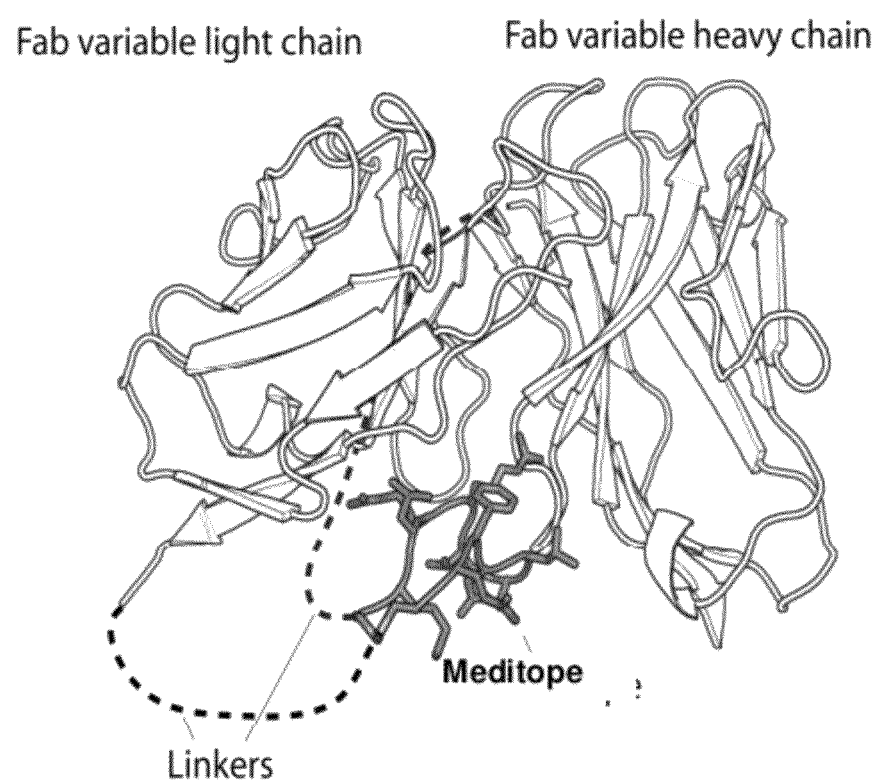
FIG. 9 shows scFv-meditope linker. scFvs are created by fusing the light chain variable domain to the heavy chain variable domain (or vice versa) through a 12-20 amino acid linker (typically {GGGS}$_{3-5}$)(SEQ ID NOs:56-58).

Therefore, in some embodiments, a method for improving the stability and affinity of the scFvs is provided. The method comprises incorporating the peptide meditope in the scFv linker, to stabilize the scFv. This will help to enforce the proper orientation of the variable domains and thus enhance the affinity (FIG. 9).

The embodiments described above can be applied to human or humanized antibodies (e.g., trastuzumab) by replacing one or more of the human framework residues (i.e. generating one or more point mutations) with their corresponding murine residues. The human residues that are replaced by corresponding murine residues are found within the central Fab cavity of the human framework and are therefore not exposed to the immune system (e.g., they should not be antigenic). In addition, antigenicity prediction algorithms may be further used to indicate that the human sequence with the point mutations should not be antigenic.

Figure 2:
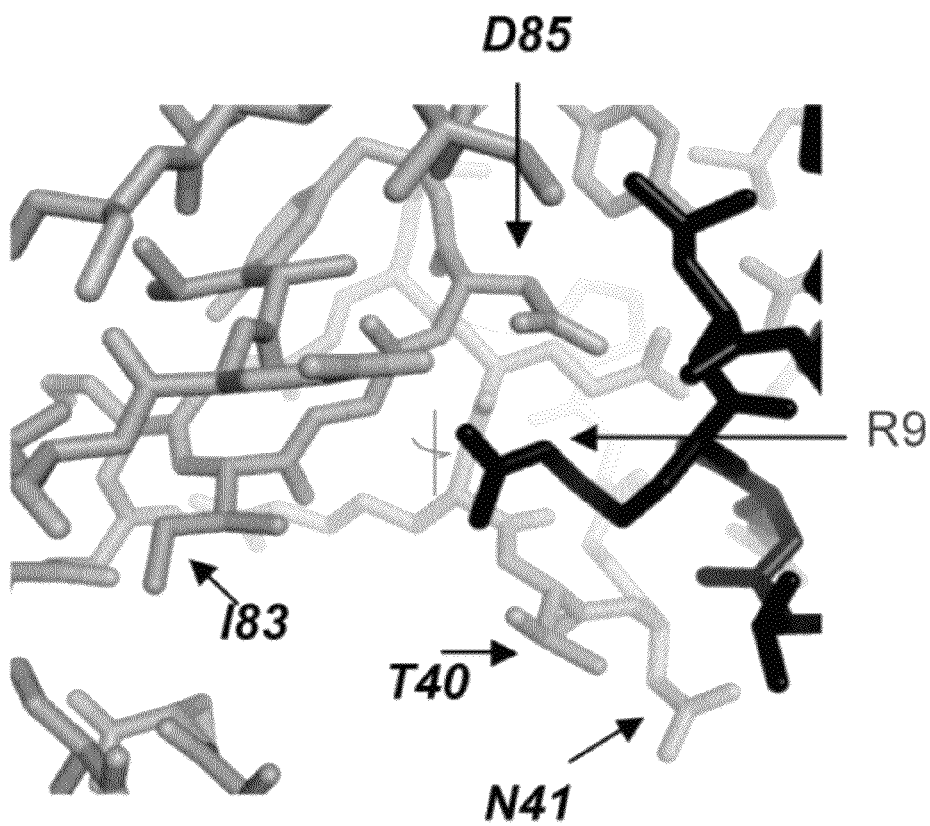
FIG. 2 shows certain embodiments of the cetuximab Fab binding interface. Cetuximab is a murine chimera and therefore has a mix of murine Ig variable domains and human constant Ig domains.

In some embodiments, the one or more human framework residues that are replaced by the corresponding murine residues may be selected from light chain framework residues 10, 39-43, 83, 85, 100 and 104 (Kabat numbers) and/or heavy chain framework residue numbers 40, 89 and 111 (Kabat numbers) (see FIG. 2). In one embodiment, the one or more human framework residues that are replaced by the corresponding murine residues are light chain framework residues including, but not limited to, 40, 41, 83 and 85. Specifically, in one embodiment, light chain framework Pro40 is replaced with Thr (P40T) or Ser (P40S), light chain framework Gly41 is replaced with Asn (G41N), light chain framework residue Phe83 is replaced with Ile (F83I) or Val (F83V) and light chain framework residue Thr85 is replaced with Asp (T85D) or Asn (T85N). This meditope-site grafting (or "murinization" or "mousification") of this Fab cavity within human monoclonal antibodies can be used to create a unique handle for meditope binding and used with the technology previously disclosed. In addition, additional point mutations may be engineered by generating a pharmacophore binding model to further enhance the affinity of the meditope.

The embodiments described herein identify and characterize a novel interface within the Fab framework, and demonstrates that it does not perturb the binding of Fab to the antigen or act as an allosteric antagonist of EGFR binding. In addition, the two peptide meditopes do not bind to the cetuximab CDRs, and thus do not mimic the antigen (EGFR).

A "therapeutically effective amount," "therapeutically effective concentration" or "therapeutically effective dose" is the amount of a compound that produces a desired therapeutic effect in a subject, such as preventing or treating a target condition, alleviating symptoms associated with the condition, or producing a desired physiological effect. The precise therapeutically effective amount is the amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

A "route of administration" may refer to any administration pathway known in the art, including but not limited to aerosol, enteral, nasal, ophthalmic, oral, parenteral, rectal, transdermal, or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

"In combination" or "in combination with," as used herein, means in the course of treating the same disease or condition in the a subject using two or more agents, drugs, treatment regimens, treatment modalities or a combination thereof (e.g., an antibody in combination with a meditope or a multivalent tethering agent), in any order. This includes simultaneous administration (or "coadministration"), administration of a first agent prior to or after administration of a second agent, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

A "therapeutic antibody" may refer to any antibody or functional fragment thereof that is used to treat cancer, autoimmune diseases, transplant rejection, cardiovascular disease or other diseases or conditions such as those described herein. Examples of therapeutic antibodies that may be used according to the embodiments described herein include, but are not limited to murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

In one embodiment, a method of screening for novel meditopes or small molecules with framework binding functionality similar to that of a meditope is provided herein. Such a method may include, but is not limited to, steps of contacting a library of putative meditopes or small molecules with a meditope-enabled antibody; determining whether the putative meditopes of small molecules bind the meditope-enabled antibody at a framework binding interface; identifying one or more candidate meditopes or a small molecules with framework binding functionality similar to that of a meditope; determining binding affinity of the one or more candidates; and identifying one or more of the candidates as a meditope or small molecule with framework binding functionality similar to that of a meditope when the binding dissociation constant is at least 0.70 μM. Additionally, methods of screening for novel framework binding interfaces are also provided, and are described further in the examples below Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

Determination of Crystal Structures

Materials and Methods

Reagents. The antigen binding fragment [F(ab)'] (or "Fab") of cetuximab was obtained by digestion of the IgG with immobilized papain (Pierce), followed by reverse purification with protein A and size exclusion chromatography (SEC) on a Superdex 75 column (GE Healthcare). The single chain binding fragment (scFvC225) of cetuximab was synthesized with a twenty amino acid linker between the light chain and heavy chain. ScFvC225 and soluble epidermal growth factor receptor domain III (sEGFRdIII) were expressed in Sf9 cells and purified as previously described (Donaldson et al., 2009).

Meditopes CQFDLSTRRLKC (cQFD; SEQ ID NO:1) and CQYNLSSRALKC (cQYN; SEQ ID NO:2), isolated from a phage display as previously described (Riemer et al. 2005), were synthesized, oxidized and purified at the City of Hope Synthetic and Polymer Chemistry Core Facility.

Crystallization and Diffraction Data. The Fab fragment of cetuximab (5 mg/mL) was mixed with individual meditopes at a 1:10 molar ratio and screened using the Qiagen JCSG Core Suites (IIV) at 20° C. Co-crystals that diffracted beyond 2.2 Å were grown in 100 mM sodium phosphate/citrate, pH 4.5, 2.5 M sodium/potassium phosphate and 1.6% w/v meso-erythritol. The crystals were wicked through 14% w/v meso-erythritol and flash frozen in liquid nitrogen. Crystallization trials and initial screening studies were carried out in the X-ray facility at the City of Hope. Diffraction data were collected at the Stanford Synchrotron Radiation Lab, beam lines 9.1 and 11.1. The initial phases were determined by molecular replacement using the program Phaser (McCoy et al., 2007) with the unliganded structure of cetuximab (pdb: 1YY8—chains A and B) (Li et al., 2005). Two Fabs were placed in the asymmetric unit with a Matthews Coefficient of 3.26 and solvent content of 62.4%. The Z scores (standard deviation of the solution over the mean) were 27 and 25 for the rotational search and 38 and 71 for the translational search. A third Fab fragment could not be placed (three Fabs in the asymmetric unit cell produces a reasonable Matthews coefficient of 2.18 at 43% solvent). The meditopes were built into the density manually through multiple iterations using Coot (Emsley et al., 2004) and Phenix (Adams et al., 2002).

Crystallization and Structure Determination

To identify the binding site of the meditopes on cetuximab, the Fab fragment was generated and purified, mixed with the cQFD meditope at a 1:10 ratio and commercial factorials were used to screen for crystal formation. Crystals formed after 1 to 3 days at 20° C. Initial diffraction analysis of these crystals indicated that the unit cell was similar to the cetuximab Fab already deposited in the Protein Data Bank (1 YY8.pdb) (Li et al., 2005), and the crystal packing (e.g., the CDRs were excluded) suggested the peptide was not present at the CDR loops. Nonetheless, the structure was solved by molecular replacement and the experimental maps were examined to identify unmodeled electron density consistent with the meditope. The initial Fo-Fc map clearly indicated an area in the middle of the Fab fragment as a potential binding site (FIG. 1). After an initial round of refinement using the Fab model only, a continuous stretch of unmodeled density consistent with the meditope was observed. The meditope was built into the density and the R and RFree dropped accordingly. Water molecules were added during refinement using Phenix (Adams et al., 2002). The diffraction data and refinement statistics are given in Table 3 below.

| Experimental and Refinement Statistics for Co-Crystal Structures | | |
|---|---|---|
| | cQFD | cQYN |
| Data collection | | |
| Space group | $P2_12_12_1$ | $P2_12_12_1$ |
| Cell dimensions | | |
| a, b, c (Å) | 64.29, 82.53, 211.7 | 64.16, 82.52, 211.9 |
| α, β, γ (°) | 90.00, 90.00, 90.00 | 90.00, 90.00, 90.00 |
| Resolution (Å) | 20-2.24 (2.3-2.24) | 30-2.20 (2.26-2.20) |
| $R_{mrgdF}$ | 0.078 (0.50) | 0.067 (0.26) |
| I/σ(I) | 17 (3.1) | 25.5 (6.0) |
| Completeness (%) | | |
| I/σ > 0 | 91.6 (74.4) | 97.0 (92.8) |
| I/σ > −3 | 97.4 (83.3) | 99.9 (100) |
| Redundancy | 4.2 (3.2) | 7.9 (8.2) |
| Refinement | | |
| Resolution (Å) | 19-2.24 | 29.6-2.20 |
| No. reflections[#] | 53791 | 58047 |
| $R_{work}/R_{free}$ | 184/23.4 | 18.6/23.0 |
| No. atoms | | |
| Protein | 6602 | 6529 |
| Mimotope | 200 | 188 |
| Water | 556 | 539 |
| B-factors | | |
| Protein | | |
| Fab | 31.4 | 31.2 |
| Mimotope | 49.7 | 62.6 |
| Water | 37.1 | 37.1 |
| r.m.s.d. | | |
| Bond lengths (Å) | 0.003 | 0.007 |
| Bond angles (°) | 0.710 | 1.07 |
| Ramachandran | | |
| favored/allowed/disallowed | 96.7/0.2/0.1 | 98.0/2.0/0.0 |

*Values in parentheses are for highest-resolution shell with I/σ(F) > 0.
[#]F/σ(F) > 1.99 for and > 1.36 for cQFD or cQYN co-crystals, respectively.

Based on these observations and as a point of comparison, crystals were produced of the cetuximab Fab bound to the second meditope identified by phage display, cQYN. As before, clear unmodeled electron density was observed in the center of the Fab. Using the first structure, the differences in sequences were modeled accordingly and multiple rounds of refinement were carried out. Representative electron density maps of both meditopes are shown in FIGS. 1B and C.

EXAMPLE 2

Meditopes are Specific to a Murine Framework Region of Cetuximab Fab

Materials and Methods

In addition to those described in Example 1 above, the following materials and methods were used.

Meditopes and point mutations. As described above, CQFDLSTRRLKC (cQFD; SEQ ID NO:1) and CQYNLSSRALKC (cQYN; SEQ ID NO:2), were synthesized, oxidized and purified at the City of Hope Synthetic and Polymer Chemistry Core Facility. Alanine point mutations in the cQFD meditope were generated at residues 3 (Phe3 to Ala), 5 (Leu5 to Ala), 8 (Arg8 to Ala) and 10 (Leu10 to Ala) and were produced bacterially by encoding the peptides at the C-terminus of SMT3 (Mossessova et al., 2000). Before surface plasmon resonance (SPR) analysis, ubiquitin-like protease (Ulp1) was added to the samples to release the peptides.

Characterization of the meditope-Fab interface. Affinity analysis by SPR was performed as previously described (Donaldson et al., 2009; Li et al., 2005). Briefly, scFvC225 or FabC225 was immobilized on a CM5 chip using amine chemistry. Peptide or sEGFRdIII affinities were assessed by equilibrium methods at 20° C. and fit to the equation RU={Rmax*[L]}/{[L]*Kd}+Roffset. SEC was performed using a Superdex 200 10/30 column (GE Healthcare). The proteins were mixed, incubated at room temperature for 20 min and applied to the column at 4° C.

The MDA-MB-468 cell line was used to test cetuximab binding in the presence of peptide meditope. Labeled cetuximab (AF488, Invitrogen) was added for 20 min with or without 60 μM cQFD peptide at 4° C. Labeled MOPS-21 was used as an isotope control. Cell fluorescence was determined using a FACS Calibur instrument (BD Biosciences).

Analysis of Meditope/Fab Interface

The interface of the binding site between the meditope and the Fab identified herein is formed by all four domains of the IgG (e.g., the variable and constant domains of the heavy and light chains). Using the PISA server, the buried surface area at the cQFD or cQYN meditope-Fab interface was 904 (±28) Å2 and 787 (±42) Å2, respectively, and equally distributed between the light and heavy chains. FIGS. 2 and 4 show the residues and the loops from the Fab that contacts the meditope.

Both meditopes make multiple hydrogen bonds and hydrophobic contacts with the cetuximab Fab. FIG. 2A shows the subtle differences between the residues of the central cavity binding interface of the cetuximab Fab (murine chimera IgG), the humanized monoclonal IgG used as an isotype control in the phage display experiments (ch14.18) and the humanized trastuzumab Fab. Superposition of the humanized trastuzumab Fab on the cetuximab Fab indicated that Arg9 of the cQFD meditope binds to a unique cavity created by the mouse variable light chain. Specifically, Asp85, Ile83 and Thr40 of the mouse variable light chain are important with respect to binding to the Arg9 residue of the cQFD meditope (FIG. 2B). Asp85 in the murine framework makes a salt bridge to the guanidinium group of Arg9 of the cQFD meditope (dNE . . . OD1=2.8 Å & dNH1/2 . . . D2=3.0 Å). The carboxyl group of Asp85 also makes a hydrogen bond to the backbone amide of Leu10 of the cQFD meditope (dOD2 . . . HN=2.7 Å). The hydroxyl group of Thr40 from the light chain also makes a hydrogen bond to guanidinium group of the meditope Arg9 (dOG1 . . . NH1=3.1 Å). The phenyl ring in Phe83 and the pyrrolidine ring of Pro40 in the human Fab sterically occlude the side chain of Arg9.

Although the selection of the Arg9 side chain in the cQFD meditope maps to the differences between the murine and human Fab sequences, it was also noted that the cQYN meditope encodes an alanine at the same position as Arg9 in the cQFD meditope, and thus could potentially bind to the human Fab. To discern why the cQYN meditope was selected despite pretreating the phage library with the hu14.18 antibody, differences between the cQFD and cQYN meditopes and their interaction with the cetuximab Fab were determined. Superposition of the Cα atoms of the heavy and light Fab chains from the cQFD and cQYN structures show that the hydrophobic side chains of residues Phe/Tyr3, Leu5 and Leu10 from each meditope are positioned nearly identically (FIG. 2B). However, the backbone traces of the cQFD and cQYN peptides deviate significantly. Specifically, the Arg8 side chain structure of the cQFD meditope is extended and makes a strong backbone hydrogen bond to the backbone carbonyl of Gln111 of the Fab heavy chain (dNH . . . O=C=2.8 Å). The hydroxyl group of Tyr3 in the cQYN peptide, however, sterically interferes with the Arg8 side chain (FIG. 2B) and blocks the interaction between Arg8 of the cQYN meditope and Asn111 of the heavy chain. Consistent with this observation, both Arg8 side chains in the cQYN complex are poorly defined in the electron density map and takes on at least two different rotamers. (There are two Fab-meditope complexes in the asymmetric unit.) Concomitant with this change, a shift in the backbone hydrogen bond pattern was observed. The amide carbonyl of Thr7 in the cQFD meditope makes a hydrogen bond to the amide Asn41 in the cetuximab Fab light chain (dNH . . . OC=2.7 Å). This hydrogen bond shifts to the carbonyl of the Arg8 backbone in the amide of backbone of Asn41 in the cQYN peptide (dC=O . . . HN=3.0 Å).

Collectively, the differences between the cQFD and cQYN (e.g., loss of a salt bridge between R8 and the heavy chain Fab) and sequence differences in the Fab light chain where Arg9 in cQFD binds (e.g., the loss of the hydrogen bond between Asp85 and the amide of Leu10 for either meditope) indicate that the meditopes selected to bind to the murine chimera have substantially weaker interactions with human Fab frameworks and were removed in the washes during the selection.

Meditopes do not Induce Large Conformational Changes in the Fab

Figure 6:
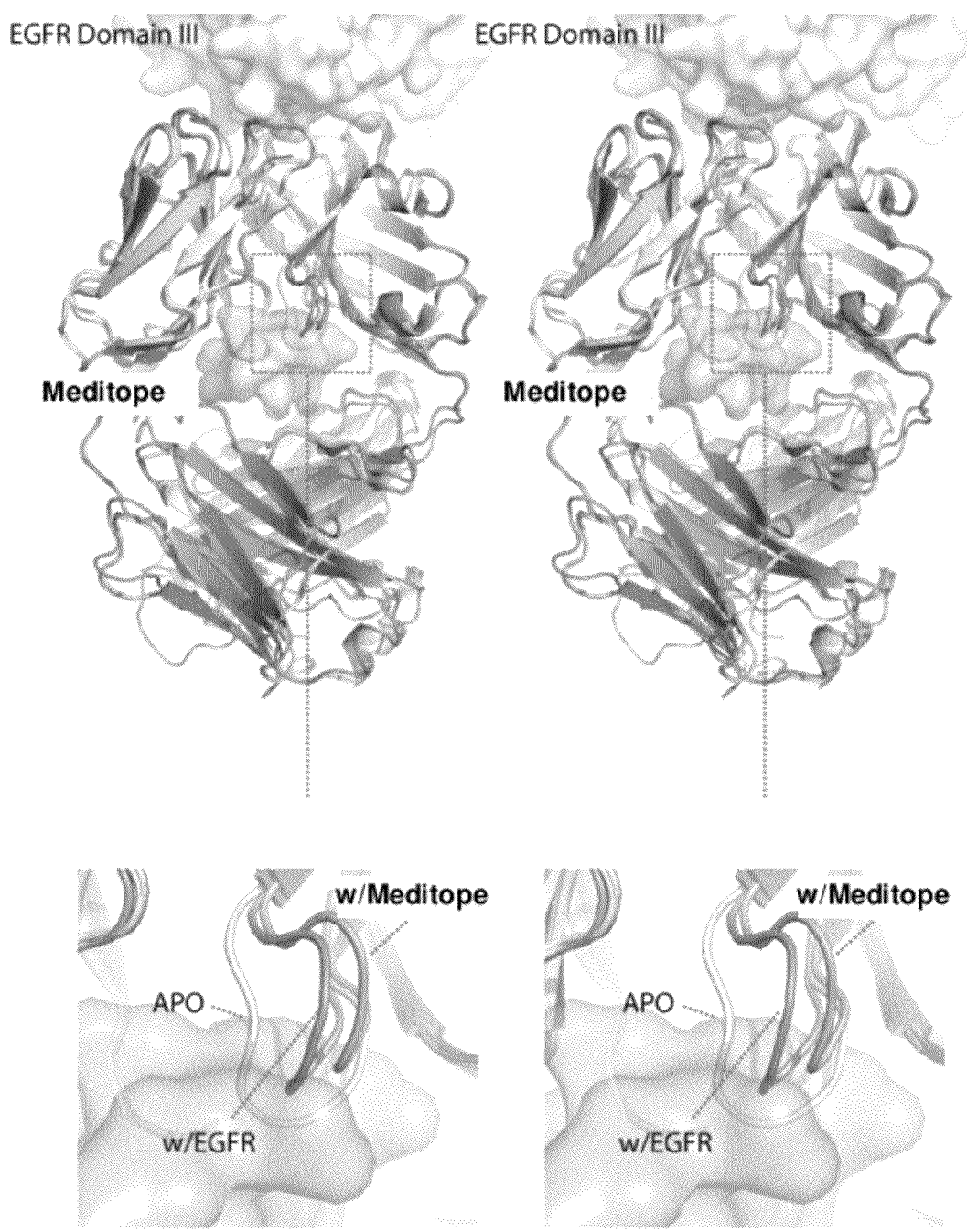
FIG. 6 shows how meditope and EGFR bind to distinct sites. The top images show superposition of the cQFD-Fab complex and the EGFR-Fab complex (1YY8) in stereo. The bottom images show that residues 39-46 of the heavy chain are flexible and accommodate the meditope.

Based on the location of the meditope-Fab interface, it was determined whether the meditopes perturbed the relative orientation of the IgG domains to the unligated and/or ligated structure. First, the light and heavy chains within the asymmetric unit cell of both meditope complexes were compared and then each chain was compared to the unligated and EGFR-ligated structures. The variable domains of the light chains bound to either meditope were essentially identical to the unligated structure of cetuximab (r.m.s.d. average: cQFD, 0.231±0.014 Å, cQYN, 0.18±0.01 Å). However, the variable domains of the heavy chain showed significantly higher divergence (r.m.s.d. average: cQFD, 0.85±0.01 Å, cQYN, 0.88±0.01 Å). It is noted that this divergence stems primarily from the position of framework loop 2 (residues 39-46), since deleting the residues in this loop and recalculating the r.m.s.d. produced a much lower value: cQFD, 0.18±0.01 Å; cQYN, 0.31±0.01 Å) (FIG. 6). In addition, this loop is also displaced in the Fab C225-EGFR co-crystal structure, and its relative B-factor value suggests that it is flexible (FIG. 6). Finally, the presence of the meditope does not result in significant changes to the CDR structure relative to the EGFR bound or unbound structure. Although the backbone of Tyr101 in the heavy chain CDR loop 3 of the EGFR liganded structure is flipped as compared to the Fab structure bound to either meditope, this flip is also observed in the unliganded cetuximab Fab structure (Li et al., 2005).

Contribution of Meditope Residues to Interface

Figure 3:
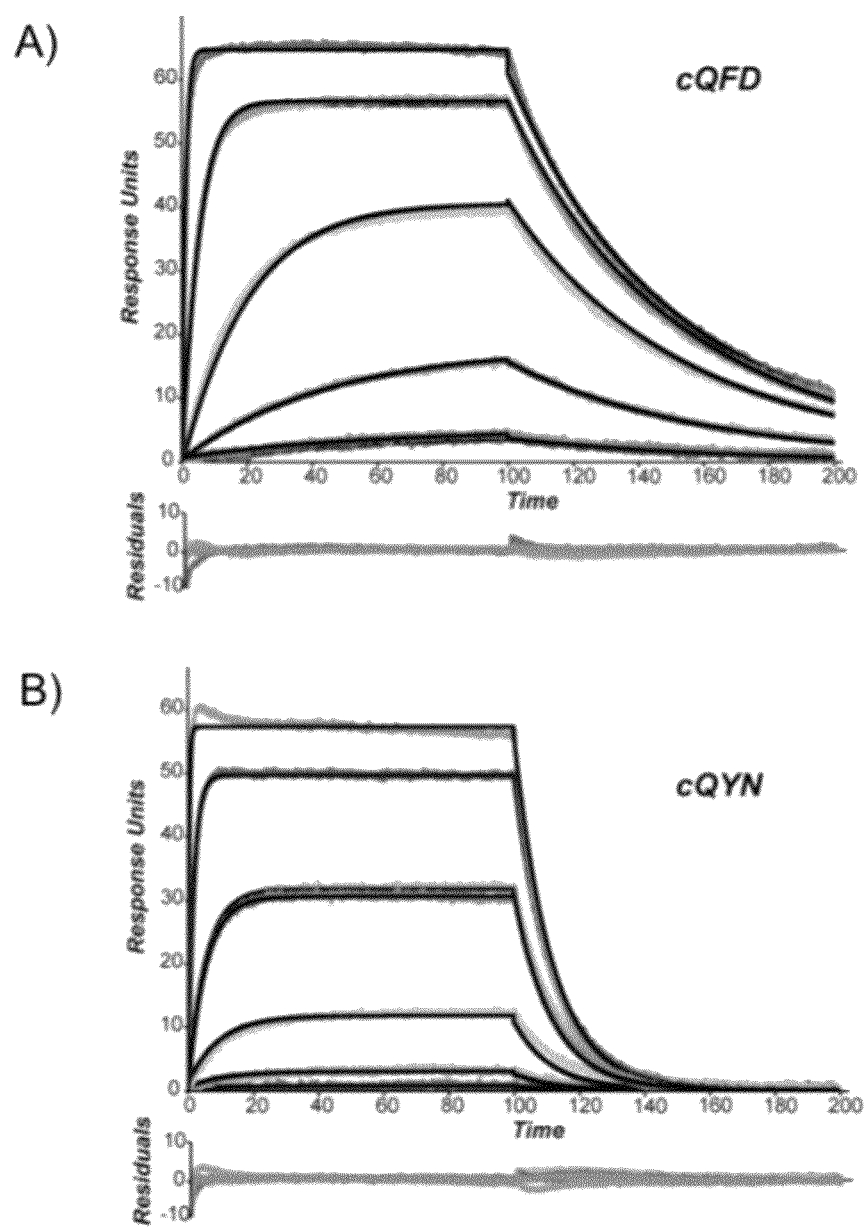
FIG. 3 shows two line graphs showing surface plasmon resonance (SPR) traces of cQFD and cQYN and the Fab fragment. The cetuximab Fab used for crystallographic studies was coupled to a CM5 chip at low densities. Traces at increasing concentrations of the cQFD (FIG. 3A) and cQYN (FIG. 3B) meditopes are shown. The series of traces are fit to single binding site model using a simple exponential (e.g., signal=A*exp[kon*time]). The residuals of the fit are shown below each.

Based on the structure of the cQFD meditope-Fab complex, as well as the sequence similarity of cQYN to cQFD, several point mutations in the cQFD meditope were generated (Phe3→Ala, Leu5→Ala, Arg8→Ala and Leu10→Ala) to characterize the role of these residues to the overall binding affinity of the meditope. To assess binding affinity, the Fab fragment was coupled to a CM5 chip using standard amine chemistry. Next, the affinity of the synthetic cQFD and cQYN meditopes to the cetuximab Fab was measured. The cQFD meditope bound to the Fab with an affinity of 950±30 nM whereas the cQYN meditope bound with an affinity of 3.5±0.1 µM (n=3). The binding kinetics were also measured (FIG. 3). The association constants, modeled as a bimolecular interaction, were 4.2 (±0.1)×104 M-1s-1 and 1.8 (±0.1)×104 M-1s-1 for cQFD and cQYN, respectively. The dissociation constants were 2.5 (±0.1)×10-2 s-1 and 8.6 (±0.1)×10-2 s-1 for cQFD and cQYN, respectively. The KD values based on these measurements, 430 (±30) nM for cQFD and 3.5 (±0.1) pM for cQYN, are in close agreement with the equilibrium measurements.

Next, the affinity of each mutated cQFD meditope was measured. The point mutation and wildtype cQFD meditopes were generated as C-terminal fusions to SMT3 and cleaved with Ulp1 before the analysis. The biologically-produced, wildtype cQFD meditope bound with an affinity of 770 nM, similar to the synthetically-produced cQFD, whereas the mutations Phe3→Ala, Leu5→Ala and Arg8→Ala significantly reduced the affinity for the Fab (Table 4, below). In particular, the Arg8→Ala mutation resulted in a 140-fold loss in binding affinity.

| Dissociation constants of cQFD mimotope mutants | | |
|---|---|---|
| Ligand | $K_D$ (µM) | ΔΔG (kcal/mol) |
| WT | 0.77 | — |
| F3A | 34 | 2.3 |
| L5A | 57 | 2.6 |
| R8A | 141 | 3.1 |
| L10A | 2.2 | 0.63 |

-continued

Dissociation constants of cQFD mimotope mutants

| Ligand | $K_D$ (μM) | ΔΔG (kcal/mol) |
|---|---|---|

Finally, the Fab of trastuzumab, a humanized therapeutic monoclonal antibody, was coupled to a CM5 chip to characterize the affinity of the cQFD and cQYN meditopes to a human framework. Equilibrium measurements revealed that the dissociation constants for either meditope exceed 150 μM.

EXAMPLE 3

Cetuximab Fab Binds Meditopes and EGFR Simultaneously

Materials and Methods

In addition to those described in Examples 1 and 2 above, the following materials and methods were used.

Reagents. The single chain binding fragment (scFvC225) of cetuximab was synthesized with a twenty amino acid linker between the light chain and heavy chain. ScFvC225 and soluble epidermal growth factor receptor domain III (sEGFRdIII) were expressed in Sf9 cells and purified as previously described (Donaldson et al., 2009).

Meditopes and point mutations. As described above, CQFDLSTRRLKC (cQFD; SEQ ID NO:1) and CQYNLSSRALKC (cQYN; SEQ ID NO:2), were synthesized, oxidized and purified at the City of Hope Synthetic and Polymer Chemistry Core Facility. Alanine point mutations in the cQFD meditope were generated at residues 3 (Phe3 to Ala), 5 (Leu5 to Ala), 8 (Arg8 to Ala) and 10 (Leu10 to Ala) and were produced bacterially by encoding the peptides at the C-terminus of SMT3 (Mossessova et al., 2000). Before surface plasmon resonance (SPR) analysis, ubiquitin-like protease (Ulp1) was added to the samples to release the peptides.

Simultaneous Binding of EGFR and Meditope to Fab

The diffraction data conflict with the hypothesis that these peptides are effective as vaccines. Specifically, the atomic model shows that the meditopes do not directly bind to the CDRs, and thus do not mimic an antigen epitope. However, serum collected from mice inoculated with the cQYN meditope blocked cell proliferation (Riemer et al., 2005). Therefore, to test whether or not the meditope occludes antigen binding, the cetuximab Fab was incubated with EGFR-domain III and cQFD and applied to an analytic SEC column. A peak at 13.9 mL was observed, and non-reducing SDS-PAGE of the peak showed the presence of all three components (FIG. 4B). The individual components eluted at 15.2 mL (Fab C225), 15.6 mL (sEGFRdIII) and 16.3 mL (SMT-CQFDLSTRRLKC; SEQ ID NO:1).

In addition, it was determined whether or not the meditope could bind to the scFv of cetuximab. In the scFv, the CDR loops remain intact, but the Fab variable domains are directly connected through a short peptide linker, eliminating the Fab constant domains. In other words, the meditope binding pocket is eliminated in the scFv, while the CDRs are minimally affected. SPR demonstrated that EGFR domain III and the cQFD meditope bound to cetuximab Fab tethered to a CM5 chip (See FIG. 4B). In addition, EGFR domain III bound with a minimal affinity loss to the scFv tethered to a second CM5 chip. However, relative to Fab binding, the cQFD meditope did not saturate the scFv at concentrations as high as 100 μM of meditope. This indicates minimal, if any, affinity of the meditope for the CDRs, consistent with the crystallographic studies.

Meditope Does not Affect Cetuximab Binding to EGFR-Expressing Cells

Figure 5:
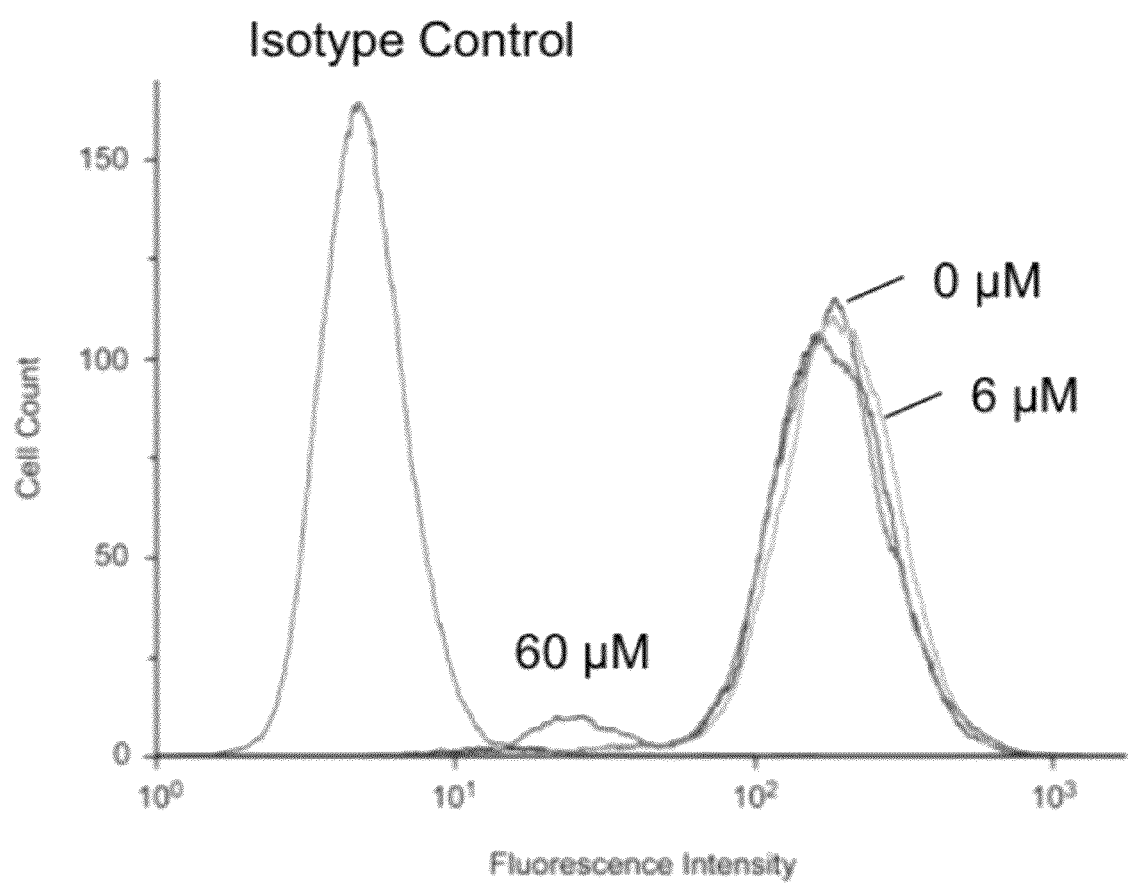
FIG. 5 is a graph of fluorescence intensity compared to cell count and shows fluorescently-labeled cetuximab binding to MDA-MB468 cells in the presence of cQFD. Cetuximab binds to MDA-MB468 cells without peptide, and in the presence of 6 µM and 60 µM peptide as well as the isotype control.

Although the Fab could bind to the meditope and EGFR domain III simultaneously, it was determined whether the meditope could affect cetuximab binding to EGFR-expressing cells as a full IgG. To test this, FACS analysis was used to follow the binding of the IgG, as a function of meditope concentration, to MDA MB-468 cells, which overexpress EGFR. Cells were incubated with cetuximab in the presence of increasing cQFD meditope concentrations. Even with meditope concentrations greater than 60 μM, no significant changes in cetuximab binding to the cells were observed (FIG. 5). This observation is consistent with the SEC studies described above, and indicates that the meditope does not act as an allosteric regulator of antigen binding.

Simultaneous binding to the Fab of EGFR domain III and the meditope is shown at concentrations significantly above the $K_D$ of the meditope. Like the cQFD and cQYN meditopes, superantigens SpA and PpL, bind to the Fab framework region and do not affect antigen binding (Graille et al., 2000; Graille et all., 2001; Graille et al., 2002; Young et al., 1984).

Figure 10:
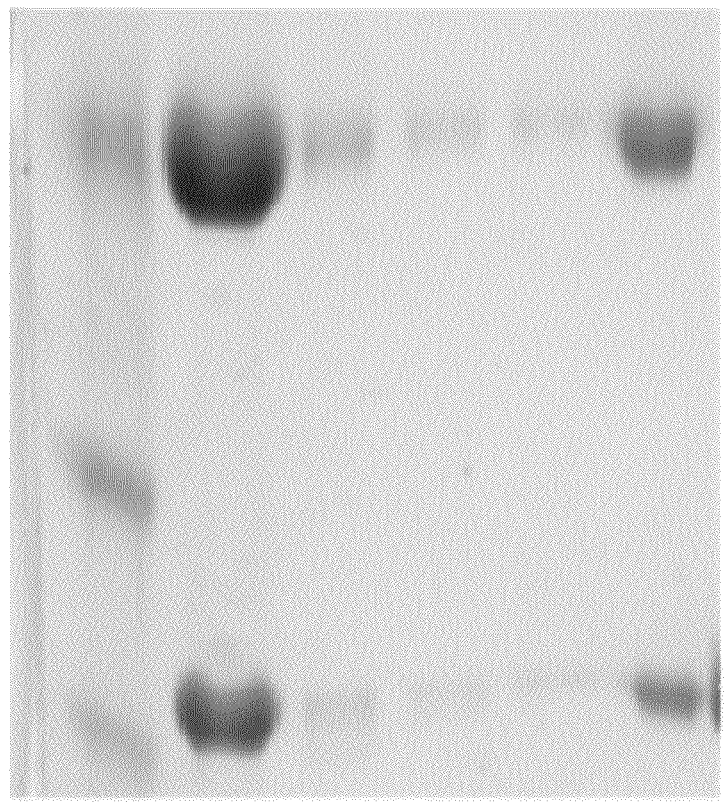
FIG. 10 is a gel showing that the meditope selectively binds the murine cetuximab. Biotinylated cQFD peptide was added to avidin coupled beads, thoroughly washed, and equilibrated in PBS. Cetuximab was then added to the beads (lane 1), washed (lanes 2-4), and then eluted (lane 5). The top band is the IgG heavy chain and bottom band is the IgG light chain.

In addition, the meditope chemical coupled to a solid support can be used to purify the murine chimera cetuximab, which represents a novel method to purify murine chimera IgGs as well as meditope-grafted gGs. See FIG. 10. There are several of advantages to this purification approach. First, the meditope is easily synthesized and can be readily added to common solid supports (including magnetic beads). Second, the affinity of the meditopes is easily modulated by point mutations, which enables the fine-tuning of the purification procedure and avoids harsh conditions such as low pH that is commonly used to elute antibodies. Finally, as described herein, the meditopes can be made bivalent or multivalent (such as those described in Example 5 below) and used to extract intact murine or mousified human IgGs. The use of a peptide would also have additional advantages over current purification methods that use Protein A or Protein L, including the high cost associated with the production of Protein A or Protein L, limited life cycle and, potential introduction extraneous biological material such as bacterial pathogens.

Steric Mask

Figure 11:
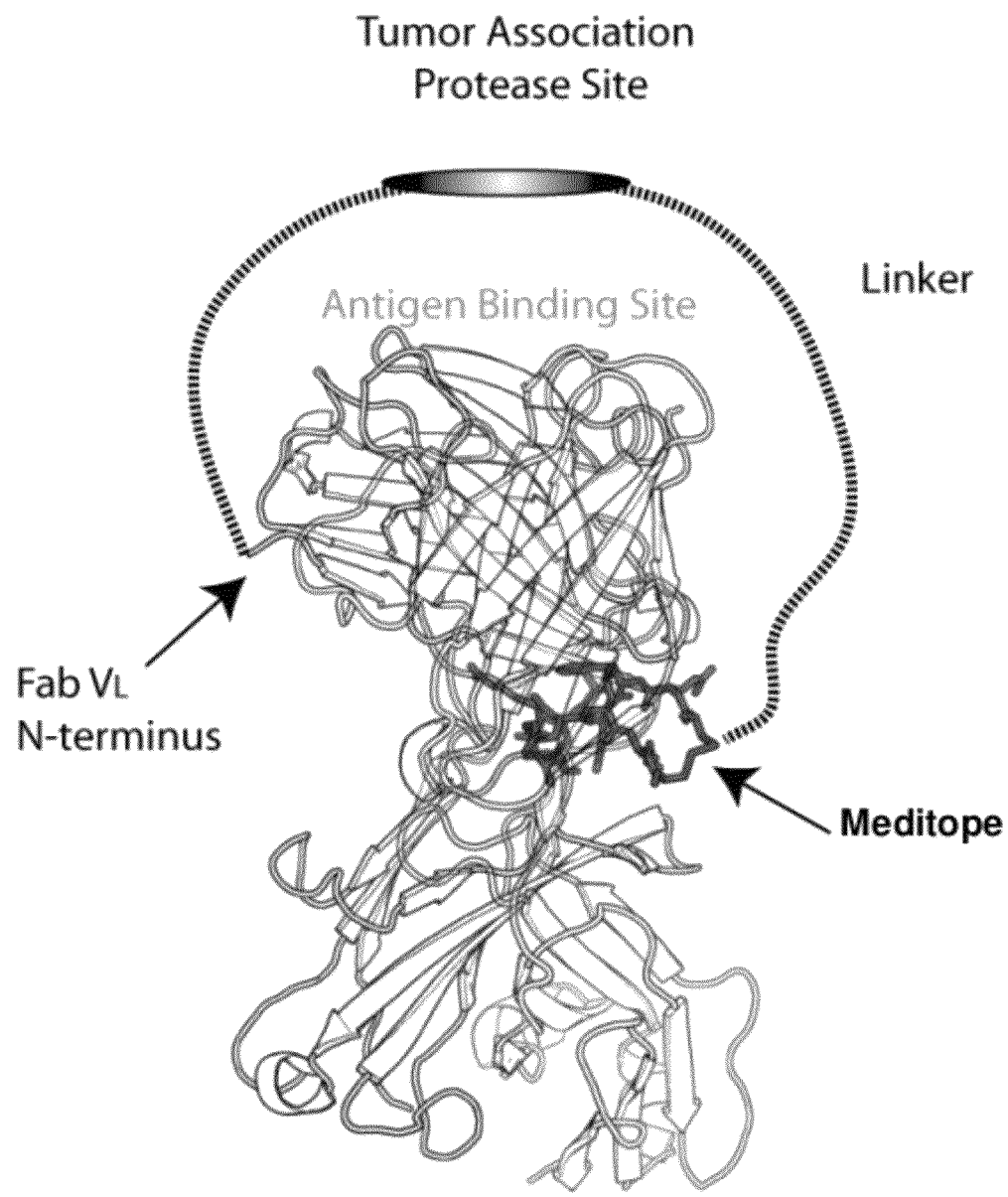
FIG. 11 is a depiction of the steric mask. The meditope can be fused to the N-terminus of the Fab light or heavy chain through a flexible linker containing a tumor associated protease site. An intramolecular interaction, as shown, would sterically occlude the antigen binding site.
Figure 12:
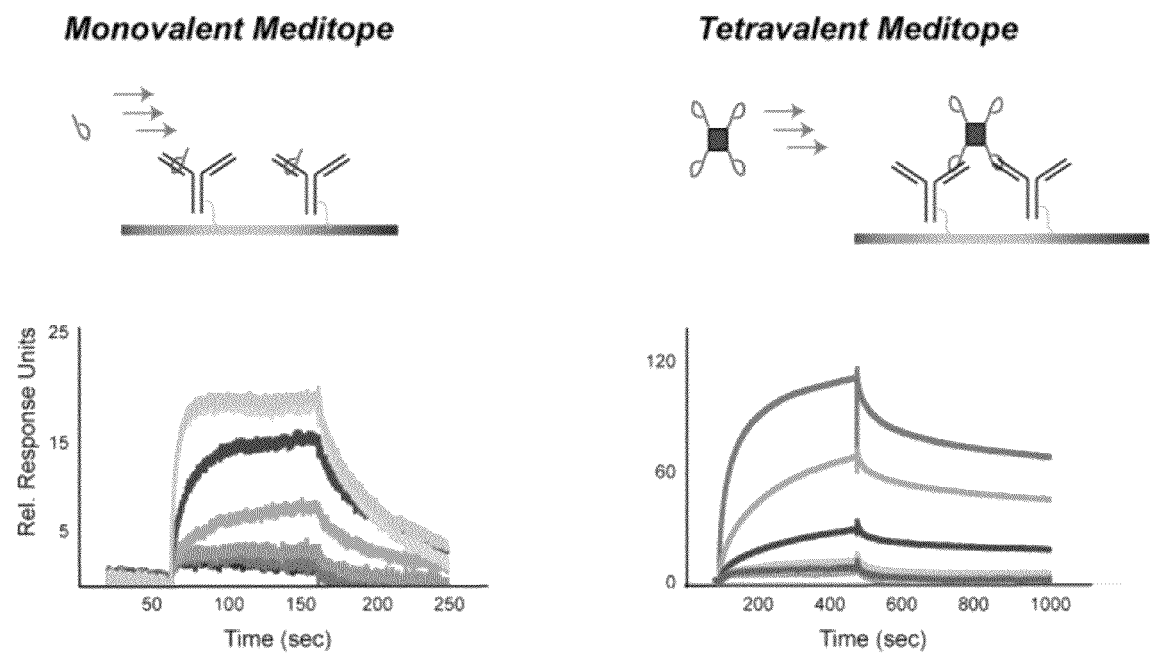
FIG. 12 shows the off-rate determination for Avidin-peptide mask on Cetuximab. The left panel shows that the binding kinetics of a biotinylated cQFD meditope was measured by SPR using immobilized cetuximab IgG. The boxed panel above the surface plasmon resonance traces depicts a cartoon of the monovalent meditopes being passed over the bivalent IgG. As shown in the right panel, Avidin was saturated with biotinylated meditope and passed over the same immobilized cetuximab IgG. The off-rate of the multivalent meditope was reduced by at least 36 fold. (Note the time scales between the two experiments are different.) The boxed panel above the SPR traces depicts a "bivalent-bivalent interaction" between the tetravalent meditope and the bivalent IgG.

The meditope can be tethered to the N-terminus of either the light chain or heavy chain N-terminus of a murine chimera or mousified human mAb through a flexible linker (FIG. 11). The N-termini of mAb IgGs are juxtaposed to the antigen binding site and the extension from the N-termini through the flexible linker will sterically interfere with antigen binding. By encoding a tumor specific protease site (e.g., MMP9, MMP14, prostate-specific antigen (PSA) serine protease or other suitable site) in the linker, the steric constraint of intramolecular 'masked' IgG construct will be severed at the tumor site and permit antibody binding. This design principle would avoid binding of the intramolecularly 'masked' IgG to healthy tissues and avoid adverse side effects due to off-target binding. The off-rate determination for Avidin-peptide mask on Cetuximab is shown in FIG. 12. This figure shows that a mutivalent meditope binds with higher affinity than a monovalent meditope, but does not mask.

EXAMPLE 4

Optimization of Meditopes Binding to Cetuximab

Figure 15:
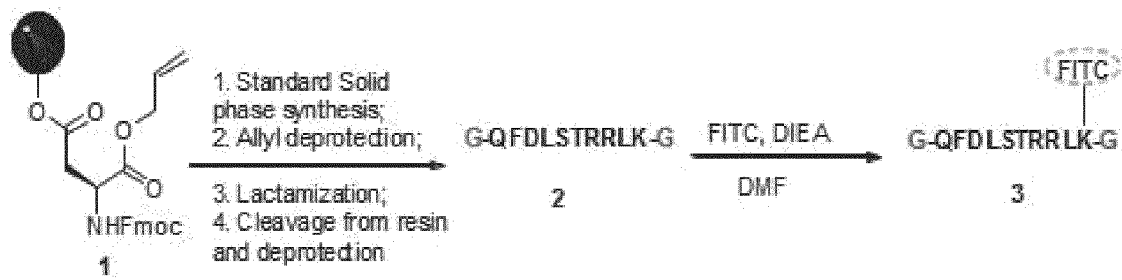
FIG. 15 illustrates the synthesis of a lactam peptie (2)(SEQ ID NO:22) and a fluorescein-labeled lactam peptide (3 (fluorescein isothiocyanate (FITC)-labled peptide of SEQ ID NO: 22)).

A series of modifications to the meditope, including the incorporation of D-amino acids, non-natural amino acids and different cyclization strategies to optimize the meditope-Fab binding affinity will be investigated (see FIG. 15). Each meditope analog may be purified and structurally characterized, and its interaction with the Fab may be analyzed by surface plasmon resonance (SPR), isothermal titration calorimetry (ITC), diffraction methods or a combination thereof. The data gleaned from this synthetic and biophysical approach will be used for subsequent modifications to optimize binding in a reiterative manner.

Figure 13C:
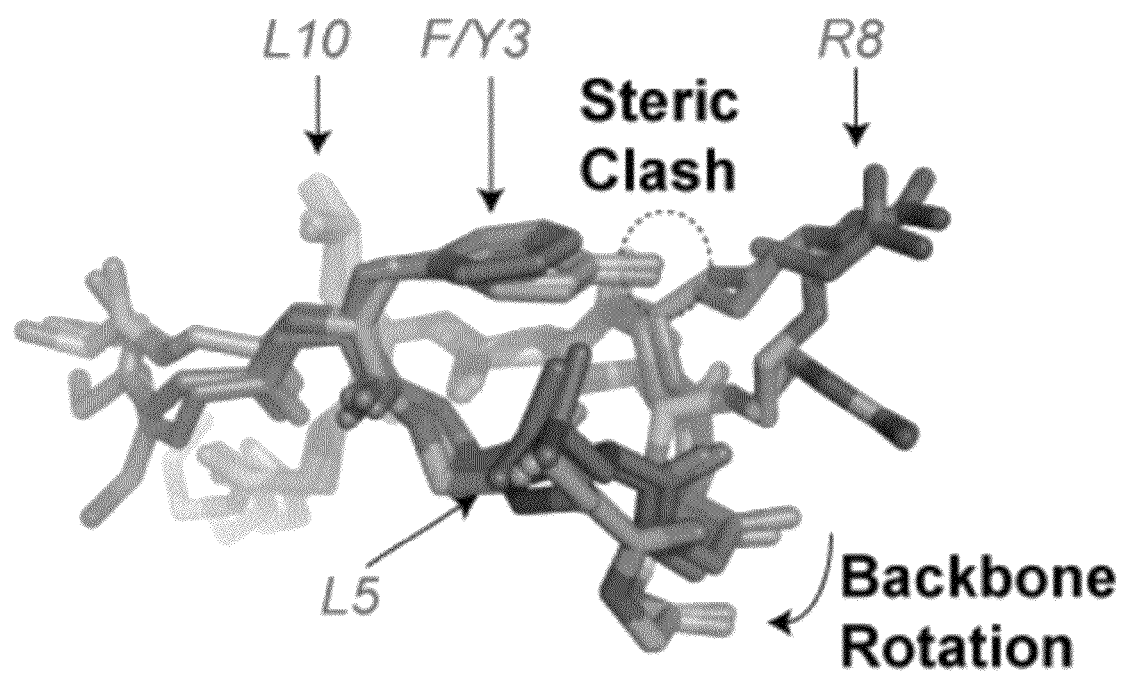
FIG. 13C shows superposition of the cetuximab Fabs bound to the unmodified meditope and Phe3Tyr. Oval 1 indicates the Phe/Tyr position. Oval 2 shows shift in the Arg8 side chain. The arrow indicates a shift of the backbone that leads to a favorable hydrogen bond network and may account for a favorable change in the enthalpy.

Biochemical and Structural Data. As described above, cyclic peptides cQFD and cQYN were identified by phage display with the intention of identifying peptides that bind to cetuximab CDR regions, thereby mimicking an EGFR epitope, as part of a vaccination strategy. In an effort to rationally design tumor-activated, pro-mAbs, cQFR and cQYR were co-crystallized with cetuximab Fab, and unexpectedly, the meditope bound in the cavity created by the light and heavy chains of the Fab. Many biophysical and biochemical methods were used to characterize this interaction. Specifically, mutation of Phe3, Leu5, and Arg8 to alanine reduced the affinity of the meditope for the binding interface by 10-140-fold. In addition, a cetuximab scFv that binds to EGFR, but lacks the Fab cavity, could not bind to the meditope. The meditope then binds cetuximab that is already bound to the antigen, as shown in by FRET, SPR and FACS analysis studies described in Example 5 below (also see FIG. 13).

Since this observation, many meditope variants have been generated to establish structure-activity relationships and to improve overall affinity for the Fab. To date, a number of meditope variants have been co-crystallized with the cetuximab Fab, and the binding affinity of each variant has been characterized by SPR and ITC. The structure of these meditope variants, which correspond to SEQ ID NOs:5-8, 12-15 and 21-30, are shown in FIG. 30. Most of these structures diffract beyond 2.4 Å and are well refined with R and RFree less than 20 and 24%, respectively (see FIG. 31). All have very good stereochemical values (Molprobity scores above 80%). Therefore, a large number of meditope permutations may be systematically and efficiently addressed to produce a large number of meditope permutations with the goal of producing a high affinity meditope.

Meditope Chemistry Design

Figure 14:
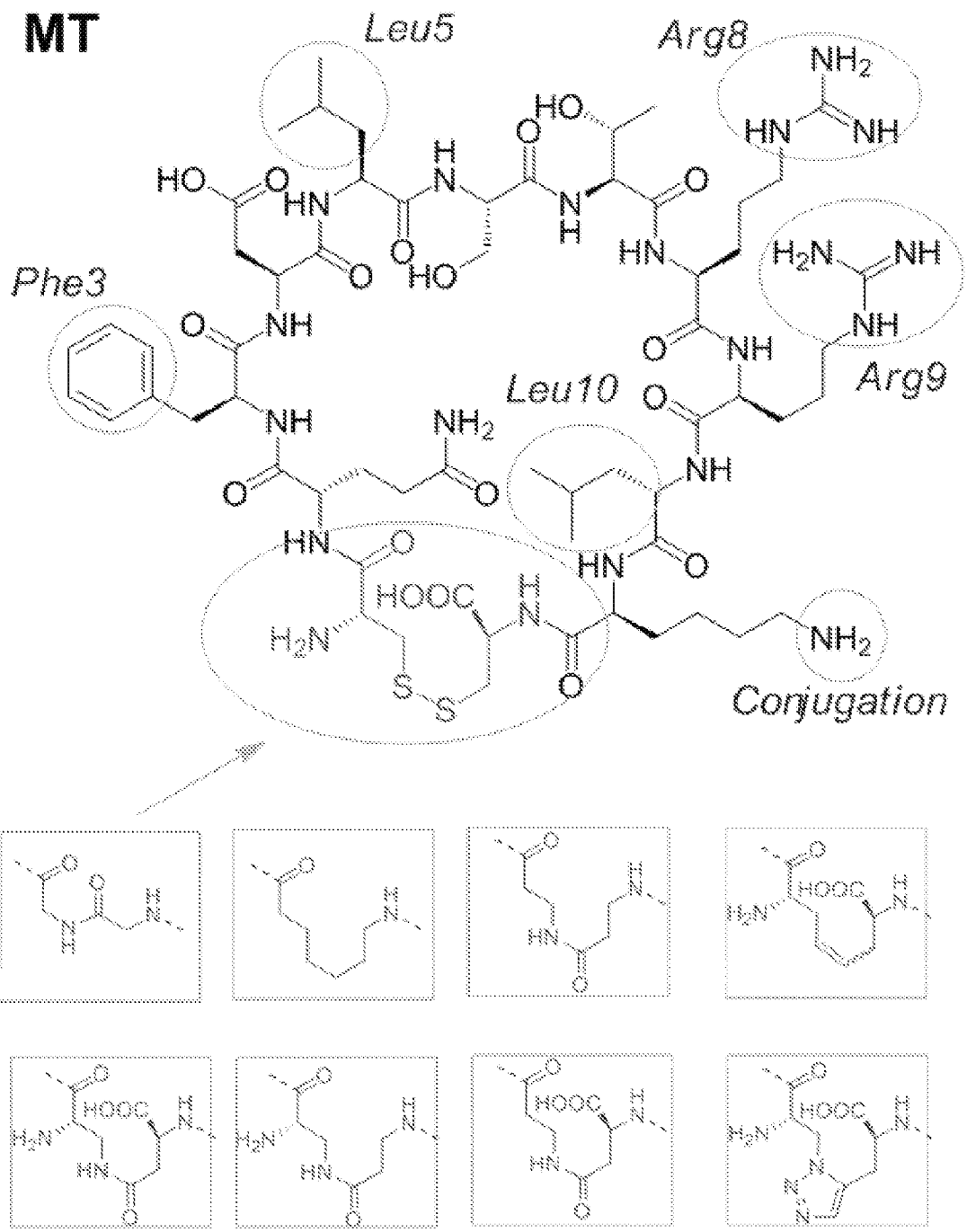
FIG. 14 shows the chemical structure of the meditope. The circles indicate positions that will be modified to improve the meditope affinity for the Fab. The boxes indicate cyclization strategies. 'Click' chemistry and olefin metathesis, middle and right boxes, respectively, are additional routes to cyclize the meditope.

Based on the structures and thermodynamic data obtained in the Examples above, multiple positions within the meditope that can be modified with non-natural amino acids to enhance the overall binding affinity of the monovalent fragment have been identified. Modifications that may be used to enhance binding affinity include, but are not limited to, a head-to-tail cyclic lactam peptide, modification of Arg8, modification of Phe3, modification of Leu5 and/or Leu10, and incorporation of hydratable carbonyl functionality (FIG. 14).

Head-to-tail cyclic lactam peptides. Various methods for cyclization of a meditope may be used to address in vivo stability and to enable chemoselective control for subsequent conjugation chemistry. For example, a head-to-tail lactam peptide was designed and synthesized by solid phase peptide synthesis (SPPS) starting from Fmoc-Asp (Wang resin LL)-Oall (FIG. 14, lower left box & FIG. 15). This variant, meditope V3, bound to cetuximab in a similar manner but with slightly reduced affinity compared to the unmodified meditope.

Figure 17:
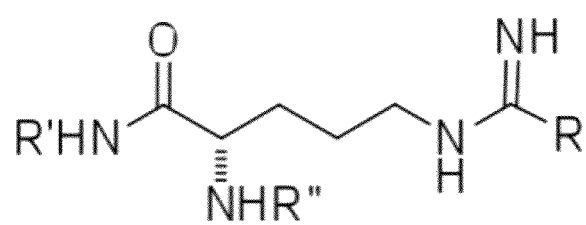
FIG. 17 shows a modified Arg8 residue that may be used to optimize the meditope.

The head-tail meditope platform may be advantageous for several reasons. First, the lactam is expected to be more stable in vivo. Second, this allows for the introduction of a single reactive amine functionality (e.g., Lys11) for subsequent meditope conjugation. For example, the V3 meditope variant was conjugated with fluorescein for FACS analysis and note that this strategy can be applied to DOTA for future in vivo PET imaging (FIG. 17). Further, head-tail meditope synthesis affords the material in high yield. The structural data indicates additional positions are amendable to cyclization, including between residues 3 and 11. Each meditope may be characterized by ITC, SPR and diffraction methods and the meditope with the highest affinity is subsequently modified to improve the overall affinity. Briefly, these characterizations are calculated as follows.

Peptide lyophilized powders were suspended in 500 uL of 10 mM Tris pH 8.0 buffer and dialyzed 3 times into 1 L of $H_2O$ each time. The final volume after dialysis was carefully measured and absorbance measurements were taken to estimate the concentration (typically 1-10 mM). These stock solutions were used to make dilutions into HBS-EP buffer (10 mM Hepes pH 7.4, 150 mM NaCl, 3 mM EDTA and 0.05% v/v surfactant P20) for SPR measurements. SPR measurements were carried out on the GE Biacore T100 instrument using a CM5 chip with Cetuximab IgG or Cetuximab Fab ligand immobilized using amine coupling chemistry. Ligands were immobilized at low levels suitable for kinetic data. Typical kinetics SPR experiments were carried out at a flow rate of 30 uL/min using HBS-EP as both running and regeneration buffer. Kinetic parameters were calculated using the Biacore T100 Evaluation software version 2.0.1.

All isothermal titration calorimetry experiments were performed in 100 mM Hepes, pH 7.4 at 25° C. using Nano ITC calorimeter (TA Instruments). In a typical experiment 250 µA of protein (Fab or IgG) at 0.03-0.06 mM were loaded into the colorimeter cell (163 µl or 185 µl) and the titrant (meditope, at 0.3-0.8 mM) was loaded into a 50 µl syringe. The cell solution was stirred at 250 rpm and upon equilibration the titrant was added in 2-2.5 µl increments. Heat of the reaction was measured and the data was processed using NanoAnalyze software (TA Instruments). Background heat was subtracted by averaging the last four measurements or by subtracting heat of reaction obtained from titration of the meditope at the same concentration into buffer containing no protein.

Various lactam cyclization strategies can be used based on different starting materials including β-Ala, 7-aminoheptanoic acid, etc to produce different lactam ring size (FIG. 14, left and middle boxes). If necessary, additional cyclization strategies such as 'click' chemistry and olefin metathesis may be used (FIG. 14, right boxes).

Figure 16:
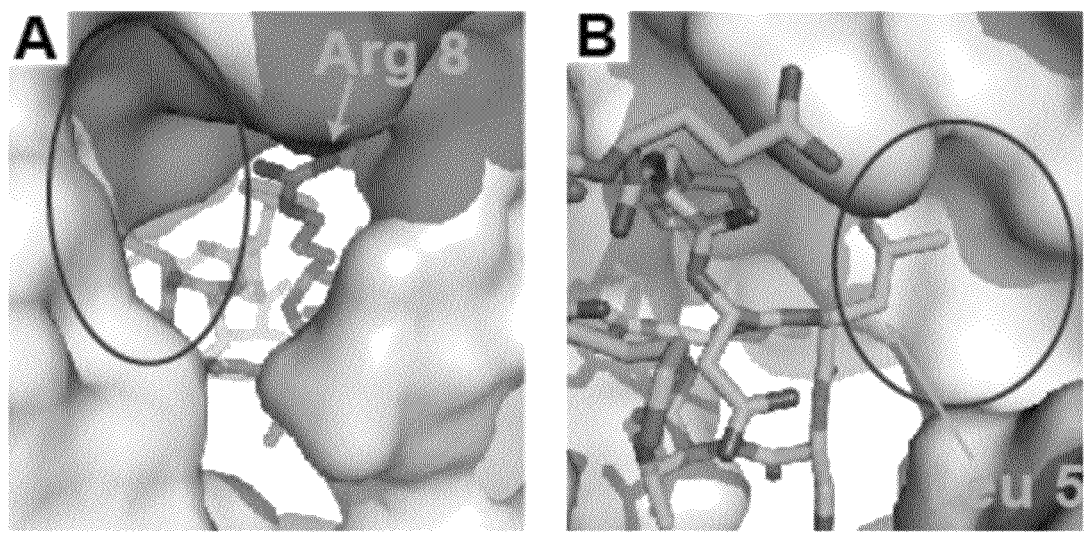
FIGS. 16A-B shows the sites of optimization according to some embodiments. Ovals indicate cavities that may optimize affinity of the meditope.

Modification of Arg8. In the unmodified meditope, Arg8 is extended, making a hydrogen bond with the heavy chain carbonyl of Asn111. The immediate area about this residue is hydrophobic yet solvent exposed (FIG. 16A). Thus, the incorporation of a modified Arg8 residue that maintains the guanidinium functionality for Fab H-bonding while simultaneously introducing a hydrophobic arm to fill the cavity may produce significant gains in binding due to entropic increases. This is supported by ligand docking calculations. For example, modified Arg8 (FIG. 17) represents a class of compounds that contain the requisite ambivalent functionality.

Figure 13D:
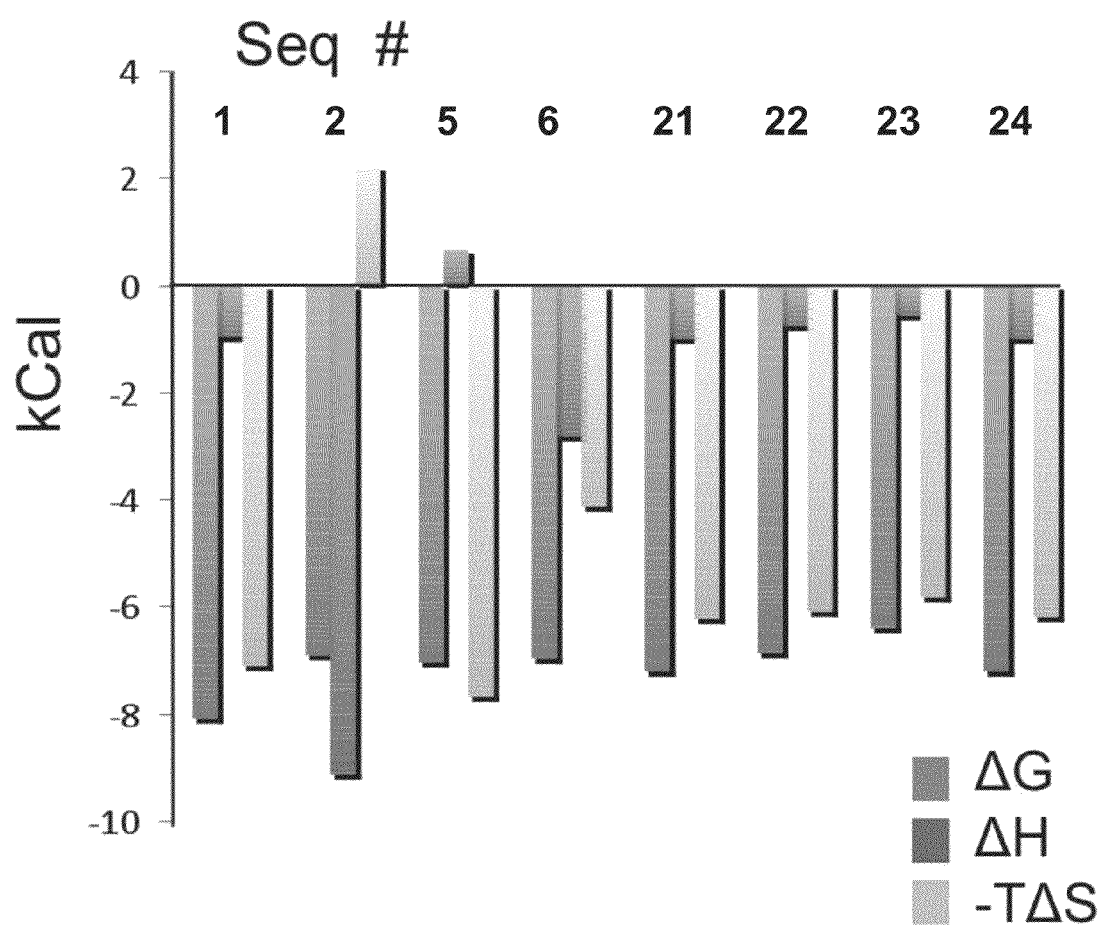
FIG. 13D shows individual thermodynamic parameters determined by ITC of different meditope variants. The Phe/Tyr variant (V2) shows a significant change in ΔH though lower affinity. Based on the structure, Gln2 in the meditope was replaced with the D-stereomer. ITC analysis of this meditope, (SEQ ID NO:5), revealed a significant increase in entropy and loss in enthalpy.

Modification of Phe3. Using structural data, it was observed that the hydroxyl group of the meditope variant Phe3Tyr cQYN alters the extended conformation of the Arg8 side chain (see FIGS. 13C and 18). The overall affinity of this variant for the cetuximab Fab, as determined by SPR, is reduced. ITC measurements indicated a significant decrease in entropy for this analog upon binding that was off-set by a favorable increase in enthalpy compared to unmodified meditope (from −2.1 kCal/mol to −7.9 kCal/mol [n=3]) (FIG. 13D). Structural data suggest the formation of a favorable hydrogen bond network, with water bound to the Fab; however, more analogs are necessary to understand the structural basis of these entropic and enthalpic changes. While enthalpy-driven optimization has proven successful in many small-molecule approaches in drug design, there are also opportunities in this particular system for engineering increases in entropy as well. Consequently, approaches that result both in enthalpic and entropic gains in meditope designs may be used to optimize binding.

Figure 18:
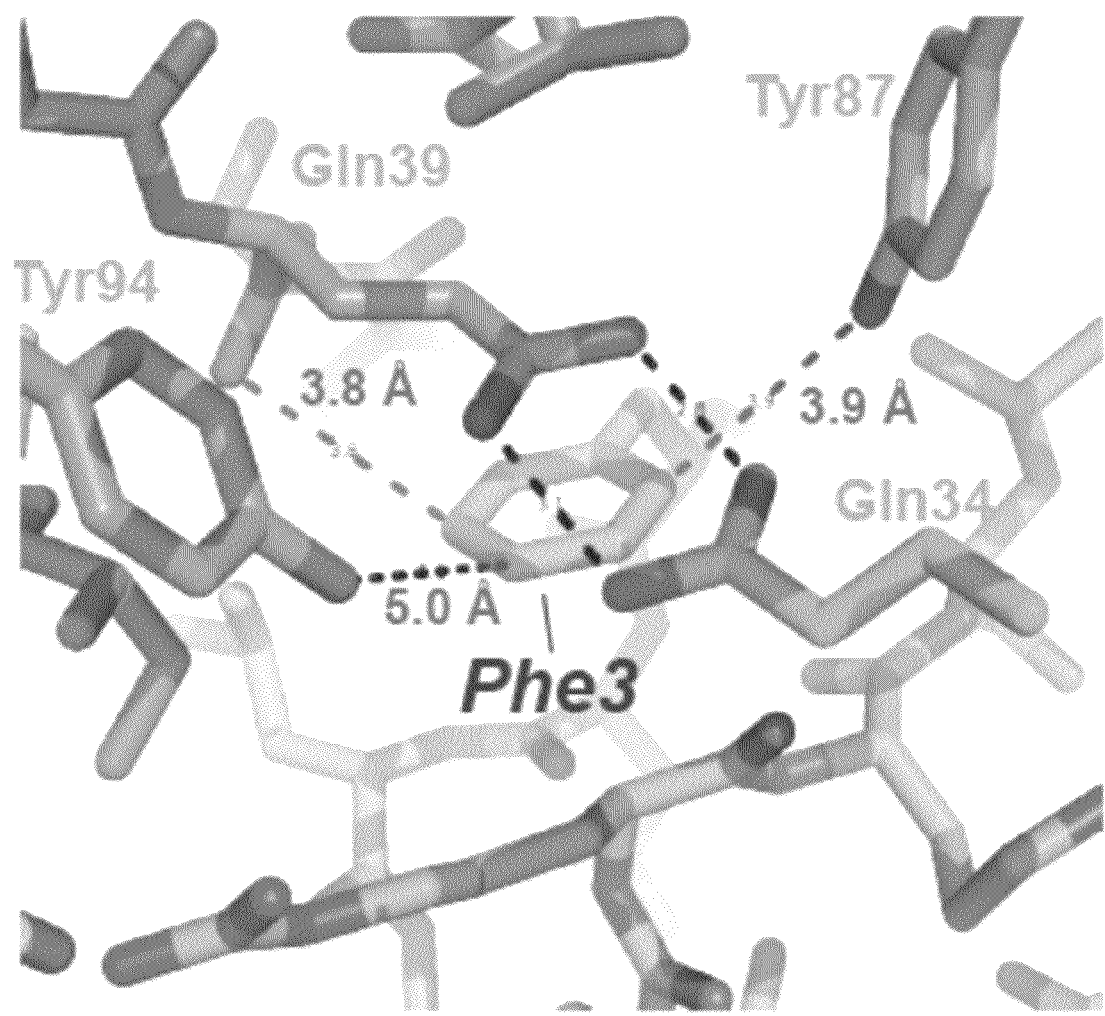
FIG. 18 shows the hydrophilic interface in the vicinity of Phe3. Halogens incorporated in the phenyl ring may form strong noncovalent bonds to the hydroxyl group of Tyr87 or Tyr94, as well as backbone carbonyls.

For example, the hydrophilic phenyl ring of Phe3 is surrounded by a fairly polar array of side chain residues of the Fab (FIG. 18). Therefore, halogens may be introduced on the phenyl ring that could participate in halogen bonding. A halogen bond is a relatively strong non-covalent bond, similar to a hydrogen bond but involving the interaction of a halogen such as bromine or chlorine with an oxygen atom. For instance, incorporation of an ortho-, meta-, and/or para-bromo phenyl substituent would favorably place a bromine atom for halogen bonding with Tyr87 (light chain), Gln38, and/or Tyr94 (heavy chain) of the Fab, respectively. Many of these derivatives are commercially available and may be incorporated by SPPS.

Figure 35:
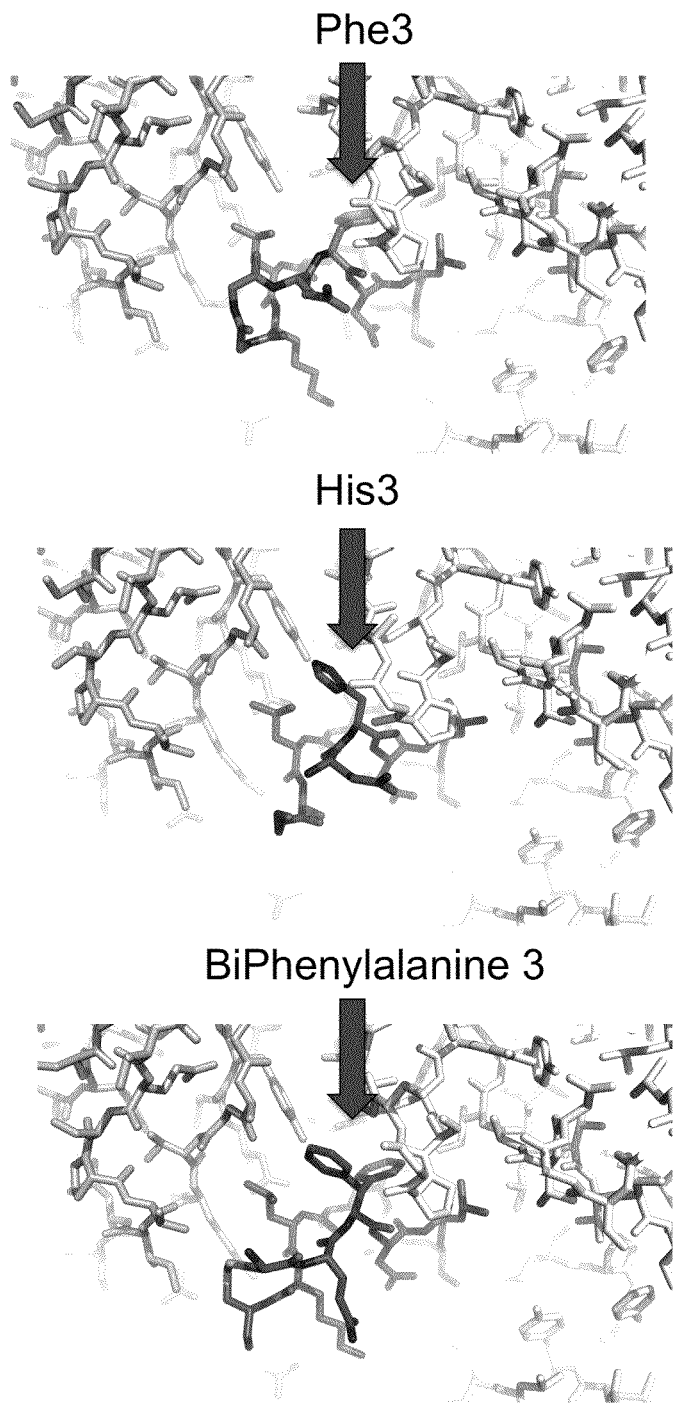
FIG. 35 illustrates structural information to improve meditope affinity. The top panel shows crystal structure of a meditope bound cetuximab. Phenylalanine 3 binds within the Fab cavity. Substitution of this position with histidine and subsequent structural analysis indicates the side chain (imidazole) takes on a new conformation (middle panel). Based on this observation, 3,3'-biphenylalanine which could place one phenyl side chain at the original position and one phenyl side chain at the imidazole ring was substituted at position 3. The crystal structure indicates that this substitution mimics both side chain conformations. Surface plasmon resonance studies shows that this substitute binds with higher affinity (FIG. 34—top panel).

Modification of Leu5 and Leu10. Both of these side chains make hydrophobic contacts to the Fab (FIG. 19, right panel; Leu10). To improve the affinity, the amount of surface area that can be buried can be extended by incorporating non-natural amino acids. This may be illustrated by systematically introducing natural (Phe/Tyr/Trp) and non-natural analogs (e.g., 3,3-Diphenyl-L-alanine, branched alkyl, extended aromatics such as napthyl, etc.) via SPPS at both positions. For example, at position three increases the overall affinity by a factor of approximately 4 to 5 (200 nM). See FIGS. 34-35. This also supports that mutation of residues and the use of structural biology to identify regions may be used to improve the binding kinetics of the meditope.

Figure 19:
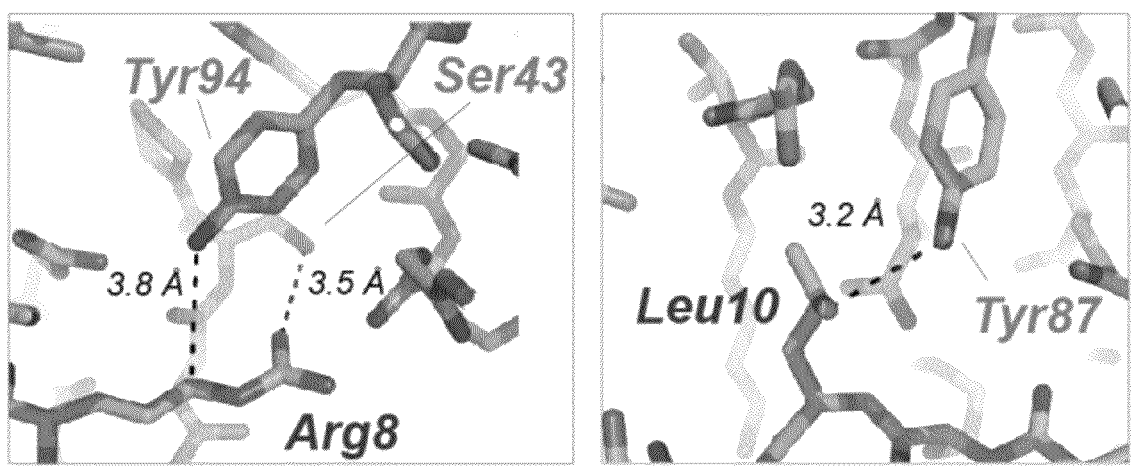
FIG. 19 illustrates covalent interactions between the meditope and the backbone framework. A hydratable side chain may be incorporated at Arg8 (left) or Leu10 (right) to form a covalent bond to the hydroxyl groups of Ser or Tyr of the Fab.

Hydratable carbonyl functionality. A meditope that has hydratable carbonyl capabilities may be developed to create a highly selective but irreversible interaction. Several Fab hydroxyl-bearing side chains that surround the meditope cavity may be exploited through selective trapping as their corresponding hemi-acetal or -ketal using a hydratable-enabled meditope. For example, Arg8 of the meditope extends in proximity to Ser43 (3.5 Å) and Tyr94 (3.8 Å) of the Fab (FIG. 19, left panel). Incorporation of a hydratable carbonyl functionality at the end of Arg8 or Leu10 would allow for selective formation of a serine or tyrosine hemi-acetal. Such a covalent adduct would essentially afford irreversible binding. In addition, residues containing boronic acid may also be integrated into the meditiope as an alternative to a hydratable carbonyl group. Boronic acid plays an important role in the structural activity of bortezamib (Velcade®), which is used to treat multiple myeloma. Representative examples of hydratable residues are also shown in FIG. 19 where R=$CH_2CHO$ or —$CH_2B(OH)_2$. The analogs proposed in this study may be modified using SPPS (52).

Meditope-Cetuximab Binding Characterization

Each monovalent meditope is purified to >95% homogeneity and structurally characterized by mass spectrometry. Further, all peptides are dialyzed in water, their concentrations measured by UV-Vis and calibrated with elemental analysis, and diluted (>100×) into the appropriate buffer. Binding to cetuximab is rigorously characterized by ITC, SPR, X-ray diffraction or a combination thereof. ITC measurements may be performed on a TA Instruments nanoITC, which requires only 1-2 mg of peptide per measurement. In preliminary studies, the unmodified meditope binds with similar enthalpy and entropy to the cetuximab Fab fragment or the fully intact IgG. Therefore, binding measurements are carried out using the full IgG. For SPR measurements, low density and high density chips were conjugated with the cetuximab Fab and full IgG. Each chip was first characterized using a soluble fragment of the entire extracellular domain of EGFR (residues 1-621). Similar kinetics and binding affinities were observed as previously reported. Using the low density chips, on and off rates were measured for the unmodified meditope and determined to be $k_{on}=9.2\times10^{-4}$ $M^{-1}$ $sec^{-1}$ and $k_{off}=9.9\times10^{-3}$ $sec^{-1}$, respectively. Consistent with ITC, similar values for the Fab-conjugated chip and the IgG-conjugated chip were observed.

Finally, each meditope-cetuximab interaction may be characterized by diffraction methods. In preliminary studies, diffraction data was collected for 20 different meditope-Fab complexes, including the original cQFD and cQYN meditopes and modified meditopes. Since the co-crystallization conditions of the Fab and meditope are now well-established, diffraction quality crystals are typically obtained in 1 to 3 days. Full data sets are collected in 8 to 12 hours with an in-house source (Rigaku 007-HF and an R-Axis IV++) and in 10 min at the Stanford Synchrotron Radiation Lightsource, which allows for rapid characterization of the interactions of the meditope variants with cetuximab.

Collectively, ITC, SPR and X-ray diffraction data provide the atomic detail necessary to guide subsequent chemical modifications and ultimately improve the affinity of the meditope. A simple calculation based on $\Delta G=-RT \ln Ka$ shows that the difference between micromolar and nanomolar affinity results from a change in free energy at 300 K of ~4 kCal/mol, which is on the order of a strong hydrogen bond. Thus, the loss of an ordered water molecule from a protein binding pocket or the reorientation of an amino acid residue-chain may be sufficient to alter binding by orders of magnitude.

At least two alternative approaches may be used to improve the affinity of the meditope-Fab interaction. First, the structural data obtained in the studies described above may be used to replace residues in the Fab, by mutagenesis, to add additional hydrogen bonds, substitute amino acids for unnatural amino acids or alter the hydrophobic interface that might better complement meditope binding. (See FIGS. 29 and 29). Second, fluorescence polarization assays may be used to identify small molecules that can displace the meditope, and use these small molecules as templates to further improve the binding affinity.

EXAMPLE 5

Generation of Multivalent Meditopes

Combinations of monoclonal antibodies (mAbs) that recognize unique epitopes on the same antigen (e.g., EGFR) have been shown to enhance cell death and inhibit tumor growth. While the precise mechanism of this enhanced cell death remains debated (immunological response versus receptor down regulation versus enhanced ligand antagonism), previous studies indicate that both Mabs should be multivalent (e.g., full IgG or F(ab)'$_2$) to achieve enhanced cell death. As such, a multivalent meditope may be substituted as a second antibody as shown below. Therefore, the meditopes describe herein may be tethered to a scaffold to create a multivalent meditope for enhanced selectivity and binding affinity.

Specificity and affinity are often achieved through multivalency. This can be expressed as $\Delta G_{Total}=\Delta G1+\Delta G2-\Delta G_{linker}$ for a bivalent ligand, which is equivalent to $K_{Total} = K_1 * K_2 / K_{linker}$. In the case where the linker makes no contribution to the free energy ($K_{linker} \sim 1$), the apparent affinity of the bivalent ligand for the bivalent target is the product of the monomeric binding constants. Thus, significant gains in affinity can be achieved (e.g., for a meditope with $K_D=1$ µM, the affinity of a 'theoretical' bivalent meditope is 1 pM. Such gains, however, are rarely seen, primarily due to the geometry of the bivalent/trivalent/multivalent receptor. The geometry of the receptor places strict constraints on the linker, but it also ensures specificity, which is an important goal for targeted delivery.

To address the receptor constraints on the linker, the unmodified or optimized meditopes obtained in Example 4 may be coupled to a multivalent scaffold. To accomplish this, the linker is optimized. Because tumor cells have high antigen density, a multivalent meditope should "latch-on" to adjacent IgGs to form a "daisy-chain"-like array (FIG. 8). While an intramolecular association of a bivalent meditope and IgG is possible, the C2 symmetry of the IgG would place severe geometrical constraints on the linker for such an interaction. A trivalent or higher valency scaffold ensures that more than one antibody would be "daisy chained". By including a third meditope arm, the lifetime of the initial encounter of a trivalent meditope to antigen-bound antibody will increase. This, in turn, will increase the probability that an additional arm will bind to a neighboring antigen-bound antibody, thus stabilizing the overall complex.

Scaffold Synthesis

Figure 20:
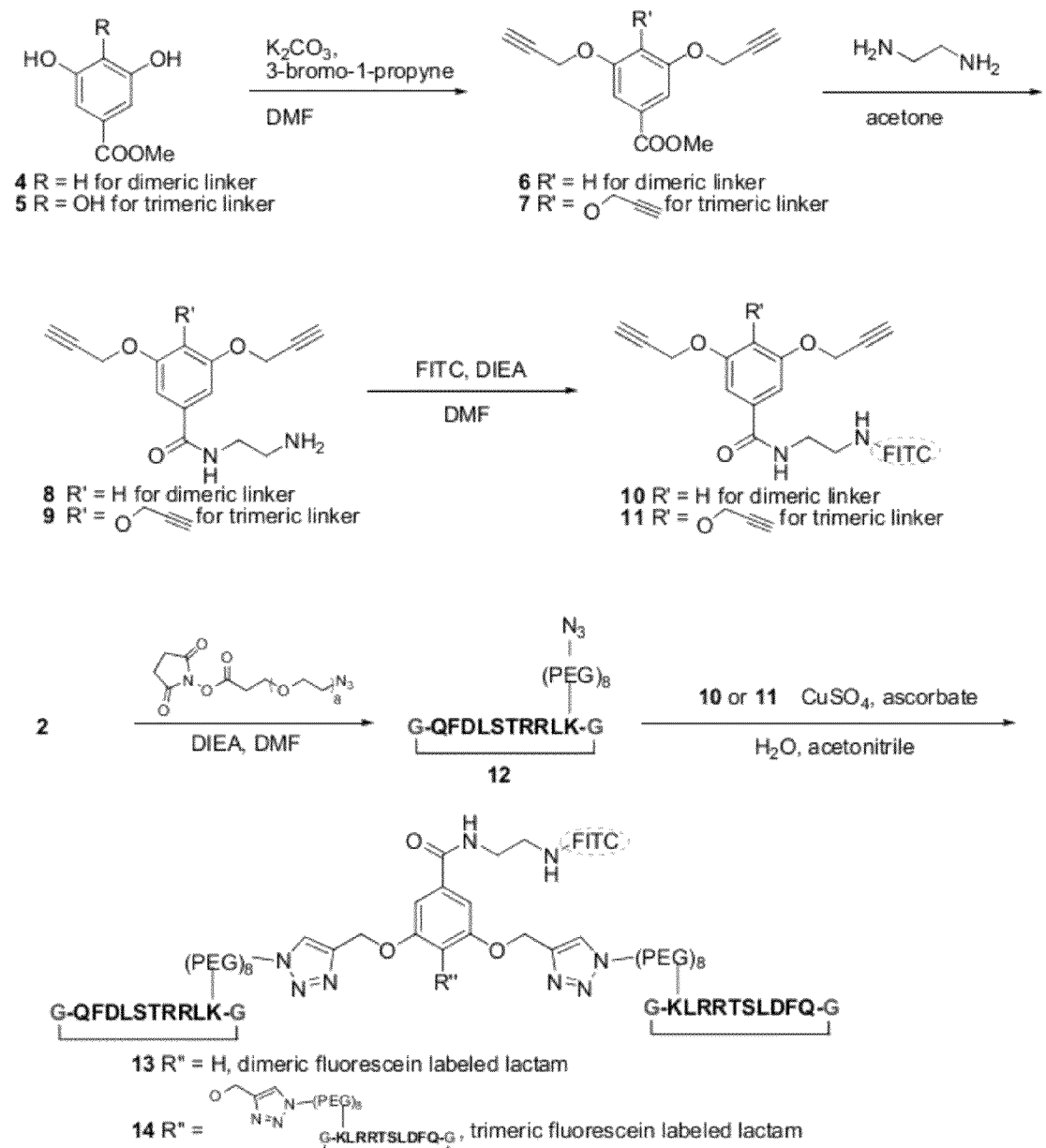
FIG. 20 illustrates synthesis of dimeric and trimeric meditopes according to some embodiments, which include peptide sequences SEQ ID NO: 22 (G-QFDLSTRRLK-G) and SEQ ID NO: 55 (G-KLRRTSLDFQ-G).

Synthesis of a FITC-labeled bivalent meditope was developed based on "Click" chemistry using (compound 2 or SEQ ID NO:22) (FIG. 20). The use of templates 4 and 5 (FIG. 20) allows for the formation of both bi- and trivalent meditopes, respectively. This synthesis represents an exciting advance since the present discovery describes the chemistry developed for the preparation of multivalent meditopes and allows focus on investigating differing length polyethylene glycol (PEG) (and other) linkers for optimal binding. The synthetic approach is also amenable to DOTA incorporation for radionuclide imaging. For example, a 30 Å PEG bifunctional arm has been incorporated in the synthesis of a FITC-labeled divalent meditope, namely compound 13 (FIG. 20). The distance between the CDR regions within an IgG is ~130 Å. Therefore, the length of the PEG linker may be systematically varied to ensure this approach is optimal. End-to-end distances of commercially available PEGs extend to 90 Å (Pierce), which would exceed the IgG distance.

Multivalent Characterization

Each multivalent meditope is characterized by SPR and ITC to ensure that conjugation to the multivalent scaffold does not affect the meditope-IgG interaction. These measurements, however, are limited in their effectiveness in determining mutlivalency since the IgG is not bound to the surface of a tumor. Instead, FACS analysis and cell viability assays may be used to quantify the effect of the multivalent meditope directly on cells that overexpress EGFR.

For FACS analysis, cell lines that overexpress EGFR (MDA-MB-468 and A431) are incubated with cetuximab at various concentrations (1 nM to 100 nM). Next, cetuximab-treated cells are incubated with the labeled multivalent meditope (FIG. 24; Meditope-Fc) at increasing concentrations (0.1 nM to 1 µM) and analyze the binding characteristics using a CyAn FACS sorter. A shift at far lower concentrations than observed for the monovalent meditope (FIG. 24) and/or an increase in percentage of cells that shift may be observed. To further confirm the additive effects expected for the multivalent meditope, the non-labeled, monovalent meditope may be used to compete with the labeled multivalent meditope for the antigen-bound cetuximab.

The efficacy of the multivalent meditope at enhancing cetuximab-mediated cell death using cell viability assays may also be measured. Briefly, MDA-MB-468 and A431 cell lines are plated and treated with varying concentrations of cetuximab and multivalent meditopes. As a control, a monovalent meditope is used, which produces similar results as cetuximab alone. MTT, 3-(4,5-Dimethylthiazol-2-yl)-2,5-diphenyltetrazolium bromide, may be used to quantify the number of viable cells. For multivalent meditopes that demonstrate activity, Western blot analysis may be performed to follow the phosphorylation status of EGFR as well as AKT and MAP which are part of the EGFR signaling pathway. These data are then compared with data from cetuximab-only treated cells and cells treated with tyrosine kinase inhibitors (AG1478). Collectively, this should cause an increase in cell death as a function of multivalent meditope concentration.

MTT Assay

Figure 32:
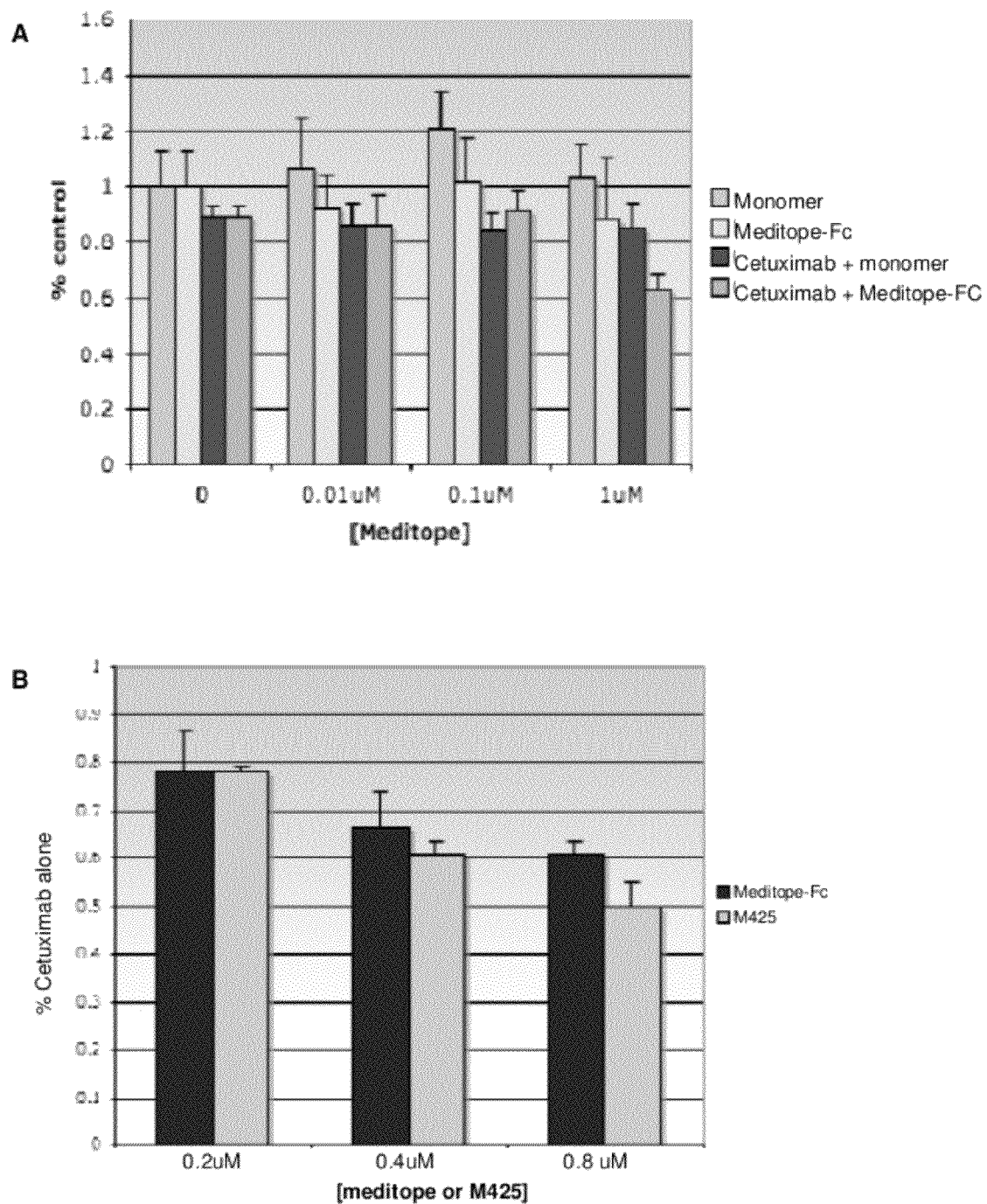
FIG. 32 illustrates the results of an MTT assay comparing the efficacy of a bivalent meditope-Fc to that of a monomeric meditope.

The effect of the monomeric meditope or the bivalent meditope-Fc on inducing cell death in conjunction with cetuximab was investigated using an MTT assay. 4000 MDA-MB-468 cells were placed in each well of a 96 well plate in 80 µl of medium. 10 µl of 1 µM cetuximab is added along with 10 µl of 0.1, 1 or 10 µM of meditope or meditope-Fc to a final concentration of 0.1 µM cetuximab and 0.01, 0.1 and 1 µM meditope or meditope-Fc. Each component was also added alone with PBS as control. After a 48-hour incubation, 10 µl of MTT reagent was added and let incubate for another 4 hours. The culture supernatant was then removed, 100 µl of MTT crystal dissolving reagent was added, and the plate was read at 630 nm. Meditope or meditope-Fc alone did not alter cell growth significantly, but only meditope-Fc and not the monomeric meditope could inhibit cell growth together with cetuximab (FIG. 32A).

To show that a multivalent meditope has efficacy in enhancing cell killing akin to the effect of a second anti-EGFR antibody in addition to cetuximab, the effect of tumor cell growth inhibition by either cetuximab with medito-Fc or cetuximab with M425 was compared. 4000 MDA-MB-468 cells were placed in each well of a 96 well plate in 80 µl of medium. 10 µl of 1 µM cetuximab is added along with 10 µl of either 2, 4 or 8 µM of meditope-Fc or M425 to a final concentration of 0.1 µM cetuximab and either 0.2, 0.4 or 0.8 µM meditope-Fc or M425. Cetuximab added along with PBS was used as control. After a 48-hour incubation, 10 µl of MTT reagent was added and let incubate for another 4 hours. The culture supernatant was then removed, 100 µl of MTT crystal dissolving reagent was added, and the plate was read at 630 nm. Meditope-Fc could be seen enhancing the cell-killing capacity of cetuximab, although not as yet potent as M425 (FIG. 32B).

As an alternate approach, different scaffolds and linkers may be used to generate high affinity multivalent meditopes. For example, DNA may be used as a scaffold for the meditopes to create a more rigid scaffold.

Figure 23:
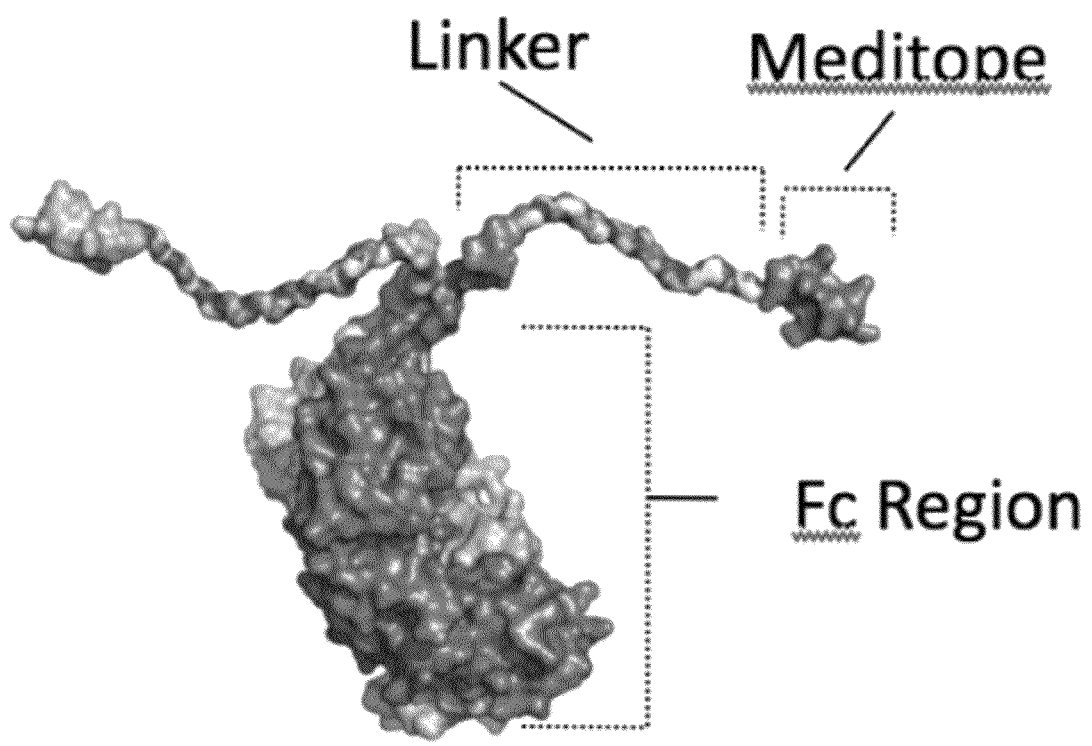
FIG. 23 shows the structure of a bivalent meditope. The meditope is directly fused to the N-terminus of a peptide linker that is directly fused to the Fc Region of an IgG. The Fc is naturally homodimeric. Thus the Meditope-Fc construct is bivalent.
Figure 24:
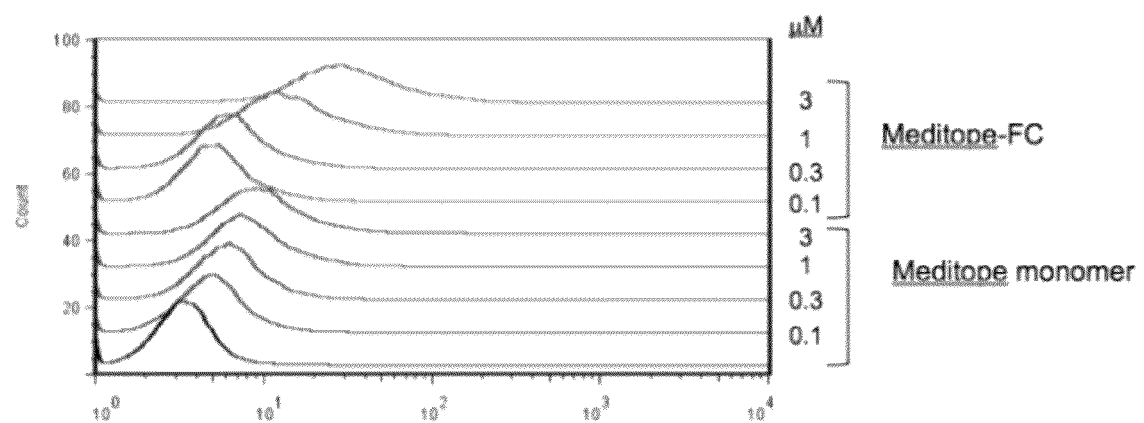
FIG. 24 shows the results from an exemplary FACS analysis. MDA-MB-468 cells that over express EGFR receptor were pre-treated with 10 nM of cetuximab for 30 minutes, rinsed, and then treated with either the meditope-Fc construct or the monomeric meditope at four concentrations. The bottom trace is a negative control (no antibody). Next four traces show that a monomeric meditope binds to cells pre-treated with the cetuximab in a concentration dependent manner. The top four traces also show that the bivalent, meditope Fc binds to cells pre-treated with the cetuximab in a concentration dependent manner, but with higher affinity (e.g. shifted to the right). This is predicted and consistent with a multivalent interaction.

The meditope (wildtype) was fused to the N-terminus of the Fc region of an IgG through a flexible peptide linker ("meditope-Fc") (FIG. 23; SEQ ID NO:3-4). The sequence and structure of the meditope-Fc are shown in FIGS. 22 and 23, respectively. The use of the Fc region to 'dimerize' ligands has been well established. In this example, a linker 17 amino acids long consisting of glycine and serines was chosen, but a linker of any suitable length may be used. To demonstrate enhanced binding due to multivalency, $0.5 \times 10^6$ MDA-MB-468 cells were labeled with 10 nM Cetuximab for 30 min at room temperature, washed, then incubated with 0.1, 0.3, 1 and 3 µM of bivalent Meditope-Fc or monomeric Meditope for 30 min, room temperature, washed and analyzed by FACS. As shown in FIG. 24, FACS analysis indicates that the meditope-Fc, corrected for the stoichiometry, binds cells pre-treated with cetuximab with significantly higher affinity. Furthermore, we demonstrate that this interaction is specific to the meditope-enabled mAb (cetuximab). This data indicates that the meditope-Fc combined with a meditope enabled mAb is synergistic and can be substituted for a second antibody.

Figure 21:
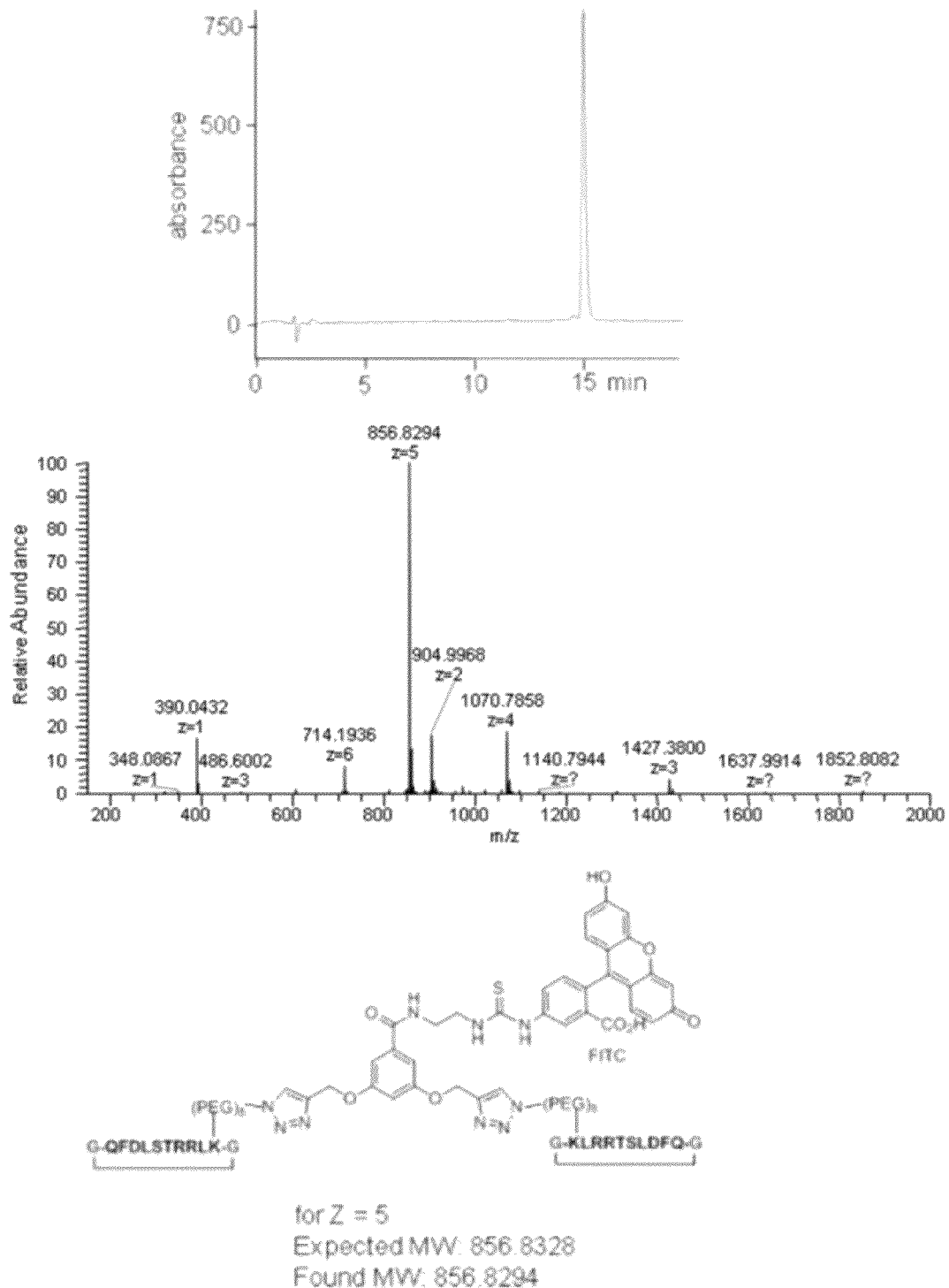
FIG. 21 illustrates the characterization of a fluorescein isothiocyanate (FITC)-labeled meditope dimer 7. The upper panel shows an HPLC trace of final bivalent meditope and the lower panel shows its mass spectrum (SEQ ID NOs:22, 55).

Different scaffolds of biological and chemical origin may also be used to achieve multivalency. This includes, but is not limited to, constructing a bivalent or trivalent scaffold, using streptavidin or collagen, strepavidin as a tetravalent scaffold, unique scaffolds, Origami DNA and the like. A chemical scaffold may also be created using molecules including, but not limited to, DNA (single strand, duplex, Holliday junctions, aptamers and the like), RNA (single strand, hairpin, stem loop, aptamers and the like), PNA (peptide nucleic acids), DNA/PNA duplexes and triplexes for rigidity, nanoparticles (directly coupled or coupled through organic polymers such as PEG), organic polymers that can form duplexes with themselves and/or with DNA or PNA. For example, in FIGS. 20 and 21, a trivalent meditope was successfully synthesized.

Figure 25:
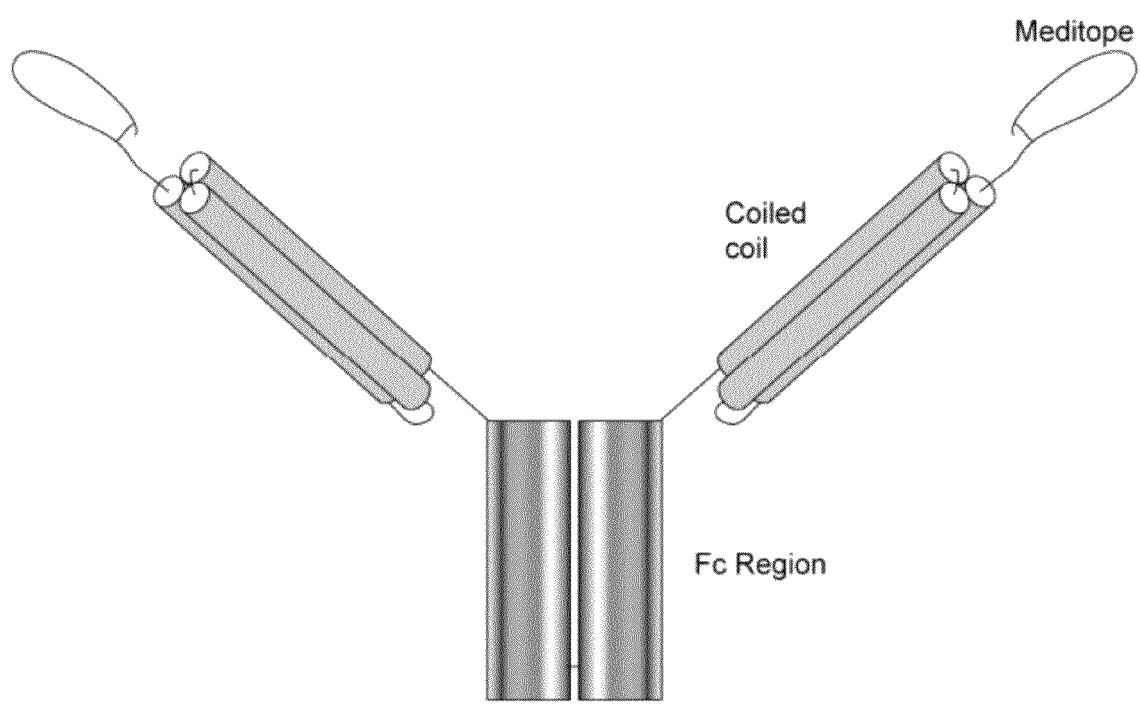
FIG. 25 is an alternative linker, including a coiled coil, which may be used accordance with certain embodiments.

In addition, the composition of and the distance between the Fc and meditope can be systematically explored to optimize affinity and specificity. In one embodiment, each natural or unnatural residue can be substituted at any position within the linker for optimization. In addition, a linker between 2 to 100 or more residues is possible (e.g., can be generated by current and future DNA synthesizers and inserted between the meditope and the Fc regions. The linker may also be 'rigidified' to limit the radius of gyration and to enhance the affinity and specificity of the Fc-meditope. For example, a coiled coil domain may be placed between the meditope and the Fc (FIG. 25). Alternatively, inert protein domains (e.g., immunoglobulin folds) may be substituted for the linker. Multiple immunoglobulin folds can be placed between the meditope and the Fc domain. In certain embodiments, the composition of the linker is of human origin to mitigate potential antigenicity.

EXAMPLE 6

Generation of Meditope Variants

Screening methods may be used to identify small molecule analogs that mimic the meditopes described herein. This includes fluorescence polarization assays, diffraction based and NMR based fragment screening, and tethering dynamic combinatorial methods.

Fluorescence polarization assays: To identify alternative molecules that can bind at the meditope site and be used for similar functions, a fluorescent marker (e.g., Alexafluor, rhodamine, fluorescein) may be conjugated to the original meditope using a suitable method (e.g., amines, sulfhydryl, carboxylate, sugars or other known methods) and allowed to interact with the Fab or mAb. The interaction between the labeled meditope and mAb causes a change in the fluorescence polarization/intensity of the fluorescent tag. Once established, small molecule compounds (MW<1000 Dal) are added and equilibrated with fluorescent tagged meditope-antibody complex and the fluorescence polarization is monitored. Compounds that block the meditope-antibody interaction will alter the fluorescent polarization properties. Accordingly, another embodiment is a method of identifying compounds that can be optimized and used for target delivery.

Methods

Figure 26:
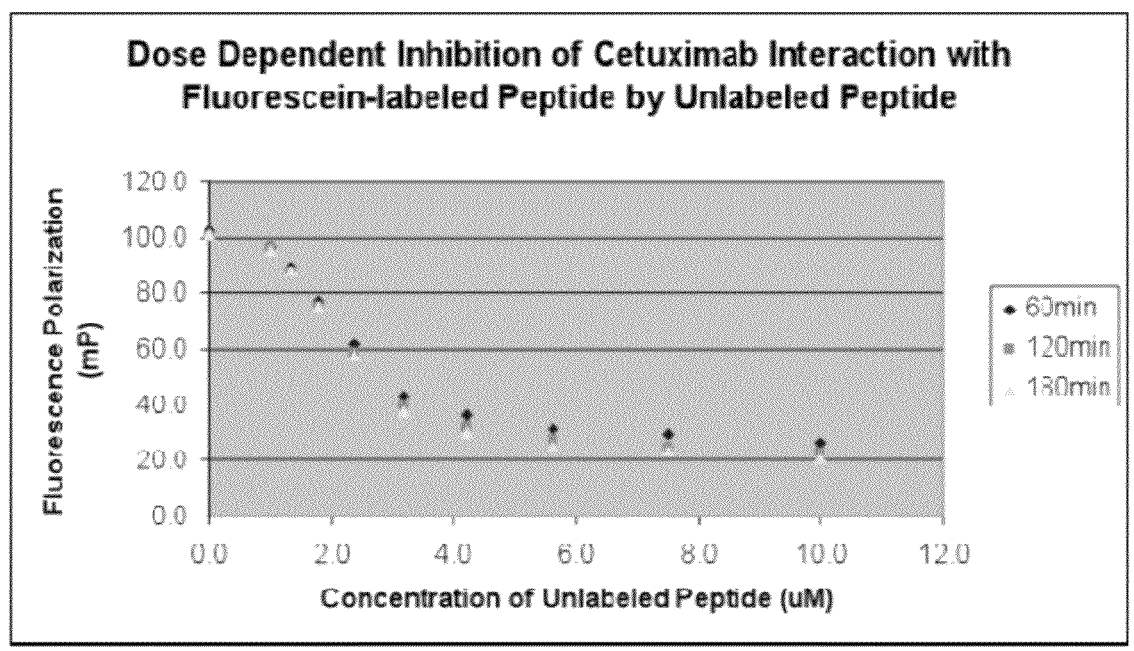
FIG. 26 illustrates a fluorescence polarization assay of dose-dependent inhibition of cetuximab interaction with fluorescein-labeled peptide by unlabeled peptide. The assay identified novel small molecule compounds that can compete with the meditope for mAb binding and thus can be developed to function in a similar manner as a meditope. As an important control, we demonstrate here that a non-labeled meditope can displace fluorescently-labeled meditope. Equilibration of the displacement at three times points indicates that the assay is robust and amendable to high throughput screening.
Figure 28:
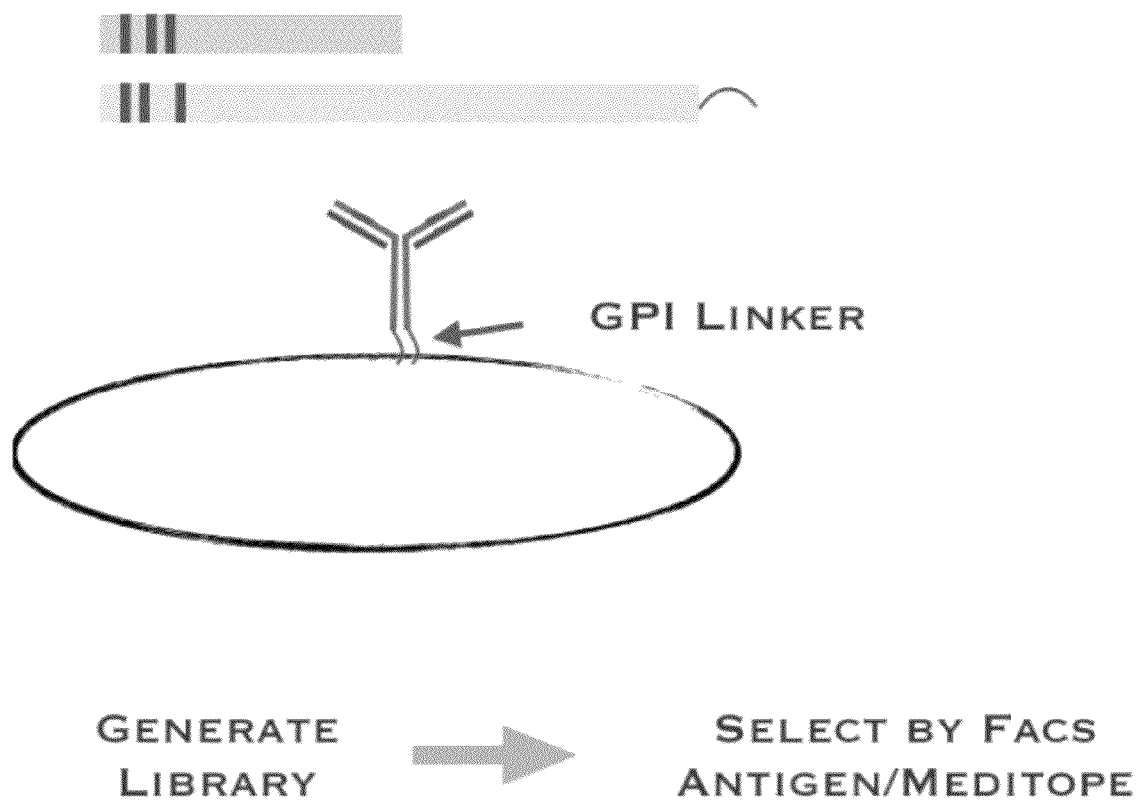
FIG. 28 illustrates steps to alter and/or enhance the binding affinity of a mAb for a meditope or compound binding at the meditope site using a directed random library. Specifically, a gene library where codons for mAb residues that line the meditope binding site are replaced with NNK (where N is any nucleotide and K is a Thymine or Guanosine) can be selected using FACs sorting (where the meditope and the antigen are labeled with distinct chromophores). The GPI linker ensures the selected mAb remains associated with the cell encoding the gene sequence. Sequencing the genes encoding the light can heavy chain from the selected cells will identify high affinity mAbs. The method can be repeated to selected for higher affinity meditope or meditope analogs.

The cyclic meditope was synthesized and chemically attached to a fluorescein having the following sequence: CQFDLSTRRLKCGGSK-Fluorescein (SEQ ID NO:21; cysteines form a disulfide). The fluorescent-labeled peptide was then titrated with cetuximab and the fluorescence polarization was measured. The dissociation constant, 1 µM, closely matched values obtained from surface plasmon resonance and isothermal titration calorimetry. Next, a non-labeled meditope, CQFDLSTRRLKCGGSK (SEQ ID NO:21), was used to displace the fluoroscein-label peptide pre-bound to Cetuximab (FIG. 26). A sigmoid curve indicative of a competition reaction was observed. Based on these data, an initial screen to identify a small molecule capable of displacing the meditope was initiated. In these preliminary studies, 42 lead compounds at concentrations of 50 µM were identified from a library of 30,000 small molecule compounds (see Tables 1 and 2 above). FIG. 27 shows five such lead compounds. Further characterization of these compounds is underway (e.g., crystallography).

Diffraction methods to identify meditope analogs. Diffraction based methods to identify lead compounds are well established (Shuker et al. 1996; Erlanson et al. 2001; Hughes et al. 2011). Since cetuximab Fab diffracts beyond 2.5 Å, this approach is viable to identify lead compounds or small molecule fragments that can be coupled to a meditope. In combination with these methods, a library of small molecules was developed to soak into crystals of cetuximab. Diffraction data from these soaks has been collected and several data sets have been analyzed. In these initial studies, two additional sites were identified on cetuximab that are amendable for fragment growth and optimization.

These fragments can be grown (chemically derivatized) to enhance their binding and specificity. These fragments can also be chemically tethered to the meditope. Optimization of this chemical coupling can significantly enhance the overall binding affinity. Additional analogs found by diffraction methods can be optimized and used in lieu of the meditope for drug delivery, multivalent scaffolding and other functions. Further, mutations in the light and heavy chains may be made to change the specificity of the ligand (meditope) and that these diffraction methods (including fluorescence polarization, NMR screening, and phage display methods) can be used to optimized alternative ligands.

Figure 29:
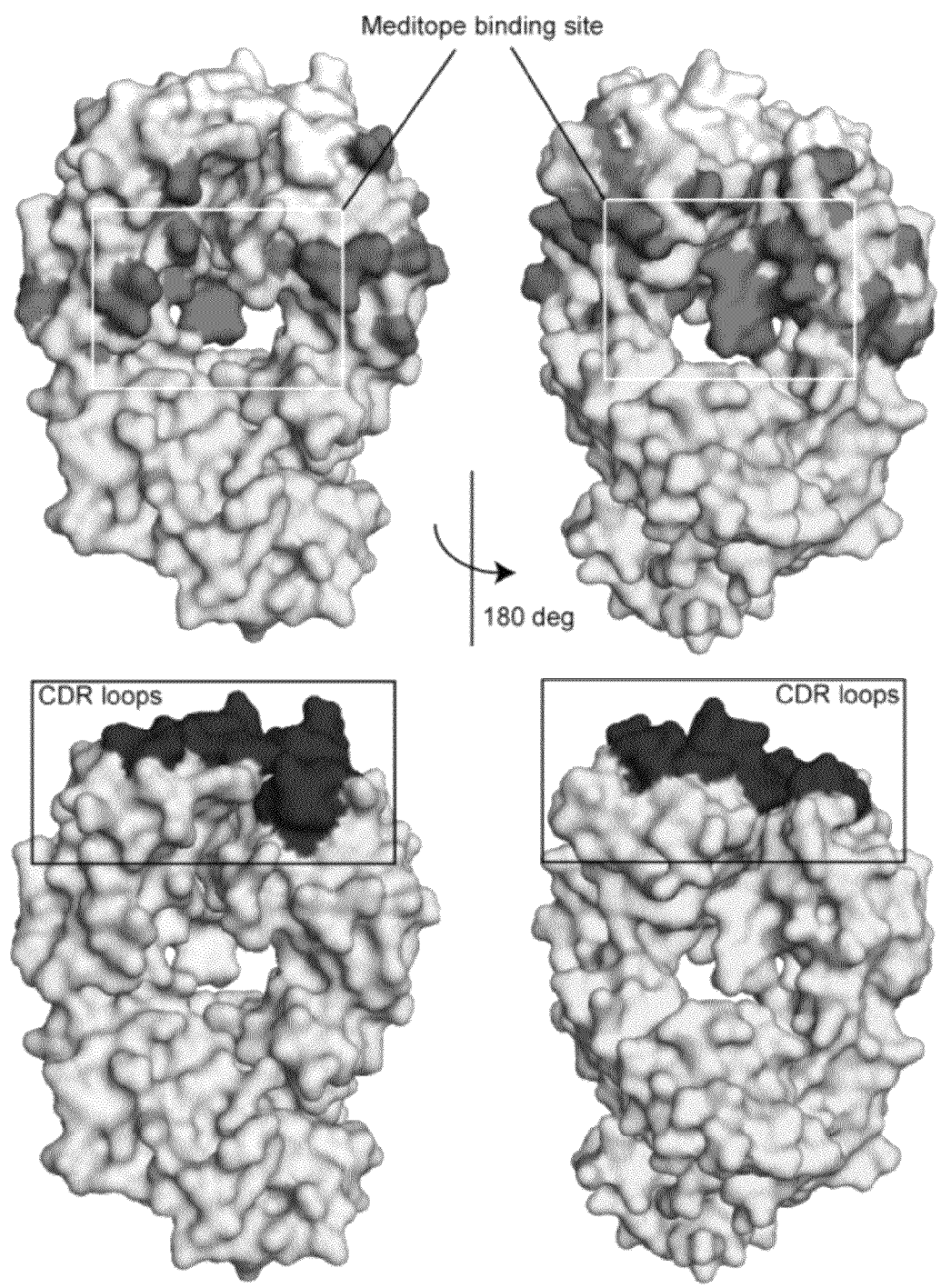
FIG. 29 shows 3D surface representations of sequence differences. The dark grey regions in the top panel indicate amino acid differences between cetuximab and the fully human trastuzumab framework. Residues inside the box have been mutated onto the trastuzumab framework. The CDR loops of trastuzumab have been identified (dark regions; bottom panel) and grafted onto the cetuximab framework.

Fragments by NMR screening: NMR can also be used to identify fragments that can be optimized and used in lieu of the meditope. To identify these leads, one dimensional (1D) spectra of pools containing 15 to 20 fragments were collected. Next, cetuximab was added to each pool and a second 1D spectra was collected. Compounds that bind (transiently) with cetuximab undergo rapid magnetization transfer, resulting in a loss of intensity. Thus, comparing the spectra before and after cetuximab and identify peaks that are altered indicates an interaction. These peaks can be pre-assigned to a specific compound and thus immediately known or the pools can be subdivided and the spectra recollected. After several rounds the exact identity of the compound is known. In these experiments, the precise position of the interaction is not known. The binding site can be determined by NMR or the fluorescence polarization assay. Alternatively, the Fab fragment can be labeled with NMR active and inactive nuclei (e.g., $^{13}C$, $^{15}N$ and $^{2}H$), multiple NMR experiments performed to assign the spectrum, and then used with the fragment library to identify the binding position. Using this procedure, a set of initial lead compounds has been identified (FIG. 29, bottom).

Virtual ligand screening: Virtual ligand screening is another method that can be used to identify lead compounds to function as a meditope. Using our crystal structure, standard programs (e.g., Schroerdinger Glide) can define a "box" about a site of a macromolecule (the meditope binding site) and dock known ligands to this site. Potential lead compounds are scored by a select energy function and the top 50 to 200 compounds can be purchased. In our initial studies, approximately 100 lead compounds have been identified, and using crystallography, these lead compounds should be shown to demonstrate that they bind to the meditope site.

REFERENCES

All references below and cited in the specification above are hereby incorporated by reference in their entirety, as if fully set forth herein.

1. Accardi, L., and Di Bonito, P. (2010) Antibodies in single-chain format against tumour-associated antigens: present and future applications, Curr Med Chem 17, 1730-1755.
2. Adams, G. P., Schier, R., McCall, A. M., Simmons, H. H., Horak, E. M., Alpaugh, R. K., Marks, J. D., and Weiner, L. M. (2001) Cancer Res 61, 4750-4755.
3. Adams, J., Behnke, M., Chen, S., Cruickshank, A. A., Dick, L. R., Grenier, L., Klunder, J. M., Ma, Y. T., Plamondon, L., and Stein, R. L. (1998) Potent and selective inhibitors of the proteasome: dipeptidyl boronic acids, Bioorg Med Chem Lett 8, 333-338.
4. Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002) Acta Crystallogr D Biol Crystallogr 58, 1948-1954.
5. Adessi, C., and Soto, C. (2002) Converting a peptide into a drug: strategies to improve stability and bioavailability, Curr Med Chem 9, 963-978.
6. Akamatsu, Y., Pakabunto, K., Xu, Z., Zhang, Y., and Tsurushita, N. (2007) Whole
7. IgG surface display on mammalian cells: Application to isolation of neutralizing chicken monoclonal anti-IL-12 antibodies, J Immunol Methods 327, 40-52.
8. Alley, S. C., Okeley, N. M., and Senter, P. D. (2010) Antibody-drug conjugates: targeted drug delivery for cancer, Curr Opin Chem Biol 14, 529-537.
9. Auffinger, P., Hays, F. A., Westhof, E., and Ho, P. S. (2004) Halogen bonds in biological molecules, Proc Natl Acad Sci USA 101, 16789-16794.
10. Beck, A., Wurch, T., Bailly, C., and Corvaia, N. (2010) Strategies and challenges for the next generation of therapeutic antibodies, Nat Rev Immunol 10, 345-352.
11. Beck, A., Wagner-Rousset, E., Bussat, M. C., Lokteff, M., Klinguer-Hamour, C., Haeuw, J. F., Goetsch, L., Wurch, T., Van Dorsselaer, A., and Corvaia, N. (2008) Trends in glycosylation, glycoanalysis and glycoengineering of therapeutic antibodies and Fc-fusion proteins, Curr Pharm Biotechnol 9, 482-501.
12. Bilgicer, B., Moustakas, D. T., and Whitesides, G. M. (2007) A synthetic trivalent hapten that aggregates anti-2, 4-DNP IgG into bicyclic trimers, J Am Chem Soc 129, 3722-3728.
13. Bilgicer B, Thomas S W 3rd, Shaw B F, Kaufman G K, Krishnamurthy V M, Estroff L A, Yang J, Whitesides G M., A non-chromatographic method for the purification of a bivalently active monoclonal IgG antibody from biological fluids. J AM CHEM SOC. 2009 JUL 8; 131(26):9361-7.
14. Bilgicer, B., Thomas, III, S. W., Shaw, B. F., Kaufman, G. K., Krishnamurthy, V. M., Estroff, L. A., Yang, J. and Whitesides, G. M. (2009) J. Am. Chem. Soc., 131, 9361-9367.
15. Bokemeyer, C., Bondarenko, I., Makhson, A., Hartmann, J. T., Aparicio, J., de Braud, F., Donea, S., Ludwig, H., Schuch, G., Stroh, C., Loos, A. H., Zubel, A., and Koralewski, P. (2009) Fluorouracil, leucovorin, and oxaliplatin with and without cetuximab in the first-line treatment of metastatic colorectal cancer, J Clin Oncol 27, 663-671.
16. Bretscher, L. E., Li, H., Poulos, T. L., and Griffith, O. W. (2003) Structural characterization and kinetics of nitric-oxide synthase inhibition by novel N5-(iminoalkyl)- and N5-(iminoalkenyl)-ornithines, J Biol Chem 278, 46789-46797.
17. Butlin, N. G., and Meares, C. F. (2006) Antibodies with infinite affinity: origins and applications, Acc Chem Res 39, 780-787.
18. Cardarelli, P. M., Quinn, M., Buckman, D., Fang, Y., Colcher, D., King, D. J., Bebbington, C., and Yarranton, G. (2002) Binding to CD20 by anti-B1 antibody or F(ab')(2) is sufficient for induction of apoptosis in B-cell lines, Cancer Immunol Immunother 51, 15-24.
19. Carson, K. R., Focosi, D., Major, E. O., Petrini, M., Richey, E. A., West, D. P., and Bennett, C. L. (2009) Lancet Oncol 10(8), 816-824
20. Chen, V. B., Arendall, W. B., 3rd, Headd, J. J., Keedy, D. A., Immormino, R. M., Kapral, G. J., Murray, L. W., Richardson, J. S., and Richardson, D. C. (2010) MolProbity: all-atom structure validation for macromolecular crystallography, Acta Crystallogr D Biol Crystallogr 66, 12-21.
21. Chih, H. W., Gikanga, B., Yang, Y., and Zhang, B. (2011) Identification of amino acid residues responsible for the release of free drug from an antibody-drug conjugate utilizing lysine-succinimidyl ester chemistry, J Pharm Sci 100, 2518-2525.
22. Chmura, A. J., Orton, M. S., and Meares, C. F. (2001) Antibodies with infinite affinity, Proc Natl Acad Sci USA 98, 8480-8484.
23. Cho, H. S., Mason, K., Ramyar, K. X., Stanley, A. M., Gabelli, S. B., Denney, D. W., Jr., and Leahy, D. J. (2003) Structure of the extracellular region of HER2 alone and in complex with the Herceptin Fab, Nature 421, 756-760.
24. Collis, A. V., Brouwer, A. P., and Martin, A. C. (2003) J Mol Biol 325, 337-354.
25. Dechant, M., Weisner, W., Berger, S., Peipp, M., Beyer, T., Schneider-Merck, T., Lammerts van Bueren, J. J., Bleeker, W. K., Parren, P. W., van de Winkel, J. G., and Valerius, T. (2008) Complement-dependent tumor cell lysis triggered by combinations of epidermal growth factor receptor antibodies, Cancer Res 68, 4998-5003.
26. Demarest, S. J., and Glaser, S. M. (2008) Antibody therapeutics, antibody engineering, and the merits of protein stability, Curr Opin Drug Discov Devel 11, 675-687.
27. DeNardo, G., and DeNardo, S. (2010) Dose intensified molecular targeted radiotherapy for cancer-lymphoma as a paradigm, Semin Nucl Med 40, 136-144.
28. Derksen, D. J., Stymiest, J. L., and Vederas, J. C. (2006) Antimicrobial leucocin analogues with a disulfide bridge replaced by a carbocycle or by noncovalent interactions of allyl glycine residues, J Am Chem Soc 128, 14252-14253.
29. Donaldson, J. M., Kari, C., Fragoso, R. C., Rodeck, U., and Williams, J. C. (2009) Design and development of masked therapeutic antibodies to limit off-target effects: application to anti-EGFR antibodies, Cancer Biol Ther 8, 2147-2152.

30. Doppalapudi, V. R., Huang, J., Liu, D., Jin, P., Liu, B., Li, L., Desharnais, J., Hagen, C., Levin, N. J., Shields, M. J., Parish, M., Murphy, R. E., Del Rosario, J., Oates, B. D., Lai, J. Y., Matin, M. J., Ainekulu, Z., Bhat, A., Bradshaw, C. W., Woodnutt, G., Lerner, R. A., and Lappe, R. W. (2010) Chemical generation of bispecific antibodies, Proc Natl Acad Sci USA 107, 22611-22616.

31. Doppalapudi, V. R., Tryder, N., Li, L., Aja, T., Griffith, D., Liao, F. F., Roxas, G., Ramprasad, M. P., Bradshaw, C., and Barbas, C. F., 3rd. (2007) Chemically programmed antibodies: endothelin receptor targeting CovX-Bodies, Bioorg Med Chem Lett 17, 501-506.

32. Dornan, D., Bennett, F., Chen, Y., Dennis, M., Eaton, D., Elkins, K., French, D., Go, M. A., Jack, A., Junutula, J. R., Koeppen, H., Lau, J., McBride, J., Rawstron, A., Shi, X., Yu, N., Yu, S. F., Yue, P., Zheng, B., Ebens, A., and Polson, A. G. (2009) Therapeutic potential of an anti-CD79b antibody-drug conjugate, anti-CD79b-vc-MMAE, for the treatment of non-Hodgkin lymphoma, Blood 114, 2721-2729.

33. Du, J., Wang, H., Zhong, C., Peng, B., Zhang, M., Li, B., Huo, S., Guo, Y., and Ding, J. (2007) Structural basis for recognition of CD20 by therapeutic antibody Rituximab, J Biol Chem 282, 15073-15080

34. Emsley, P., and Cowtan, K. (2004) Acta Crystallogr D Biol Crystallogr 60, 2126-2132.

35. Erlanson, D. A., Arndt, J. W., Cancilla, M. T., Cao, K., Elling, R. A., English, N., Friedman, J., Hansen, S. K., Hession, C., Joseph, I., Kumaravel, G., Lee, W. C., Lind, K. E., McDowell, R. S., Miatkowski, K., Nguyen, C., Nguyen, T. B., Park, S., Pathan, N., Penny, D. M., Romanowski, M. J., Scott, D., Silvian, L., Simmons, R. L., Tangonan, B. T., Yang, W., and Sun, L. (2011) Discovery of a potent and highly selective PDK1 inhibitor via fragment-based drug discovery, Bioorg Med Chem Lett 21, 3078-3083.

36. Ferenczy, G. G., and Keseru, G. M. (2010) Thermodynamics guided lead discovery and optimization, Drug Discov Today 15, 919-932.

37. Gencoglan, G., and Ceylan, C. (2007) Skin Pharmacol Physiol 20, 260-262.

38. Goodwin, D. A., and Meares, C. F. (1999) Pretargeted peptide imaging and therapy, Cancer Biother Radiopharm 14, 145-152.

39. Graille, M., Stura, E. A., Corper, A. L., Sutton, B. J., Taussig, M. J., Charbonnier, J. B., and Silverman, G. J. (2000) Proc Natl Acad Sci USA 97, 5399-5404.

40. Graille, M., Stura, E. A., Housden, N. G., Beckingham, J. A., Bottomley, S. P., Beale, D., Taussig, M. J., Sutton, B. J., Gore, M. G., and Charbonnier, J. B. (2001) Structure 9, 679-687.

41. Graille, M., Harrison, S., Crump, M. P., Findlow, S. C., Housden, N. G., Muller, B. H., Battail-Poirot, N., Sibai, G., Sutton, B. J., Taussig, M. J., Jolivet-Reynaud, C., Gore, M. G., and Stura, E. A. (2002) J' Biol Chem 277, 47500-47506.

42. Green, D. J., Pagel, J. M., Pantelias, A., Hedin, N., Lin, Y., Wilbur, D. S., Gopal, A., Hamlin, D. K., and Press, 0. W. (2007) Pretargeted radioimmunotherapy for B-cell lymphomas, Clin Cancer Res 13, 5598-5603.

43. Guay, D., Beaulieu, C., and Percival, M. D. (2010) Therapeutic utility and medicinal chemistry of cathepsin C inhibitors, Curr Top Med Chem 10, 708-716.

44. Hansel, T. T., Kropshofer, H., Singer, T., Mitchell, J. A., and George, A. J. (2010) The safety and side effects of monoclonal antibodies, Nat Rev Drug Discov 9, 325-338.

45. Hardegger, L. A., Kuhn, B., Spinnler, B., Anselm, L., Ecabert, R., Stihle, M., Gsell, B., Thoma, R., Diez, J., Benz, J., Plancher, J. M., Hartmann, G., Banner, D. W., Haap, W., and Diederich, F. (2011) Systematic investigation of halogen bonding in protein-ligand interactions, Angew Chem Int Ed Engl 50, 314-318.

46. Hartmann, C., Muller, N., Blaukat, A., Koch, J., Benhar, I., and Wels, W. S. (2010) Oncogene 29, 4517-4527.

47. Hernandes, M. Z., Cavalcanti, S. M., Moreira, D. R., de Azevedo Junior, W. F., and Leite, A. C. (2010) Halogen atoms in the modern medicinal chemistry: hints for the drug design, Curr Drug Targets 11, 303-314.

48. Hughes, S. J., Millan, D. S., Kilty, I. C., Lewthwaite, R. A., Mathias, J. P., O'Reilly, M. A., Pannifer, A., Phelan, A., Stuhmeier, F., Baldock, D. A., and Brown, D. G. (2011) Fragment based discovery of a novel and selective PI3 kinase inhibitor, Bioorg Med Chem. Lett.

49. Hutchins, B. M., Kazane, S. A., Staflin, K., Forsyth, J. S., Felding-Habermann, B., Schultz, P. G., and Smider, V. V. (2011) Site-specific coupling and sterically controlled formation of multimeric antibody fab fragments with unnatural amino acids, J Mol Biol 406, 595-603.

50. Junutula, J. R., Raab, H., Clark, S., Bhakta, S., Leipold, D. D., Weir, S., Chen, Y., Simpson, M., Tsai, S. P., Dennis, M. S., Lu, Y., Meng, Y. G., Ng, C., Yang, J., Lee, C. C., Duenas, E., Gorrell, J., Katta, V., Kim, A., McDorman, K., Flagella, K., Venook, R., Ross, S., Spencer, S. D., Lee Wong, W., Lowman, H. B., Vandlen, R., Sliwkowski, M. X., Scheller, R. H., Polakis, P., and Mallet, W. (2008) Site-specific conjugation of a cytotoxic drug to an antibody improves the therapeutic index, Nat Biotechnol 26, 925-932.

51. Kamat, V., Donaldson, J. M., Kari, C., Quadros, M. R., Lelkes, P. I., Chaiken, I., Cocklin, S., Williams, J. C., Papazoglou, E., and Rodeck, U. (2008) Enhanced EGFR inhibition and distinct epitope recognition by EGFR antagonistic mAbs C225 and 425, Cancer Biol Ther 7, 726-733.

52. Kiessling, L. L., and Splain, R. A. (2010) Chemical approaches to glycobiology, Annu Rev Biochem 79, 619-653.

53. Ladbury, J. E., Klebe, G., and Freire, E. (2010) Adding calorimetric data to decision making in lead discovery: a hot tip, Nat Rev Drug Discov 9, 23-27.

54. Lazar, G. A., Dang, W., Karki, S., Vafa, 0., Peng, J. S., Hyun, L., Chan, C., Chung, H. S., Eivazi, A., Yoder, S. C., Vielmetter, J., Carmichael, D. F., Hayes, R. J., and Dahiyat, B. I. (2006) Engineered antibody Fc variants with enhanced effector function, Proc Natl Acad Sci USA 103, 4005-4010.

55. Lesch, H. P., Kaikkonen, M. U., Pikkarainen, J. T., and Yla-Herttuala, S. (2010) Avidin-biotin technology in targeted therapy, Expert Opin Drug Deliv 7, 551-564.

56. Li, M., Yan, Z., Han, W., and Zhang, Y. (2006) Cell Immunol 239, 136-143.

57. Li, S., Schmitz, K. R., Jeffrey, P. D., Wiltzius, J. J., Kussie, P., and Ferguson, K. M. (2005) Structural basis for inhibition of the epidermal growth factor receptor by cetuximab, Cancer Cell 7, 301-311.

58. Liu, C. C., and Schultz, P. G. (2010) Adding new chemistries to the genetic code, Annu Rev Biochem 79, 413-444.

59. Lowe C R, Lowe A R, Gupta G. (2001) J. Biochem. Bioph. Meth. 49: 561-574.

60. Mammen, M., Choi, S.-K., and Whitesides, G. M. Polyvalent Interactions in Biological Systems: Implications for Design and Use of Multivalent Ligands and Inhibitors, (1998) Angew. Chem. Int. Ed. Engl., 37, 2749-2798.

61. McCoy, A. J., Grosse-Kunstleve, R. W., Adams, P. D., Winn, M. D., Storoni, L. C., and Read, R. J. (2007) J Appl Crystallogr 40, 658-674.

62. Meares, C. F. (2008) The chemistry of irreversible capture, Adv Drug Deliv Rev 60, 1383-1388.
63. Meira, D. D., Nobrega, I., de Almeida, V. H., Mororo, J. S., Cardoso, A. M., Silva, R. L., Albano, R. M., and Ferreira, C. G. (2009) Eur J Cancer 45, 1265-1273.
64. Melosky, B., Burkes, R., Rayson, D., Alcindor, T., Shear, N., and Lacouture, M. (2009) Curr Oncol 16(1), 16-26.
65. Meredith, R. F., and Buchsbaum, D. J. (2006) Pretargeted radioimmunotherapy, Int J Radiat Oncol Biol Phys 66, S57-59.
66. Milo, L. J., Lai, J. H., Wu, W., Liu, Y., Maw, H., Li, Y., Jin, Z., Shu, Y., Poplawski, S., Wu, Y., Sanford, D. G., Sudmeier, J. L., and Boehm/chin, B. (2011) Chemical and Biological Evaluation of Dipeptidyl Boronic Acid Proteasome Inhibitors for Use in Pro- and Pro-soft Drugs Targeting Solid Tumors, J Med Chem (in press—DOI: 10.1021/jm200460q).
67. Molloy, E. S., and Calabrese, L. H. (2009) Nat Rev Rheumatol 5(8), 418-419.
68. Morse, L, and Calarese, P. (2006) Semin Oncol Nurs 22(3), 152-162.
69. Moss, L. S., Starbuck, M. F., Mayer, D. K., Harwood, E. B., and Glotzer, J. (2009) Oncol Nurs Forum 36, 676-685.
70. Mossessova, E., and Lima, C. D. (2000) Mol Cell 5, 865-876.
71. Muller, D., and Kontermann, R. E. (2010) Bispecific antibodies for cancer immunotherapy: Current perspectives, BioDrugs 24, 89-98.
72. Muller, S., Lange, S., Gautel, M., and Wilmanns, M. (2007) Rigid conformation of an immunoglobulin domain tandem repeat in the A-band of the elastic muscle protein titin, J Mol Biol 371, 469-480.
73. Nicola, G., Peddi, S., Stefanova, M., Nicholas, R. A., Gutheil, W. G., and Davies, C. (2005) Crystal structure of Escherichia coli penicillin-binding protein 5 bound to a tripeptide boronic acid inhibitor: a role for Ser-110 in deacylation, Biochemistry 44, 8207-8217.
74. Pagel, J. M., Lin, Y., Hedin, N., Pantelias, A., Axworthy, D., Stone, D., Hamlin, D. K., Wilbur, D. S., and Press, O. W. (2006) Comparison of a tetravalent single-chain antibody-streptavidin fusion protein and an antibody-streptavidin chemical conjugate for pretargeted anti-CD20 radioimmunotherapy of B-cell lymphomas, Blood 108, 328-336.
75. Pakkala, M., Weisell, J., Hekim, C., Vepsalainen, J., Wallen, E. A., Stenman, U. H., Koistinen, H., and Narvanen, A. (2010) Mimetics of the disulfide bridge between the N- and C-terminal cysteines of the KLK3-stimulating peptide B-2, Amino Acids 39, 233-242.
76. Pugashetti, R., and Koo, J. (2009) J Dermatolog Treat 20(3), 132-136.
77. Rao, J., Lahiri, J., Isaacs, L., Weis, R. M., and Whitesides, G. M. (1998) A trivalent system from vancomycin.D-ala-D-Ala with higher affinity than avidin.biotin, Science 280, 708-711.
78. Riemer, A. B., Klinger, M., Wagner, S., Bernhaus, A., Mazzucchelli, L., Pehamberger, H., Scheiner, 0., Zielinski, C. C., and Jensen-Jarolim, E. (2004) J Immunol 173, 394-401.
79. Riemer, A. B., Kurz, H., Klinger, M., Scheiner, 0., Zielinski, C. C., and Jensen-Jarolim, E. (2005) Vaccination with cetuximab mimotopes and biological properties of induced anti-epidermal growth factor receptor antibodies, J Natl Cancer Inst 97, 1663-1670.
80. Rivera, F., Garcia-Castano, A., Vega, N., Vega-Villegas, M. E., and Gutierrez-Sanz, L. (2009) Cetuximab in metastatic or recurrent head and neck cancer: the EXTREME trial, Expert Rev Anticancer Ther 9, 1421-1428.
81. Roe, E., Garcia Muret, M. P., Marcuello, E., Capdevila, J., Pallares, C., and Alomar, A. (2006) J Am Acad Dermatol 55(3), 429-437.
82. Rossi, E. A., Goldenberg, D. M., Cardillo, T. M., McBride, W. J., Sharkey, R. M., and Chang, C. H. (2006) Stably tethered multifunctional structures of defined composition made by the dock and lock method for use in cancer targeting, Proc Natl Acad Sci USA 103, 6841-6846.
83. Rudnick, S. I., and Adams, G. P. (2009) Cancer Biother Radiopharm 24, 155-161.
84. Scheuer W, Friess T, Burtscher H, Bossenmaier B, Endl J, Hasmann M., Strongly enhanced antitumor activity of trastuzumab and pertuzumab combination
85. treatment on HER2-positive human xenograft tumor models. Cancer Res. 2009 Dec. 15; 69(24):9330-6.
86. Schrag, D., Chung, K. Y., Flombaum, C., and Saltz, L. (2005) J Natl Cancer Inst 97(16), 1221-1224.
87. Seeman, N. C. (2003) DNA in a material world, Nature 421, 427-431.
88. Shaav, T., Wiesmuller, K. H., and Walden, P. (2007) Vaccine 25, 3032-3037.
89. Shan, D., Ledbetter, J. A., and Press, O. W. (1998) Apoptosis of malignant human B cells by ligation of CD20 with monoclonal antibodies, Blood 91, 1644-1652.
90. Sharkey, R. M., Rossi, E. A., McBride, W. J., Chang, C. H., and Goldenberg, D. M. (2010) Recombinant bispecific monoclonal antibodies prepared by the dock-and-lock strategy for pretargeted radioimmunotherapy, Semin Nucl Med 40, 190-203.
91. Sheedy, C., MacKenzie, C. R., and Hall, J. C. (2007) Isolation and affinity maturation of hapten-specific antibodies, Biotechnol Adv 25, 333-352.
92. Shirasaki, Y., Nakamura, M., Yamaguchi, M., Miyashita, H., Sakai, O., and Inoue, J. (2006) Exploration of orally available calpain inhibitors 2: peptidyl hemiacetal derivatives, J Med Chem 49, 3926-3932.
93. Shuker, S. B., Hajduk, P. J., Meadows, R. P., and Fesik, S. W. (1996) Discovering high-affinity ligands for proteins: SAR by NMR, Science 274, 1531-1534.
94. Spangler, J. B., Neil, J. R., Abramovitch, S., Yarden, Y., White, F. M., Lauffenburger, D. A., and Wittrup, K. D. (2010) Combination antibody treatment down-regulates epidermal growth factor receptor by inhibiting endosomal recycling, Proc Natl Acad Sci USA 107, 13252-13257.
95. Stymiest, J. L., Mitchell, B. F., Wong, S., and Vederas, J. C. (2005) Synthesis of oxytocin analogues with replacement of sulfur by carbon gives potent antagonists with increased stability, J Org Chem 70, 7799-7809.
96. Teillaud, J. L. (2005) Engineering of monoclonal antibodies and antibody-based fusion proteins: successes and challenges, Expert Opin Biol Ther 5 Suppl 1, S15-27.
97. Thakur, A., and Lum, L. G. (2010) Cancer therapy with bispecific antibodies: Clinical experience, Curr Opin Mol Ther 12, 340-349.
98. Van Cutsem, E., Kohne, C. H., Nitre, E., Zaluski, J., Chang Chien, C. R., Makhson, A., D'Haens, G., Pinter, T., Lim, R., Bodoky, G., Roh, J. K., Folprecht, G., Ruff, P., Stroh, C., Tejpar, S., Schlichting, M., Nippgen, J., and Rougier, P. (2009) Cetuximab and chemotherapy as initial treatment for metastatic colorectal cancer, N Engl J Med 360, 1408-1417.
99. Wakankar, A. A., Feeney, M. B., Rivera, J., Chen, Y., Kim, M., Sharma, V. K., and Wang, Y. J. (2010) Physicochemical stability of the antibody-drug conjugate Trastuzumab- DM1: changes due to modification and conjugation processes, Bioconjug Chem 21, 1588-1595.

100. Young, W. W., Jr., Tamura, Y., Wolock, D. M., and Fox, J. W. (1984) J Immunol 133, 3163-3166.

What is claimed is:

1. A method of purifying a monoclonal antibody or antigen-binding fragment thereof, comprising
contacting a solution containing the monoclonal antibody or antigen-binding fragment thereof with a peptide coupled to a solid support, such that a meditope binding interface of the monoclonal antibody or fragment thereof binds to the peptide, and isolating the antibody or fragment, thereby purifying the antibody or fragment,
wherein the monoclonal antibody is cetuximab, and
wherein the peptide comprises an amino acid sequence selected from the group consisting of SEQ ID NOs: 1, 2, 5, 6, 7, 8, 21, 22, 26, 32, and 33.

2. The method of claim 1, wherein the peptide comprises the amino acid sequence of SEQ ID NO: 7 or 8.

3. The method of claim 1, wherein the peptide comprises an amino acid sequence selected from the group consisting of SEQ ID NOs: 1, 5, 6, and 22.

4. The method of claim 1, wherein the peptide comprises an amino acid sequence selected from the group consisting of SEQ ID NOs: 1, 5, 7, 8, 22, and 26.

5. The method of claim 1, wherein the peptide comprises the amino acid sequence selected from the group consisting of SEQ ID NOs: 5, 6, 7, 8, 21, 22, 26, 32, and 33.

6. The method of claim 1, wherein the peptide comprises the amino acid sequence of SEQ ID NO:32.

7. A method of purifying a monoclonal antibody or antigen-binding fragment thereof, comprising:
contacting a solution containing the monoclonal antibody or antigen-binding fragment thereof with a peptide coupled to a solid support, such that a meditope binding interface of the monoclonal antibody or fragment thereof binds the peptide, and isolating the antibody or fragment, thereby purifying the antibody or fragment,
wherein the monoclonal antibody is cetuximab, and
wherein the peptide comprises the sequence of SEQ ID NO: 32.

8. A method of purifying a monoclonal antibody or antigen-binding fragment thereof, comprising
contacting a solution containing the monoclonal antibody or antigen-binding fragment thereof with a peptide coupled to a solid support, such that a meditope binding interface of the monoclonal antibody or fragment thereof binds to the peptide, and isolating the antibody or fragment, thereby purifying the antibody or fragment,
wherein the monoclonal antibody is cetuximab, and
wherein the peptide comprises an amino acid sequence selected from the group consisting of SEQ ID NOs: 5, 6, 7, 8, 21, 22, 26, 32, and 33.

* * * * *

SEQUENCE LISTING

```
<160> NUMBER OF SEQ ID NOS: 58

<210> SEQ ID NO 1
<211> LENGTH: 12
<212> TYPE: PRT
<213> ORGANISM: Artificial Sequence
<220> FEATURE:
<223> OTHER INFORMATION: unmodified cQFD meditope

<400> SEQUENCE: 1

Cys Gln Phe Asp Leu Ser Thr Arg Arg Leu Lys Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: unmodified cQYN meditope

<400> SEQUENCE: 2

Cys Gln Tyr Asn Leu Ser Ser Arg Ala Leu Lys Cys
1               5                   10

<210> SEQ ID NO 3
<211> LENGTH: 867
<212> TYPE: DNA
<213> ORGANISM: Artificial Sequence
<220> FEATURE:
<223> OTHER INFORMATION: meditope-fc tethering agent

<400> SEQUENCE: 3
acacccaagc tggctagcga caccatgaag tgtagctggg tcatcttctt tctgatggca      60
gtcgtgacag gagtgaattc gtgccagttt gacctgtcaa ctcggcgact gaaatgcggt     120
gggggctccg gttcaggctc gggcggttca tcgggaggag ggggagggga acctaagtca     180
tgcgataaga cgcacacctg tcctccatgc ccagccccccg agttgcttgg tgggccctca    240
gtattcctct tccctccaaa acccaaagac accttgatga tttcccgcac gccggaagtc    300
acgtgtgtgg tcgtggatgt gagccatgag atcccgagg tgaagttcaa ttggtacgtg     360
gatggagtag aggtacacaa cgcgaaaacg aagcccaggg aggaacagta caattccaca    420
tatcgcgtgg tgtccgtgct tactgtgttg catcaagact ggctgaatgg gaaggagtat    480
aagtgcaaag tatcaaacaa ggcgctgcct gctccaatcg aaaagaccat ctcgaaggcg    540
aaaggacaac ccagagaacc ccaagtctac acgcttccgc cctcgcggga tgagctcacc    600
aaaaaccagg tatccctcac ttgtttggta aaaggattct acccgtcgga cattgcagtc    660
gagtgggagt cgaatgggca gccggaaaac aactacaaaa caacaccgcc cgtcttggac    720
tccgatggtt cgttctttct ctattcgaag ctcaccgtag acaagtcgag gtggcagcag    780
ggcaacgtct tttcgtgctc agtgatgcat gaggcccttc acaatcacta tacgcagaaa    840
agcctgagcc tgtcaccggg gaagtaa                                         867

<210> SEQ ID NO 4
<211> LENGTH: 288
<212> TYPE: PRT
<213> ORGANISM: Artificial Sequence
<220> FEATURE:
<223> OTHER INFORMATION: meditope-Fc tethering agent
```

-continued

```
<400> SEQUENCE: 4

Thr Pro Lys Leu Ala Ser Asp Thr Met Lys Cys Ser Trp Val Ile Phe
1               5                   10                  15

Phe Leu Met Ala Val Val Thr Gly Val Asn Ser Cys Gln Phe Asp Leu
            20                  25                  30

Ser Thr Arg Arg Leu Lys Cys Gly Gly Ser Gly Ser Gly Ser Gly
        35                  40                  45

Gly Ser Ser Gly Gly Gly Gly Glu Pro Lys Ser Cys Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 5
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (2)..(2)
<223> OTHER INFORMATION: Gln is D-glutamine

<400> SEQUENCE: 5

Cys Gln Phe Asp Leu Ser Thr Arg Arg Leu Lys Cys
1               5                   10

<210> SEQ ID NO 6
<211> LENGTH: 12
<212> TYPE: PRT
<213> ORGANISM: Artificial Sequence
<220> FEATURE:
```

-continued

```
<223> OTHER INFORMATION: modified meditope variant sequence

<400> SEQUENCE: 6

Cys Gln Tyr Asp Leu Ser Thr Arg Arg Leu Lys Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (3)..(3)
<223> OTHER INFORMATION: Xaa is beta-beta-di-phenyl-Ala

<400> SEQUENCE: 7

Cys Gln Xaa Asp Leu Ser Thr Arg Arg Leu Lys Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (5)..(5)
<223> OTHER INFORMATION: Xaa is beta-beta-di-phenyl-Ala

<400> SEQUENCE: 8

Cys Gln Phe Asp Xaa Ser Thr Arg Arg Leu Lys Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (9)..(9)
<223> OTHER INFORMATION: Xaa is citrulline

<400> SEQUENCE: 9

Cys Gln Phe Asp Phe Ser Thr Arg Xaa Leu Lys Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 10

Cys Gln Phe Asp Phe Ser Thr Arg Arg Leu Lys Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 11
```

```
Cys Gln Phe Asp Glu Ser Thr Arg Arg Leu Lys Cys
1               5                   10
```

<210> SEQ ID NO 12
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 12

```
Cys Gln Phe Asp Tyr Ser Thr Arg Arg Leu Lys Cys
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 13

```
Cys Gln Phe Asp Leu Ser Thr Arg Arg Gln Lys Cys
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 14

```
Cys Gln Phe Asp Leu Ser Thr Arg Gln Leu Lys Cys
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 15

```
Cys Gln Tyr Asn Leu Ser Thr Ala Arg Leu Lys Cys
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 16

```
Cys Gln Ala Asp Leu Ser Thr Arg Arg Leu Lys Cys
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 17

```
Cys Gln Phe Asp Ala Ser Thr Arg Arg Leu Lys Cys
```

```
1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 18

```
Cys Gln Phe Asp Leu Ser Thr Ala Arg Leu Lys Cys
1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 19

```
Cys Gln Phe Asp Leu Ser Thr Arg Arg Ala Lys Cys
1               5                   10
```

<210> SEQ ID NO 20
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 20

```
Cys Gln Phe Asp Leu Ser Thr Arg Arg Glu Lys Cys
1               5                   10
```

<210> SEQ ID NO 21
<211> LENGTH: 16
<212> TYPE: PRT
<213> ORGANISM: Artificial Sequence
<220> FEATURE:
<223> OTHER INFORMATION: modified meditope variant sequence

<400> SEQUENCE: 21

```
Cys Gln Phe Asp Leu Ser Thr Arg Arg Leu Lys Cys Gly Gly Ser Lys
1               5                   10                  15
```

<210> SEQ ID NO 22
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 22

```
Gly Gln Phe Asp Leu Ser Thr Arg Arg Leu Lys Gly
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 23

```
Gly Gln His Asp Leu Ser Thr Arg Arg Leu Lys Gly
1               5                   10
```

<210> SEQ ID NO 24
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 24

Gly Gln Asn Asp Leu Ser Thr Arg Arg Leu Lys Gly
1               5                   10

<210> SEQ ID NO 25
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 25

Gly Gln Gln Asp Leu Ser Thr Arg Arg Leu Lys Gly
1               5                   10

<210> SEQ ID NO 26
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (3)..(3)
<223> OTHER INFORMATION: Xaa is 2-bromo-L-phenylalanine

<400> SEQUENCE: 26

Gly Gln Xaa Asp Leu Ser Thr Arg Arg Leu Lys Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (3)..(3)
<223> OTHER INFORMATION: Xaa is 3-bromo-L-phenylalanine

<400> SEQUENCE: 27

Gly Gln Xaa Asp Leu Ser Thr Arg Arg Leu Lys Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (3)..(3)
<223> OTHER INFORMATION: Xaa is 4-bromo-L-phenylalanine

<400> SEQUENCE: 28

Gly Gln Xaa Asp Leu Ser Thr Arg Arg Leu Lys Gly
1               5                   10

<210> SEQ ID NO 29
<211> LENGTH: 12

```
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (9)..(9)
<223> OTHER INFORMATION: Xaa is citrulline

<400> SEQUENCE: 29

Gly Gln Phe Asp Leu Ser Thr Arg Xaa Leu Lys Gly
1               5                   10

<210> SEQ ID NO 30
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (8)..(9)
<223> OTHER INFORMATION: Xaa is citrulline

<400> SEQUENCE: 30

Gly Gln Phe Asp Leu Ser Thr Xaa Xaa Leu Lys Gly
1               5                   10

<210> SEQ ID NO 31
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (8)..(8)
<223> OTHER INFORMATION: Xaa is citrulline

<400> SEQUENCE: 31

Gly Gln Phe Asp Leu Ser Thr Xaa Arg Leu Lys Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (11)..(11)
<223> OTHER INFORMATION: Xaa is 7-aminoheptanoic acid

<400> SEQUENCE: 32

Gln Phe Asp Leu Ser Thr Arg Arg Leu Lys Xaa
1               5                   10

<210> SEQ ID NO 33
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (1)..(1)
<223> OTHER INFORMATION: Xaa is beta-alanine
<220> FEATURE:
<221> NAME/KEY: misc_feature
<222> LOCATION: (12)..(12)
<223> OTHER INFORMATION: Xaa is beta-alanine
```

```
<400> SEQUENCE: 33

Xaa Gln Phe Asp Leu Ser Thr Arg Arg Leu Lys Xaa
1               5                   10

<210> SEQ ID NO 34
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (1)..(1)
<223> OTHER INFORMATION: Xaa is diaminopropionic acid
<220> FEATURE:
<221> NAME/KEY: misc_feature
<222> LOCATION: (12)..(12)
<223> OTHER INFORMATION: Xaa is iso-aspartic acid

<400> SEQUENCE: 34

Xaa Gln Phe Asp Leu Ser Thr Arg Arg Leu Lys Xaa
1               5                   10

<210> SEQ ID NO 35
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (1)..(1)
<223> OTHER INFORMATION: Xaa is beta-alanine
<220> FEATURE:
<221> NAME/KEY: misc_feature
<222> LOCATION: (12)..(12)
<223> OTHER INFORMATION: Xaa is iso-aspartic acid

<400> SEQUENCE: 35

Xaa Gln Phe Asp Leu Ser Thr Arg Arg Leu Lys Xaa
1               5                   10

<210> SEQ ID NO 36
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (1)..(1)
<223> OTHER INFORMATION: Xaa is diaminopropionic acid
<220> FEATURE:
<221> NAME/KEY: misc_feature
<222> LOCATION: (12)..(12)
<223> OTHER INFORMATION: Xaa is beta-alanine

<400> SEQUENCE: 36

Xaa Gln Phe Asp Leu Ser Thr Arg Arg Leu Lys Xaa
1               5                   10

<210> SEQ ID NO 37
<211> LENGTH: 9
<212> TYPE: PRT
<213> ORGANISM: Artificial Sequence
<220> FEATURE:
<223> OTHER INFORMATION: modified meditope variant sequence

<400> SEQUENCE: 37

Phe Asp Leu Ser Thr Arg Arg Leu Lys
```

```
<210> SEQ ID NO 38
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 38

Cys Gln Phe Asp Leu Ser Thr Arg Arg Leu Lys Cys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (11)..(11)
<223> OTHER INFORMATION: Xaa is 7-aminoheptanoic acid

<400> SEQUENCE: 39

Gln Tyr Asp Leu Ser Thr Arg Arg Leu Lys Xaa
1               5                   10

<210> SEQ ID NO 40
<211> LENGTH: 12
<212> TYPE: PRT
<213> ORGANISM: Artificial Sequence
<220> FEATURE:
<223> OTHER INFORMATION: modified meditope variant sequence
<220> FEATURE:
<221> NAME/KEY: misc_feature
<222> LOCATION: (1)..(1)
<223> OTHER INFORMATION: Xaa is beta-Azidoalanine
<220> FEATURE:
<221> NAME/KEY: misc_feature
<222> LOCATION: (12)..(12)
<223> OTHER INFORMATION: Xaa is propargylglycine

<400> SEQUENCE: 40

Xaa Gln Phe Asp Leu Ser Thr Arg Arg Leu Lys Xaa
1               5                   10

<210> SEQ ID NO 41
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 41

Gln Arg Thr Asn Gly Ser
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
```

<223> OTHER INFORMATION: light chain segment

<400> SEQUENCE: 42

Ile Ala Asp Tyr Tyr
1               5

<210> SEQ ID NO 43
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 43

Ala Gly Thr Lys Leu Glu
1               5

<210> SEQ ID NO 44
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 44

Gln Lys Pro Gly Gln Ser
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(5)
<223> OTHER INFORMATION: light chain segment

<400> SEQUENCE: 45

Leu Gly Val Tyr Phe
1               5

<210> SEQ ID NO 46
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 46

Ala Gly Thr Lys Leu Glu
1               5

<210> SEQ ID NO 47
<211> LENGTH: 6
<212> TYPE: PRT
<213> ORGANISM: Artificial Sequence

```
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 47

Gln Lys Pro Gly Lys Ala
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(5)
<223> OTHER INFORMATION: light chain segment

<400> SEQUENCE: 48

Phe Ala Thr Tyr Tyr
1               5

<210> SEQ ID NO 49
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 49

Gln Gly Thr Lys Val Glu
1               5

<210> SEQ ID NO 50
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: heavy chain segment

<400> SEQUENCE: 50

Gln Ser Pro Gly Lys Gly
1               5

<210> SEQ ID NO 51
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(4)
<223> OTHER INFORMATION: heavy chain segment

<400> SEQUENCE: 51

Gln Gly Thr Leu
1
```

```
<210> SEQ ID NO 52
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: heavy chain segment

<400> SEQUENCE: 52

Gln Asn Ile Gly Lys Ser
1               5

<210> SEQ ID NO 53
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(4)
<223> OTHER INFORMATION: heavy chain segment

<400> SEQUENCE: 53

Gln Gly Thr Ser
1

<210> SEQ ID NO 54
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: heavy chain segment

<400> SEQUENCE: 54

Gln Ala Pro Gly Lys Gly
1               5

<210> SEQ ID NO 55
<211> LENGTH: 12
<212> TYPE: PRT
<213> ORGANISM: Artificial Sequence
<220> FEATURE:
<223> OTHER INFORMATION: modified meditope variant sequence

<400> SEQUENCE: 55

Gly Lys Leu Arg Arg Thr Ser Leu Asp Phe Gln Gly
1               5                   10

<210> SEQ ID NO 56
<211> LENGTH: 12
<212> TYPE: PRT
<213> ORGANISM: Artificial Sequence
<220> FEATURE:
<223> OTHER INFORMATION: synthetically constructed linker sequence

<400> SEQUENCE: 56

Gly Gly Gly Ser Gly Gly Gly Ser Gly Gly Gly Ser
1               5                   10

<210> SEQ ID NO 57
<211> LENGTH: 16
```

```
<212> TYPE: PRT
<213> ORGANISM: Artificial Sequence
<220> FEATURE:
<223> OTHER INFORMATION: synthetically constructed linker sequence

<400> SEQUENCE: 57

Gly Gly Gly Ser Gly Gly Gly Ser Gly Gly Gly Ser Gly Gly Gly Ser
1               5                   10                  15

<210> SEQ ID NO 58
<211> LENGTH: 20
<212> TYPE: PRT
<213> ORGANISM: Artificial Sequence
<220> FEATURE:
<223> OTHER INFORMATION: synthetically constructed linker sequence

<400> SEQUENCE: 58

Gly Gly Gly Ser Gly Gly Gly Ser Gly Gly Gly Ser Gly Gly Gly Ser
1               5                   10                  15

Gly Gly Gly Ser
                20
```